United States Patent
Laible et al.

(10) Patent No.: US 11,785,943 B2
(45) Date of Patent: Oct. 17, 2023

(54) TUNABLE NANOTEXTURED MATERIALS

(71) Applicant: UCHICAGO ARGONNE, LLC, Chicago, IL (US)

(72) Inventors: Philip D. Laible, Villa Park, IL (US); Martyna Michalska, Lemont, IL (US); Philippe Noirot, Lemont, IL (US); Ralu Divan, Darien, IL (US); Igor Aronson, Lemont, IL (US); Andrey Sokolov, Lemont, IL (US)

(73) Assignee: UChicago Argonne, LLC, Chicago, IL (US)

( * ) Notice: Subject to any disclaimer, the term of this patent is extended or adjusted under 35 U.S.C. 154(b) by 0 days.

(21) Appl. No.: 16/138,948

(22) Filed: Sep. 21, 2018

(65) Prior Publication Data

US 2019/0090478 A1 Mar. 28, 2019

Related U.S. Application Data

(60) Provisional application No. 62/690,212, filed on Jun. 26, 2018, provisional application No. 62/562,244, filed on Sep. 22, 2017.

(51) Int. Cl.
*A01N 25/34* (2006.01)
*B82Y 30/00* (2011.01)
(Continued)

(52) U.S. Cl.
CPC ............. *A01N 25/34* (2013.01); *A01N 59/00* (2013.01); *B82Y 5/00* (2013.01); *B82Y 30/00* (2013.01); *B82Y 40/00* (2013.01); *B01L 2300/161* (2013.01); *B81B 2203/0361* (2013.01); *B81B 2203/0392* (2013.01); *B82B 3/0014* (2013.01); *B82B 3/0019* (2013.01); *C12Q 1/6806* (2013.01); *C12Q 1/689* (2013.01); *Y10T 428/24182* (2015.01); *Y10T 428/24355* (2015.01); *Y10T 428/24479* (2015.01)

(58) Field of Classification Search
None
See application file for complete search history.

(56) References Cited

U.S. PATENT DOCUMENTS

| 2003/0104296 A1 | 6/2003 | Hamano et al. |
| 2006/0115623 A1 * | 6/2006 | Aizenberg ............... B05D 5/04 428/141 |

(Continued)

FOREIGN PATENT DOCUMENTS

| CN | 101508419 A * | 8/2009 |
| CN | 101823685 A * | 9/2010 |

(Continued)

OTHER PUBLICATIONS

Linklater et al., Comment on "Bactericidal Effects of Natural Nanotopography of Dragonfly Wing on *Escherichia coli*", Aug. 2017, ACS Appl. Mater. Interfaces, vol. 9, Issue 35, pp. 29387-29393 (Year: 2017).*

(Continued)

*Primary Examiner* — Jeffrey A Vonch
(74) *Attorney, Agent, or Firm* — Foley & Lardner LLP

(57) ABSTRACT

A material with nanopillar structures extending from a substrate. The nanopillars are engageable by organisms to cause an interaction, such as cellular destruction.

5 Claims, 30 Drawing Sheets

(51) Int. Cl.
  *B82Y 40/00* (2011.01)
  *A01N 59/00* (2006.01)
  *B82Y 5/00* (2011.01)
  *B82B 3/00* (2006.01)
  *C12Q 1/6806* (2018.01)
  *C12Q 1/689* (2018.01)

(56) References Cited

U.S. PATENT DOCUMENTS

| | | | |
|---|---|---|---|
| 2007/0005024 A1* | 1/2007 | Weber | A61L 29/14 604/265 |
| 2008/0241926 A1* | 10/2008 | Lee | C12N 5/0068 435/395 |
| 2008/0296252 A1* | 12/2008 | D'Urso | B82Y 30/00 428/323 |
| 2010/0098909 A1* | 4/2010 | Reyssat | B08B 17/06 428/141 |
| 2010/0112234 A1* | 5/2010 | Spatz | C23C 18/1216 427/535 |
| 2010/0316842 A1* | 12/2010 | Tuteja | D06M 23/08 428/221 |
| 2011/0028305 A1* | 2/2011 | Lim | B01J 35/004 502/2 |
| 2011/0257040 A1 | 10/2011 | Turner et al. | |
| 2011/0300345 A1* | 12/2011 | Bessonov | B82Y 30/00 428/195.1 |
| 2012/0136312 A1* | 5/2012 | Terahara | A61B 5/150984 604/173 |
| 2012/0251611 A1* | 10/2012 | Luong-Van | A61L 27/18 424/443 |
| 2012/0268823 A1* | 10/2012 | Morhard | B81C 1/00031 359/580 |
| 2013/0109595 A1* | 5/2013 | Routenberg | B01J 19/0046 506/26 |
| 2014/0011013 A1* | 1/2014 | Jin | B05D 5/00 438/57 |
| 2014/0287019 A1* | 9/2014 | Ollerenshaw | A61K 9/0097 427/2.24 |
| 2015/0273755 A1* | 10/2015 | Yee | B81C 1/00206 264/293 |
| 2016/0113274 A1* | 4/2016 | Yamada | A61L 9/00 422/4 |
| 2016/0212989 A1* | 7/2016 | Juodkazis | C12Q 1/24 |
| 2016/0258020 A1* | 9/2016 | Lo | C12Q 1/6825 |
| 2017/0014111 A1* | 1/2017 | Hulseman | A61B 17/00 |
| 2017/0174848 A1* | 6/2017 | Gifford | C30B 33/10 |
| 2017/0258081 A1* | 9/2017 | Yamada | A01N 25/10 |
| 2018/0213772 A1* | 8/2018 | Xu | B82B 3/0014 |
| 2018/0272045 A1* | 9/2018 | Gifford | A61L 27/06 |
| 2018/0272048 A1* | 9/2018 | Gifford | A61L 27/50 |
| 2018/0320000 A1* | 11/2018 | Zhang | A01N 43/50 |
| 2019/0037841 A1* | 2/2019 | Zhang | A01N 59/20 |
| 2019/0093150 A1* | 3/2019 | Laible | A01N 25/34 |
| 2019/0246635 A1* | 8/2019 | Zhang | C09D 7/62 |

FOREIGN PATENT DOCUMENTS

| | | | |
|---|---|---|---|
| CN | 102701141 A | * 10/2012 | |
| CN | 103413865 A | * 11/2013 | |
| CN | 106006537 A | * 10/2016 | |
| CN | 107441564 A | * 12/2017 | A61L 31/088 |
| DE | 10124076 C1 | * 10/2002 | C03C 15/00 |
| WO | WO-2013007354 A1 | * 1/2013 | B82Y 40/00 |
| WO | WO-2013162482 A1 | * 10/2013 | B01L 3/508 |

OTHER PUBLICATIONS

Schneider et al., The Influence of Structure Heights and Opening Angles of Micro-and Nanocones on the Macroscopic Surface Wetting Properties, Feb. 2016, Scientific Reports, vol. 6 (Year: 2016).*

Martines et al., Superhydrophobicity and Superhydrophilicity of Regular Nanopatterns, Oct. 2005, Nano Letters, vol. 5, Issue 10, pp. 2097-2103 (Year: 2005).*

Atthi et al., Increasing Active Surface Area to Fabricate Ultra-Hydrophobic Surface by Using "Black Silicon" with Bosch Etching Process, Jun. 2012, Journal of Nanoscience and Nanotechnology, vol. 12, Issue 6, pp. 4919-4927 (Year: 2012).*

Ostrikov et al., Bactericidal effects of plasma-modified surface chemistry of silicon nanograss, Jul. 2016, Journal of Physics D: Applied Physics, vol. 49, No. 30 (Year: 016).*

Dorrer et al., Wetting of Silicon Nanograss: From Superhydrophilic to Superhydrophobic Surfaces, Jan. 2008, Advanced Materials, vol. 20, Issue 1, pp. 159-163 (Year: 2008).*

Susarrey-Arce et al., Bacterial viability on chemically modified silicon nanowire arrays, Mar. 2016, Journal of Materials Chemistry B, vol. 4, Issue 18, pp. 3104-3112 (Year: 2016).*

Hu et al., Bio-inspired silicon nanospikes fabricated by metal-assisted chemical etching for antibacterial surfaces, Dec. 2017, Applied Physics Letters, vol. 111, Issue 25, p. 253701 (Year: 2017).*

Choi et al., Fabrication of a dense array of tall nanostructures over a large sample area with sidewall profile and tip sharpness control, Oct. 2006, Nanotechnology, vol. 17, No. 21 (Year: 2006).*

Cheng et al., Fabrication of periodic arrays of needle-like Si nanowires on (001)Si and their enhanced field emission characteristics, May 2017, RSC Advances, vol. 7, 23935-23941 (Year: 2017).*

Choi et al., Fabrication of a dense array of tall nanostructures over a large sample area with sidewall profile and tip sharpness control, Oct. 2006, Nanotechnology, vol. 17, Issue 21 (Year: 2006).*

Hsu et al., Wafer-scale silicon nanopillars and nanocones by Langmuir-Blodgett assembly and etching, Oct. 2008, vol. 93, Issue 13 (Year: 2008).*

Gorshkov et al., Morphology of Nanoclusters and Nanopillars Formed in Nonequilibrium Surface Growth for Catalysis Applications, Nov. 2010, vol. 27, Issue 13, pp. 8554-8561 (Year: 2010).*

Mai et al., Dynamics of Wicking in Silicon Nanopillars Fabricated with Interference Lithography and Metal-Assisted Chemical Etching, Jul. 2012, Langmuir, vol. 28, Issue 31, pp. 11465-11471 (Year: 2012).*

Frommhold et al., High aspect ratio silicon and polyimide nanopillars by combination of nanosphere lithography and intermediate mask pattern transfer, Nov. 2012, Microelectronic Engineering, vol. 99, pp. 43-49 (Year: 2012).*

Bhadra et al., Antibacterial titanium nano-patterned arrays inspired by dragonfly wings, Nov. 2015, Scientific Reports, vol. 5 (Year: 2015).*

Yu et al., Extreme wettability of nanostructured glass fabricated by non-lithographic anisotropic etching, Mar. 2015, Scientific Reports, vol. 5 (Year: 2015).*

Liang et al., Inverted Silicon Nanopencil Array Solar Cells with Enhanced Contact Structures, Sep. 2016, Scientific Reports, vol. 6, Issue 1, p. 34139 (Year: 2016).*

Elbourne et al., Nano-structured antimicrobial surfaces: From nature to synthetic analogues, Dec. 2017, Journal of Colloid and Interface Science, vol. 508, pp. 603-616 (Year: 2017).*

Tripathy et al., Natural and bioinspired nanostructured bactericidal surfaces, Oct. 2017, Advances in Colloid and Interface Science vol. 248, pp. 85-10 (Year: 2017).*

Michalska et al., Tuning antimicrobial properties of biomimetic nanopatterned surfaces, Mar. 2018, Nanoscale, vol. 10, pp. 6639-6650 (Year: 2018).*

Bhadra et al., Subtle Variations in Surface Properties of Black Silicon Surfaces Influence the Degree of Bactericidal Efficiency, Feb. 2018, Nano-Micro Letters, vol. 10 (Year: 2018).*

Adams & Hunter, "Adaptation of intracytoplasmic membranes to altered light intensity in Rhodobacter sphaeroides," Biochimica et Biophysica Acta (BBA)—Bioenergetics 1817(9), pp. 1616-1627 (2012).

Anselme, et al., "The interaction of cells and bacteria with surfaces structured at the nanometre scale," Acta Biomaterialia 6(10), pp. 3824-3846 (2010).

(56) References Cited

OTHER PUBLICATIONS

Bandara, et al., "Bactericidal Effects of Natural Nanotopography of Dragonfly wing on *Escherichia coli*," ACS Applied Materials & Interfaces 9(8), p. 6746-6760 (2017).
Bhadra, et al., "Antibacterial titanium nano-patterned arrays inspired by dragonfly wings," Scientific Reports 5, 16817, 12 pages (2015).
Campoccia, et al., "A review of the biomaterials technologies for infection-resistant surfaces," Biomaterials 34(34), pp. 8533-8554 (2013).
Chen, et al., "Versatile antimicrobial peptide-based ZnO quantum dots for in vivo bacteria diagnosis and treatment with high specificity," Biomaterials 53, pp. 532-544 (2015).
Dickson, et al., "Nanopatterned polymer surfaces with bactericidal properties," Biointerphases 10(2), 021010, 8 pages (2015).
Dickson, et al., "Nanopatterned polymer surfaces with bactericidal properties," Biointerphases 10, 021010, 8 pages (2015).
Diu, et al., "Cicada-inspired cell-instructive nanopatterned arrays," Scientific Reports 4, 7122, 7 pages (2014).
Dou, et al., "Bioinspired Hierarchical Surface Structures with Tunable Wettability for Regulating Bacteria Adhesion," ACS Nano 9(11), pp. 10664-10672 (2015).
Drelich & Chibowski, "Superhydrophilic and Superwetting Surfaces: Definition and Mechanisms of Control," Langmuir 26(24), pp. 18621-18623 (2010).
Drelich, et al., "Hydrophilic and superhydrophilic surfaces and materials," Soft Matter 7, pp. 9804-9828 (2011).
Duran, et al., "Antimicrobial activity of biogenic silver nanoparticles, and silver chloride nanoparticles: an overviewand comments," Applied Microbiology and Biotechnology 100(15), pp. 6555-6570 (2016).
Dylla, et al., "Species differences in unlocking B-side electron transfer in bacterial reaction centers," FEBS Letters 590(16), pp. 2515-2526 (2016).
Elbourne, et al., "Nano-structured antimicrobial surfaces: From nature to synthetic analogues," Journal of Colloid and Interface Science 508, pp. 603-616 (2017).
Friedlander, et al., "Bacterial flagella explore microscale hummocks and hollows to increase adhesion," Proceedings of the National Academy of Sciences USA 110(14), pp. 5624-5629 (2013).
Gao, et al., "Application of Black Silicon for Nanostructure-Initiator Mass Spectrometry," Analytical Chemistry 88(3), pp. 1625-1630 (2016).
Genkin, et al., "Topological Defects in a Living Nematic Ensnare Swimming Bacteria," Physical Review X 7, 011029, 14 pages (2017).
Guttenplan, et al., "The cell biology of peritrichous flagella in Bacillus subtilis," Molecular Microbiology 87(1), pp. 211-229 (2013).
Hasan, et al., "Nanoscale Topography on BlacK Titanium Imparts Multi-biofunctional Properties for Orthopedic Applications," Scientific Reports 7, 41118, 13 pages (2017).
Hasan, et al., "Nanoscale Topography on Black Titanium Imparts Multi-biofunctional Properties for Orthopedic Applications," Scientific Reports 7, 4118, 13 pages (2017).
Hasan, et al., "Selective bactericidal activity of nanopatterned superhydrophobic cicada Psaltoda claripennis wing surfaces," Applied Microbiology and Biotechnology 97(20), pp. 9257-9262 (2013).
Henriques, et al., "Control of cell shape and elongation by the rodA gene in Bacillus subtilis," Molecular Microbiology 28(2), pp. 235-247 (1998).
Ivanoca, et al., "Bactericidal activity of black silicon," Nature Communications 4, 2838, 7 pages (2013).
Ivanova, et al., "Bactericidal activity of black silicon," Nature Communications 4, 2838, 7 pages (2013).
Ivanova, et al., "Natural Bactericidal Surfaces: Mechanical Rupture of Pseudomonas aeruginosa Cells by Cicada Wings," Small 8(16), pp. 2489-2494 (2012).
Jansen, et al., "Black silicon method X: a review on high speed and selective plasma etching of silicon with profile control: an in-depth comparison between Bosch and cryostat DRIE processes as a roadmap to next generation equipment," Journal of Micromechanics and Microengineering 19(3) (2009).
Jansen, et al., "Black silicon method X: a review on high speed and selective plasma etching of silicon with profile control: an in-depth comparison between Bosch and cryostat DRIE processes as a roadmap to next generation equipment," Journal of Micromechanics and Microengineering 19(3), 41 pages (2009).
Jansen, et al., "The black silicon method: a universal method for determining the parameter setting of a fluorine-based reactive ion etcher in deep silicon trench etching with profile control," Journal of Micromechanics and Microengineering 5(2), pp. 115-120 (1995).
Ji, et al., "Antibacterial applications of graphene-based nanomaterials: Recent achievements and challenges," Advanced Drug Delivery Reviews 105(B), pp. 176-189 (2016).
Kelleher, et al., "Cicada Wing Surface Topography: an Investigation into the Bactericidal Properties of Nanostructural Features," ACS Applied Materials & Interfaces 8(24), pp. 14966-14974 (2016).
Koebnik, et al., "Structure and function of bacterial outer membrane proteins: barrels in a nutshell," Molecular Microbiology 37(2), pp. 239-253 (2000).
Lee, et al., "Biocompatible Multifunctional Black-Silicon for Implantable Intraocular Sensor," Advanced Healthcare Materials 6(4), 1601356 (2017).
Lee, et al., "Biocompatible Multifunctional Black-Silicon for Implantable Intraocular Sensor," Advanced Healthcare Materials 6(4), 1601356, 12 pages (2017).
Liu, et al., "Black silicon: fabrication methods, properties and solar energy applications," Energy & Environmental Science 7, pp. 3223-3263 (20104).
Liu, et al., "Black silicon: fabrication methods, properties and solar energy applications," Energy & Environmental Science 7, pp. 3223-3263 (2014).
Liu, et al., "Sharper and Faster "Nano Darts" Kill More Bacteria: a Study of Antibacterial Activity of Individually Dispersed Pristine Single-Walled Carbon Nanotube," ACS Nano 3(12), pp. 3891-3902 (2009).
Lu & Barron, "In-Situ Fabrication of a Self-Aligned Selective Emitter Silicon Solar Cell Using the Gold Top Contacts to Facilitate the Synthesis of a Nanostructured Black Silicon Antireflective Layer Instead of an External Metal Nanoparticle Catalyst," ACS Applied Materials & Interfaces 7(22), pp. 11802-11814 (2015).
Min, et al., "Designer Dual Therapy Nanolayered Implant Coatings Eradicate Biofilms and Accelerate Bone Tissue Repair," ACS Nano 10(4), pp. 4441-4450 (2016).
Nguyen, et al., "Natural Insect and Plant Micro-/Nanostructsured Surfaces: an Excellent Selection of Valuable Templates with Superhydrophobic and Self-Cleaning Properties," Molecules 19(9), pp. 13614-13630 (2014).
Nie, et al., "Mussel-Inspired Antibacterial and Biocompatible Silver-Carbon Nanotube Composites: Green and Universal Nanointerfacial Functionalization," Langmuir 32(23), pp. 5955-5965 (2016).
Oestreicher, et al., "A comparison of the surface nanostructure from two different types of gram-negative cells: *Escherichia coli* and Rhodobacter sphaeroides," Micron 72, pp. 8-14 (2015).
Pezoldt, et al., "Black luminescent silicon," Physica Status Solidi 8(3), pp. 1021-1026 (2011).
Pham, et al., "Nanotopography as a trigger for the microscale, autogenous and passive lysis of erythrocytes," Journal of Materials Chemistry B 2, pp. 2819-2826 (2014).
Pham, et al., "'Race for the Surface': Eukaryotic Cells Can Win," ACS Applied Materials & Interfaces 8(34), pp. 22025-22031 (2016).
Pogodin, et al., "Biophysical Model of Bacterial Cell Interactions with Nanopatterned Cicada Wing Surfaces," Biophysical Journal 104(4), pp. 835-840 (2013).
Raj, et al., "*Rhodobacter viridis* sp. nov., a phototrophic bacterium isolated from mud of a stream," International Journal of Systematic and Evolutionary Microbiology 63, pp. 181-186 (2013).
Rhodes, "The Characterization of Pseudomonas fluorescens," The Journal of General Microbiology 21(1), pp. 221-268 (1959).
Sainiemi, et al., "Non-Reflecting Silicon and Polymer Surfaces by Plasma Etching and Replication," Advanced Materials 23(1), pp. 122-126 (2011).

(56) References Cited

OTHER PUBLICATIONS

Schmidt, et al., "Towards easily reproducible nano-structured SERS substrates," 2009 IEEE Sensors, pp. 1763-1767 (2009).
Schneider, et al., "NIH Image to ImageJ: 25 years of image analysis," Nature Methods 9, pp. 671-675 (2012).
Sengstock, et al., "Structure-related antibacterial activity of a titanium nanostructured surface fabricated by glancing angle sputter deposition," Nanotechnology 25(19), (2014).
Sengstock, et al., "Structure-related antibacterial activity of a titanium nanostructured surface fabricated by glancing angle sputter deposition," Nanotechnology 25(19), 195101, 11 pages (2014).
Singh, "Biotechnological applications of supersonic cluster beam-deposited nanostructured thin films: Bottom-up engineering to optimize cell-protein-surface interactions," Journal of Biomedical Materials Research 101(10), pp. 2994-3008 (2013).
Singh, et al., "Hydrophobic pinning with copper nanowhiskers leads to bactericidal properties," PLoS ONE 12(4), e0175428, 14 pages (2017).
Sjostrom, et al., "Bactericidal nanospike surfaces via thermal oxidation of Ti alloy substrates," Materials Letters 167, pp. 22-26 (2016).
Sportelli, et al., "Recent advances in the synthesis and characterization of nano-antimicrobials," TrAC Trends in Analytical Chemistry 84(A), pp. 131-138 (2016).
Stegich, et al., "The structural and optical properties of black silicon by inductively coupled plasma reactive ion etching," Journal of Applied Physics 116, 173503, 13 pages (2014).
Steglich, et al., "The structural and optical properties of black silicon by inductively coupled plasma reactive ion etching," Journal of Applied Physics 116, 173503, 13 pages (2014).
Susarrey-Arce, et al., "Bacterial viability on chemically modified silicon nanowire arrays," Journal of Materials Chemistry B 4, pp. 3104-3112 (2016).
Taguchi, et al., "Biochemical characterization and electron-transfer reactions of sym1, a Rhodobacter capsulatus reaction center symmetry mutant which affects the initial electron donor," Biochemistry 31(42), pp. 10345-10355 (1992).
Taute, et al., "High-throughput 3D tracking of bacteria on a standard phase contrast microscope," Nature Communications 6, 8776, 9 pages (2015).
Tripathy, et al., "Natural and bioinspired nanostructured bactericidal surfaces," Advances in Colloid and Interface Science 248, pp. 85-104 (2017).
Truong, et al., "The susceptibility of *Staphylococcus aureus* CIP 65.8 and Pseudomonas aeruginosa ATCC 9721 cells to the bactericidal action of nanostructured Calopteryx haemorrhoidalis damselfly wing surfaces," Applied Micriobiology and Biotechnology 101(11), pp. 4683-4690 (2017).
Truong, et al., "The susceptibility of *Staphylococcus aureus* CIP 65.8 and Pseudomonas aeruginosa ATCC 9721 cells to the bactericidal action of nanostructured Calopteryx haemorrhoidalis damselfly wing surfaces," Applied Microbiology and Biotechnology 101(11), pp. 4683-4690 (2017).
Turner, et al., "Different walls for rods and balls: the diversity of peptidoglycan," Molecular Microbiology 91(5), pp. 862-874 (2014).
Tuson, et al., "Measuring the stiffness of bacterial cells from growth rates in hydrogels of tunable elasticity," Molecular Microbiology 84(5), pp. 874-891 (2012).
Vadillo-Rodriguez & Dutcher, "Dynamic viscoelastic behavior of individual Gram-negative bacterial cells," Soft Matter 5, pp. 5012-5019 (2009).
Vadillo-Rodriguez & Dutcher, "Viscoelasticity of the bacterial cell envelope," Soft Matter 7, pp. 4101-4110 (2011).
Xie, et al., "Mechanical Model of Vertical Nanowire Cell Penetration," Nano Letters 13(12), pp. 6002-6008 (2013).
Xue, et al., "Theoretical study on the bactericidal nature of nanopatterned surfaces," Journal of Theoretical Biology 385, pp. 1-7 (2015).
Zhang, et al., "Superhydrophobic surfaces for the reduction of bacterial adhesion," RSC Advances 3, pp. 12003-12020 (2013).
Gudur & Ji, "Bio-Applications of Nanopillars," Frontiers in Nanoscience and Nanotechnology 2(6), pp. 1-10 (2016).
Lee, et al., "Protein patterning on silicon-based surface using background hydrophobic thin film," Biosensors and Bioelectronics 18(4), pp. 437-444 (2003).
Liu, et al., "Black silicon: fabrication methods, properties and solar energy applications," Energy & Environmental Science 7(10), pp. 3223-3263 (2014).
Park, et al., "Selective Surface Functionalization of Silicon Nanowires via Nanoscale Joule Heating," Nano Letters 7(10), pp. 3106-3111 (2007).
Yun, et al., "A self-heated silicon nanowire array: selective surface modification with catalytic nanoparticles by nanoscale Joule heating and its gas sensing applications," Nanoscale 5, pp. 6851-6856 (2013).
Fisher, et al., "Bactericidal activity of biomimetic diamond nanocone surfaces," Biointerphases 11, 011014, 6 pages (2016).
Green, et al., "High Quality Bioreplication of Intricate Nanostructures from a Fragile Gecko Skin Surface with Bactericidal Properties," Scientific Reports 7, 41023, 12 pages (2017).
Ito, et al., "Materials for enhancing cell adhesion by immobilization of cell-adhesive peptide," Journal of Biomedical Materials Research 25(11), pp. 1325-1337 (1991).
Nowlin, et al., "Adhesion-dependent rupturing of *Saccharomyces cerevisiae* on biological antimicrobial nanostructured surfaces," Journal of the Royal Society Interface 12(102), 12 pages (2014).
Jain, et al., "Using Chemoattractants to Lure Bacteria to Contact-Killing Surfaces," Angewandte Chemie 55(19), pp. 5698-5702 (2016).
Rasaili, et al., "Comparison of Ferromagnetic Materials: Past Work, Recent Trends, and Applications," Condensed Matter 7(12), 20 pages (2002).

\* cited by examiner (a)

(b)

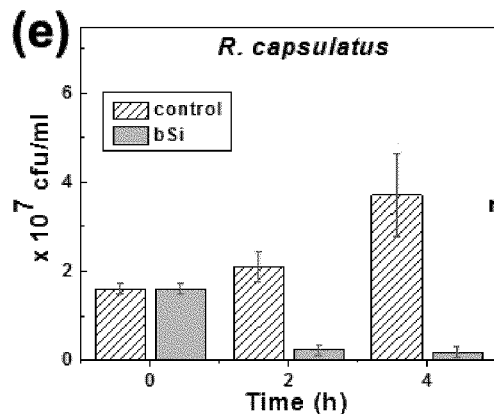
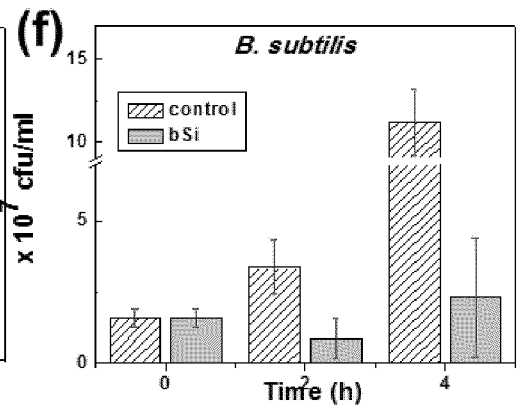
FIG. 9E    FIG. 9F
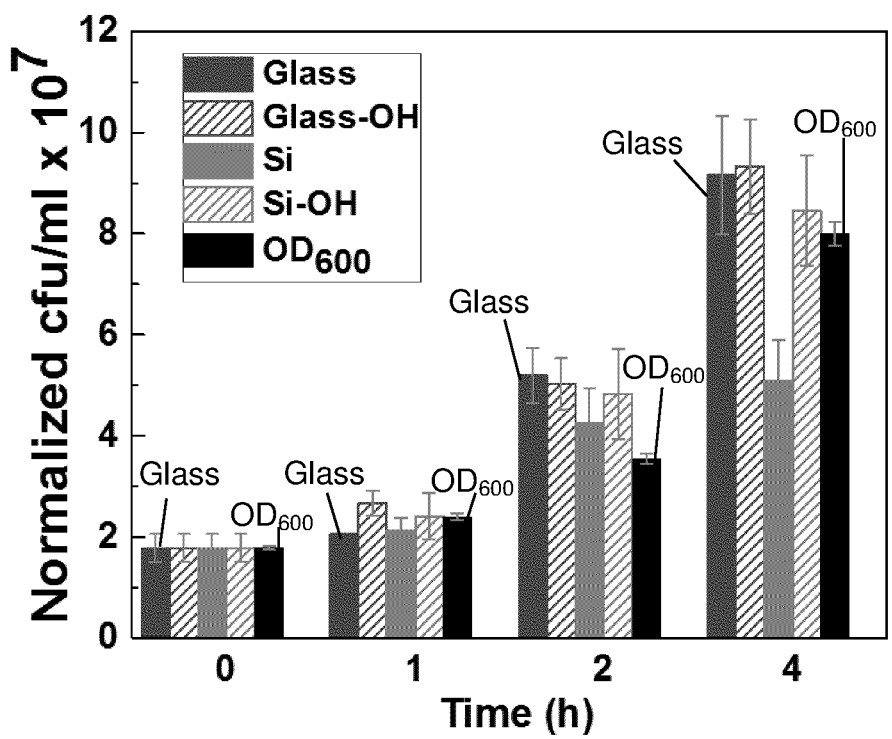
FIG. 10

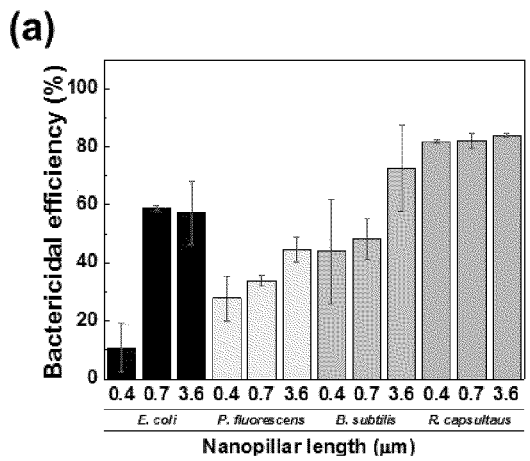
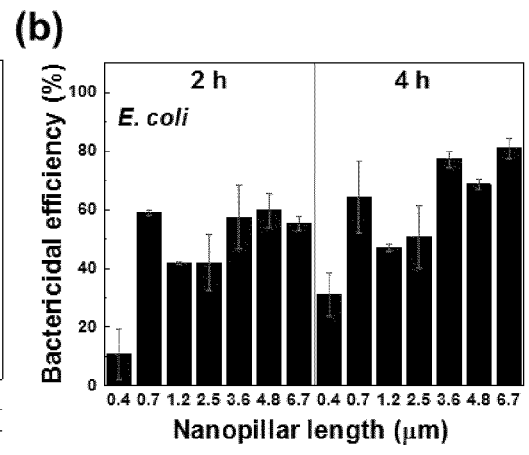
FIG. 13A
FIG. 13B
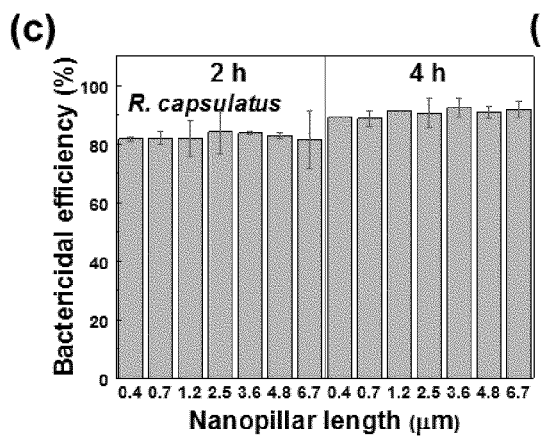
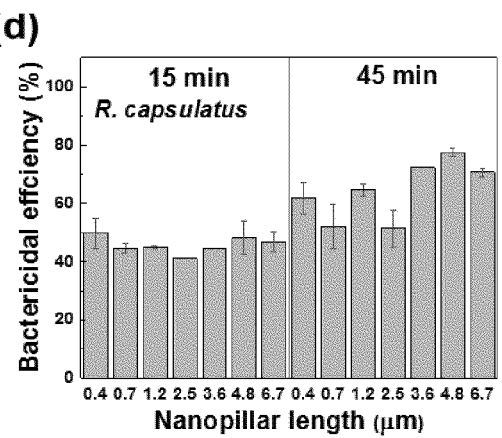
FIG. 13C
FIG. 13D

Blunt and short    Sharp and long

Blunt and short    Sharp and long

TUNABLE NANOTEXTURED MATERIALS

CROSS-REFERENCE TO RELATED APPLICATIONS

This applications claims benefit of U.S. Provisional Patent Application No. 62/562,244 filed Sep. 22, 2017 and U.S. Provisional Patent Application No. 62/690,212 filed Jun. 26, 2018, the contents of which are incorporated herein by reference in its entirety.

STATEMENT OF GOVERNMENT INTEREST

This invention was made with government support under Contract No. DE-AC02-06CH11357 awarded by the United States Department of Energy to UChicago Argonne, LLC, operator of Argonne National Laboratory. The government has certain rights in the invention.

TECHNICAL FIELD

The present disclosure relates generally to antimicrobial materials.

BACKGROUND

Novel biomaterials are being used increasingly in the improvement of health care. Unfortunately, protecting the surfaces of these materials from colonization by microorganisms that can form biofilms remains a challenge, consequently limiting the range of their application. Biofilms are communities of microorganisms encased in an intercellular matrix made of extracellular polymeric substances that form an interface between the cells and the environment. In some cases, when the environment changes, a reorganization of the matrix is observed and allows for the biofilm to adapt to the new surroundings, rendering its resistance to antiseptic agents, for instance.

Bacteria tend to foul any surface where water is present. This tendency is not only potentially harmful to patients with abiotic implants but is also problematic for accessories and equipment as the bacteria and biofilms clog pumps and tubes. Their effects are broad reaching beyond medicine, ultimately affecting all industries like food processing or paper manufacturing.

Additionally, the emergence of multi-drug-resistant bacteria—those that cannot be eliminated by treatment with antibiotics (or cocktails of antibiotics)—have urgently prompted the research community to search for novel strategies to prevent and/or effectively eliminate microbial colonization.

Generally, there are two approaches to combatting microbes that rely on chemical and/or physical interactions with the cells. In the chemical approach, surface coatings or solutions containing antibiotics, polymers, or metal and metal-oxide (nano)particles (like Cu—, ZnO- and Ag-based) are used. However, use of antibiotics brings a threat of evolving more multi-resistant strains, and additionally, the development of new antibiotics is a very slow and inefficient process. Furthermore, toxicity of unbound nanoparticles and their accumulation in human tissue is an ongoing problem.

During the last decade, the development of nanotechnology has offered alternative approaches to combat microbes that rely on chemical and/or physical interactions with bacteria. Antimicrobial activities of metal and metal-oxide nanoparticles (like Cu—, ZnO- and Ag-based), graphene, carbon nanotubes and their composites have been intensively investigated The mechanisms underlying their mode of action range from ions release to reactive ion species ("ROS") production to the irreversible physical damage imposed to bacterial membranes when the nanostructures introduce sharp edges.

Recently, surfaces that mimic, or attempt to mimic naturally occurring materials have been considered, known as "biomimetic" or in the alternative. Such biomimetic surfaces exhibiting nanoscale topologies have gained a lot of attention. Such materials—including black silicon ("bSi"), patterned titanium nanowires, nanotextured polymer, and silicon nanowire arrays—contain nanopillars with dimensions and spacing similar to that of the waxy protrusions on plants and insect wings (e.g., cicada, dragonfly; as well as skin of shark and feet of geckos; and others from animal kingdom), responsible for keeping these surfaces free of microbes (anti-biofouling; reviewed by Nguyen, et al.). Hence, they are commonly called cicada wings-like nanostructures ("CWLN"). Among all of these, bSi is extremely promising as it exhibits selective bactericidal activity while supporting growth and proliferation of much larger eukaryotic cells. In addition to the hallmarked use of bSi in bactericidal coatings, bSi has been demonstrated to be suitable for numerous applications like sensors, photonic devices, (nano)micro-electromechanical structures ("NEMS/MEMS").

Several methods can be employed to fabricate bSi. Reactive-ion etching ("RIE") is a scalable and cost-effective technique, during which bSi topographical features can be modulated by varying process conditions such as gas composition and flow rate, temperature, etching time, pressure, substrate bias, and RF power. Metal-assisted chemical etching is a viable alternative with the potential for finer control of the resulting surface topography but requires more fabrication steps that may limit wide-scale application. Laser irradiation is a newer technique that is beginning to be applied and holds promise for precise control of patterning at, potentially, the expense of scalability.

To be used as an effective antimicrobial agent, bSi, or any CWLN material needs to act on the wide range of chemical and mechanical properties displayed by bacterial cell envelopes in nature. These rough surfaces of CWLN materials act using at least two mechanisms: sticking to a surface and impacted by attractive forces or undergoing direct physical penetration. The suspended body between the spikes eventually ruptures, killing the organism, when stress on the outer membrane and cell wall reaches a stretching threshold.

Consequently, natural and biomimetic CWLN-mediated cell killing is expected to depend on the nature of the cell envelope and vary across bacterial species. Indeed, differences in bactericidal efficacy of bSi as well as dragonfly wings (*D. bipunctata*) towards Gram-negative and Gram-positive bacteria have been shown.

The challenge for the materials community is the design of CWLN-mimicking antimicrobial structures that are feasible to fabricate and that allow for tunable properties, for example selective targeting of a spectrum of species as broad as possible or alternatively selectively kill a specific microorganism.

SUMMARY

One embodiment relates to a nanotextured material. The nanotextured material has a substrate having a plurality of nanopillars extending there from. Each of the plurality of nanopillars has a narrowed tip opposite the substrate. Wherein the nanotextured material has a water contact angle of no greater than 20°.

Another embodiment relates to a nanotextured material comprising a substrate having a plurality of nanopillars extending there from with a density on the substrate of 26 pillars per $\mu m^2$ to 2 pillars per $\mu m^2$. Each of the plurality of nanopillars has a nanopillar lengths between 0.39 to 7 μm and a nanopillars diameter is from 50 nm to 490 nm. Each of the plurality of nanopillars further has a tip opposite the substrate, the tip having a tapering diameter with a tip angle of 45° to 10°. Wherein the naotextured material has a water contact angle of no greater than 20°.

It should be appreciated that all combinations of the foregoing concepts and additional concepts discussed in greater detail below (provided such concepts are not mutually inconsistent) are contemplated as being part of the subject matter disclosed herein. In particular, all combinations of claimed subject matter appearing at the end of this disclosure are contemplated as being part of the subject matter disclosed herein.

BRIEF DESCRIPTION OF DRAWINGS

The foregoing and other features of the present disclosure will become more fully apparent from the following description and appended claims, taken in conjunction with the accompanying drawings. Understanding that these drawings depict only several implementations in accordance with the disclosure and are, therefore, not to be considered limiting of its scope, the disclosure will be described with additional specificity and detail through use of the accompanying drawings.

FIG. 3A is a photograph of the etched 4" wafer after 15 min plasma exposure. FIGS. 3B, 3C, and 3E-I are SEM micrographs presenting the nanotopography of black silicon fabricated using a range of etching times: FIGS. 3B-C 3 min, FIGS. 3E-F 10 min, and FIGS. 3G-I 15 min.

FIGS. 3B, 3E, and 3H show cross sections with insets presenting a magnified view of the tips, and FIGS. 3C, 3F, 3G, and 3I show top views of etched surfaces. FIG. 3D is a schematic representation of the pillars where L is total length, $L_{tip}$ is a length of sharpened tip, d is base diameter, and pitch is a distance between centers of two pillars (spacing+diameter). Scale bars are conserved at 1 μm in all images, except FIG. 3A 2.5 cm, and FIG. 3G 100 nm, and insets of FIGS. 3B, 3E, and 3H 400 nm.

$$\alpha = 2 \cdot \arctan\left(\frac{r}{L_{tip}}\right)$$

based upon the radius (r) and measured tip length ($L_{tip}$) of the nanopillars.

Figure 6:
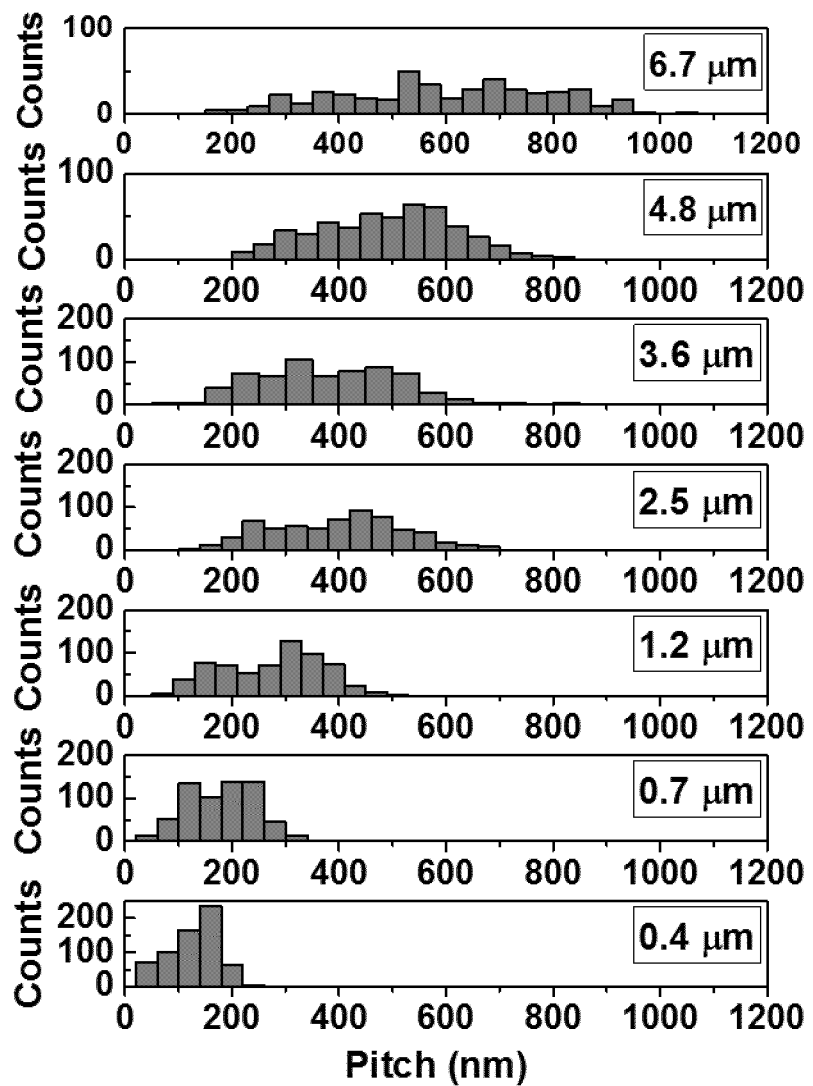

FIG. 6 shows distributions of nanopillar pitches for black silicon fabricated for 1.5, 3, 5, 10, 15, 20 and 30 min (bottom to top) that correspond to nanopillar lengths of 0.4, 0.7, 1.2, 2.5, 3.6 4.8, and 6.7 μm, respectively. Pitch is the distance between two spikes at the closest proximity (pitch=spacing+ base diameter) as diagrammed on FIG. 3D.

Figure 7A:
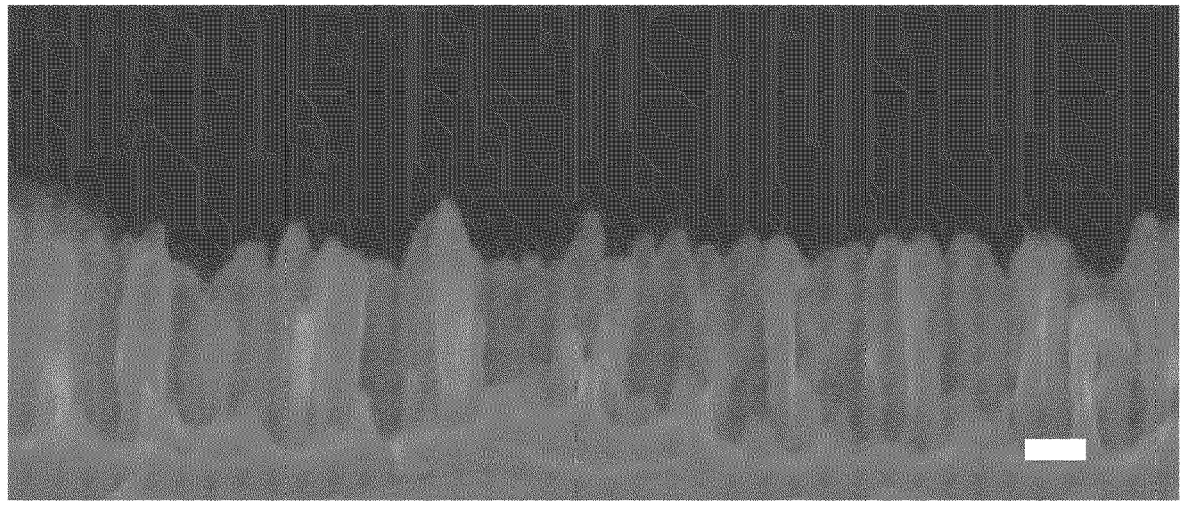
Figure 7B:
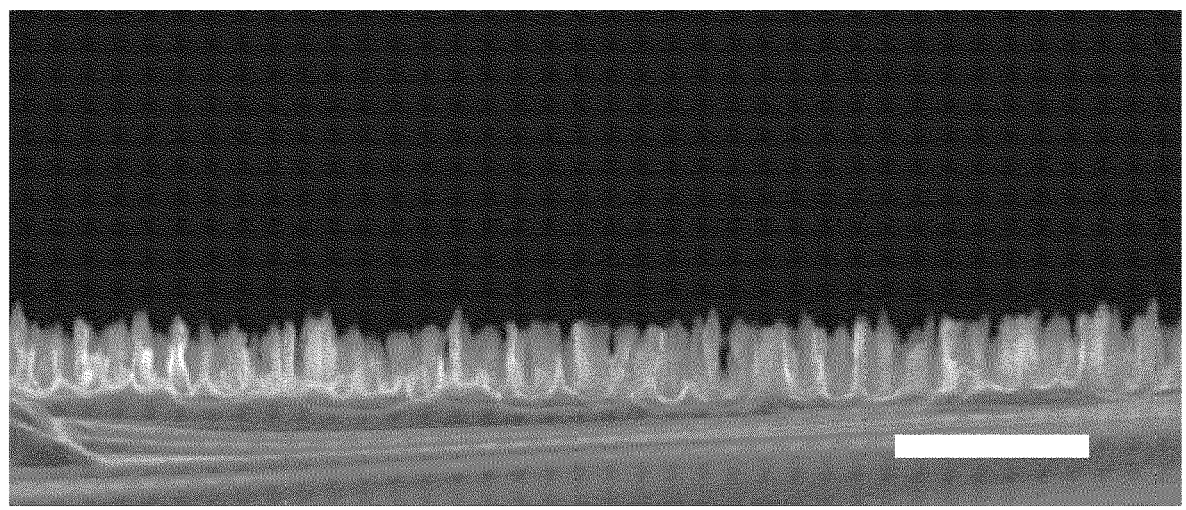

FIGS. 7A-B show SEM images of bSi etched for 1.5 min. The average nanopillar length is 390 nm (Table 1). FIG. 7A utilizes scale bars of 100 nm (top). FIG. 7B utilizes scale bars of 1 μm (bottom).

Figure 8A:
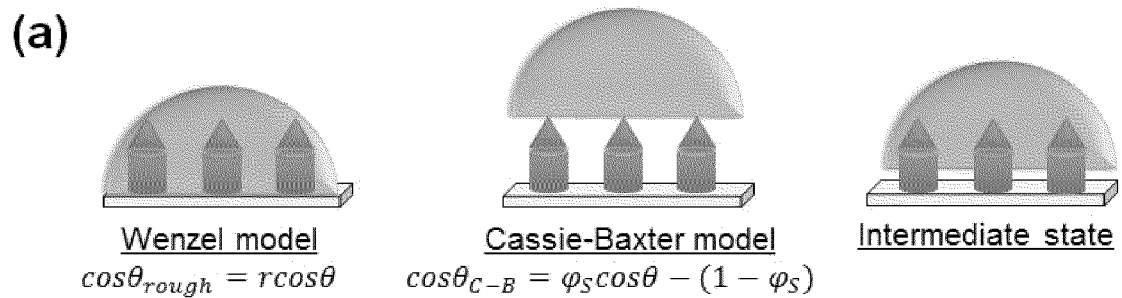
Figure 8B:
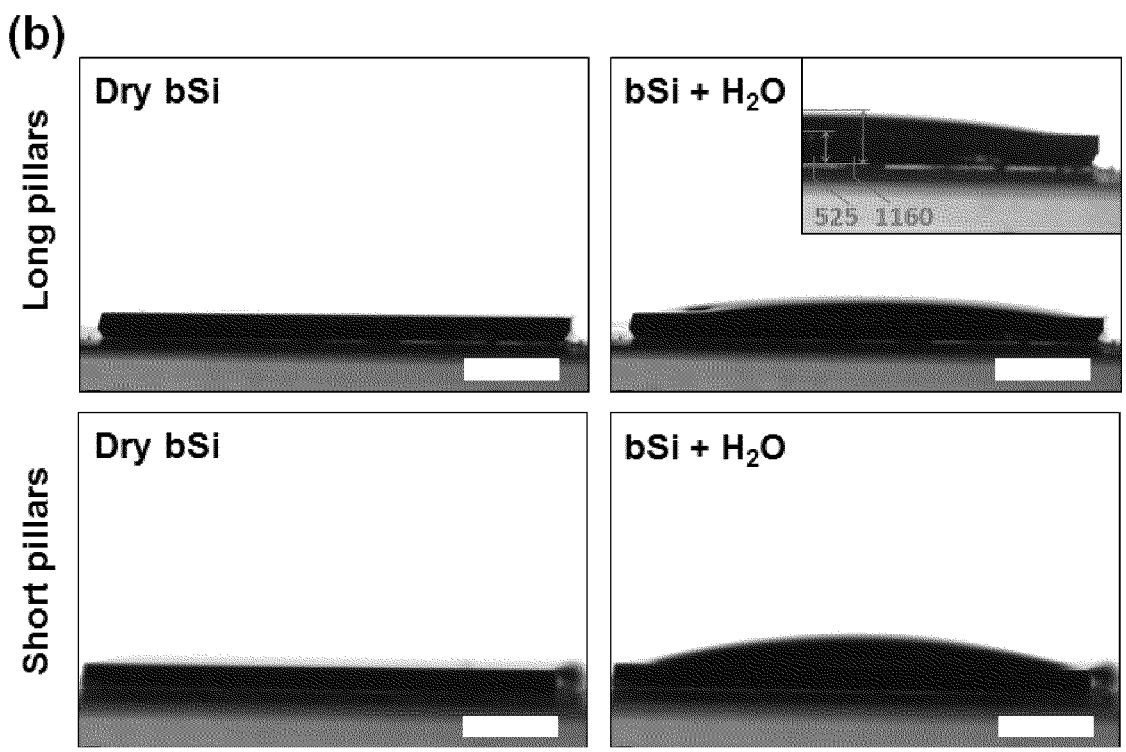

FIGS. 8A-B are a graphic representation of water droplet behavior. Where FIG. 8A (left panel) shows a Wenzel model, FIG. 8A (center panel) a Cassie-Baxter ("C-B") model, and FIG. 8A (right panel) an intermediate state. The equations describe the Wenzel model, where θ is the Young's contact angle on the flat surface and r is roughness, and the C-B model, where θ is the Young's contact angle on the flat surface and $\varphi_s$ is the fraction of the liquid's base in contact with the solid surface. FIG. 8B shows a series of lateral images of black silicon before and after the deposition of 20 μl of $H_2O$. Upper and lower rows correspond to bSi with long and short pillars, respectively. Scale bars are 2 mm. The inset presents a magnified view of droplet on the superhydrophilic surface. The wafer thickness and maximum meniscus height are given in μm.

Figure 9A:
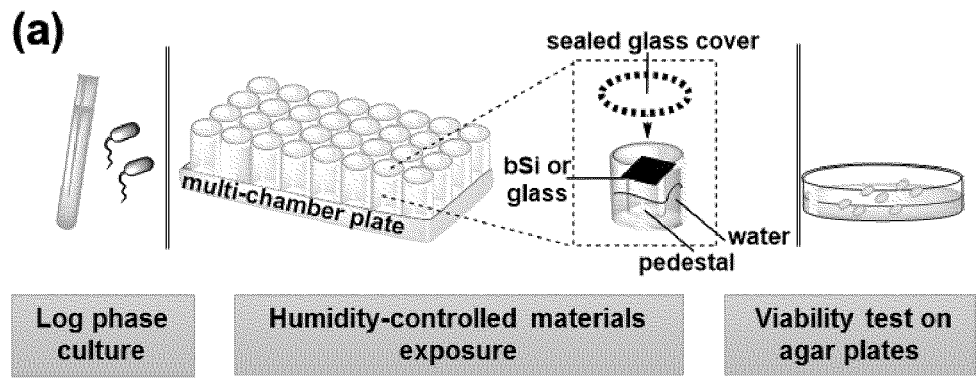
Figure 9B:
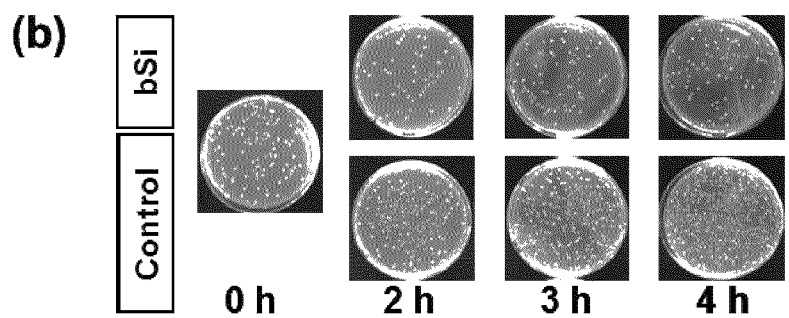

FIGS. 9A-F show bacteria viability on black silicon surface. FIG. 9A shows schematics of experimental workflow. FIG. 9B shows colony forming units are measured by plating on LB agar medium E. coli cells exposed to etched (bSi) and smooth (control) surfaces for various times. FIGS. 9C-F show bactericidal effect of bSi on four different bacterial species in rich medium at room temperature. Whereas cells multiply on a smooth surface, cell killing or growth inhibition is observed on nanostructured surfaces. The values are expressed as mean±SD (n=3 independent experiments).

FIG. 10 is a graph of growth of E. coli on various control surfaces, including silicon wafers (Si), air-plasma treated silicon wafers (Si—OH), glass cover slides (glass), and air-plasma treated glass cover slides (glass-OH), versus cells in static liquid culture (prepared in microfuge tubes with turbidity measured as $OD_{600}$ values). Surface studies commenced when 20 μl droplets ($1.6\times10^7$ cfu/ml) were placed on the control surfaces and incubated in the humidity-controlled reaction chambers (FIG. 9A) at RT.

Figure 11:
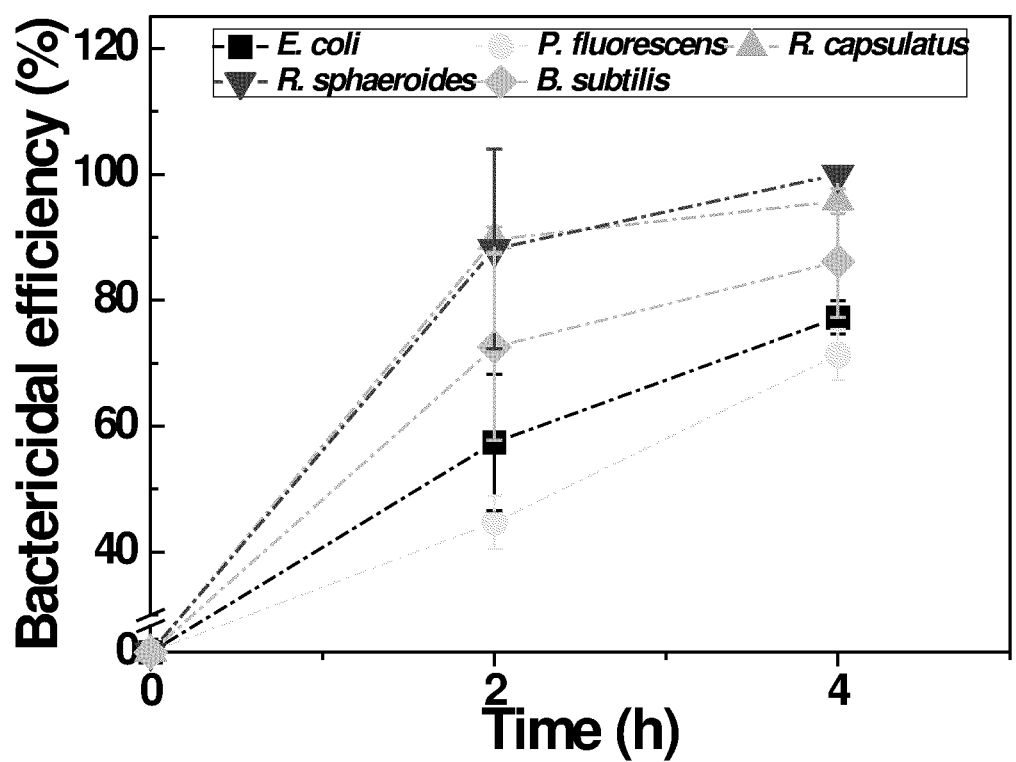

FIG. 11 shows bactericidal efficiencies of black silicon towards various Gram-negative bacteria species. Cells (20 μl; $1.6\times10^7$ cfu/ml) were incubated in rich medium at room temperature on black silicon and smooth control surfaces for 2 and 4 h. The values are presented as a % of control. The values are expressed as mean±SD (n=3 independent experiments). Is it possible to show intermediate points (e.g., for 1 and 3 hours).

Figure 12:
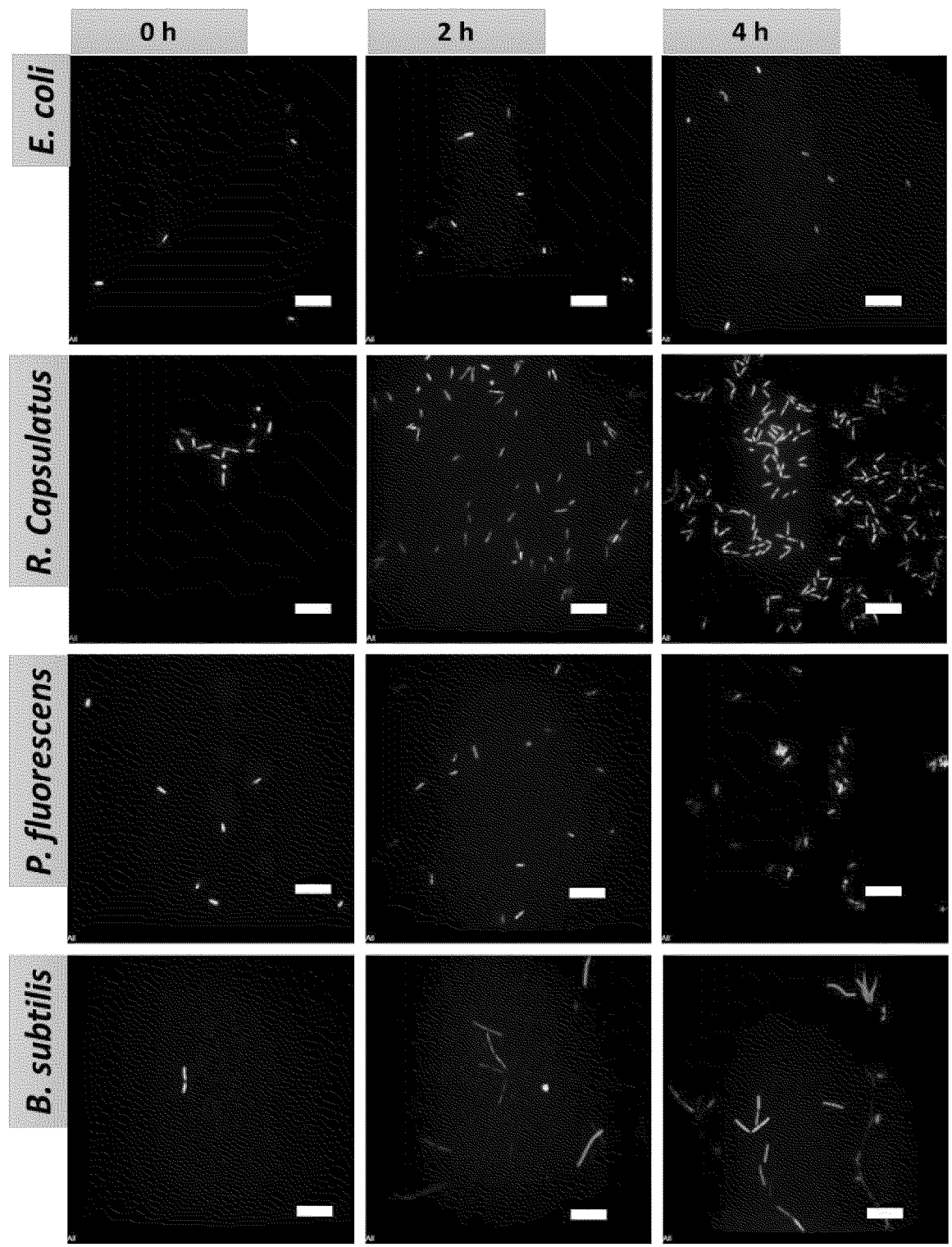

FIG. 12 includes confocal microscopic images of E. coli, R. capsulatus, P. fluorescens and B. subtilis attached to the surface of bSi at 0, 2 and 4 h of incubation. Cells were stained with LIVE/DEAD® BacLight™ Bacterial Viability Kit where green (lighter) and red dyes (darker) label live and dead cells, respectively. Scale bar is 10 μm.

FIGS. 13A-D show bactericidal efficiencies of black silicon of various nanopillar lengths towards E. coli and R. capsulatus. Bacteria (20 μl; $1.6\times10^7$ cfu/ml) were incubated in rich medium at room temperature on black silicon and smooth control surfaces for FIGS. 13A-B 2 and 4 h, and FIG. 13C for 15 and 45 min. The values are presented as a % of control. The values are expressed as mean±SD (n=3 independent experiments). Here, in FIG. 13A nanopillars, but in FIGS. 6B-C, spikes. If it is BE vs pillar length for 2 values of time, then time can be a label on each subplot, and x-label is just pillar length.

Figure 14:
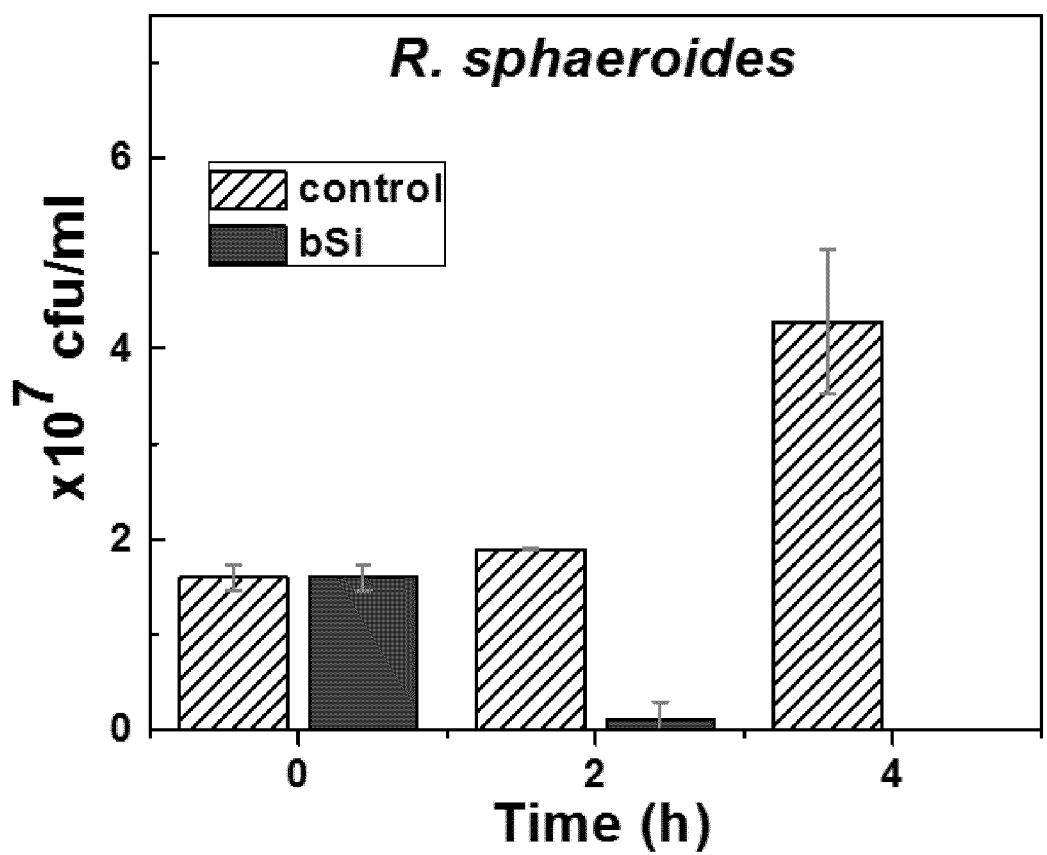

FIG. 14 illustrates the viability of *R. sphaeroides* on the benchmark, black-silicon surface. Colony forming units were measured by plating on $^G$YCC agar medium after exposure to etched (bSi) and smooth (control) surfaces in $^G$YCC for 2 or 4 h at room temperature. Cells clearly multiplied on the smooth surfaces whereas cells were killed or their growth inhibited on the nanostructured surfaces. The values are expressed as means±SD (n=3 independent experiments).

Figure 15:
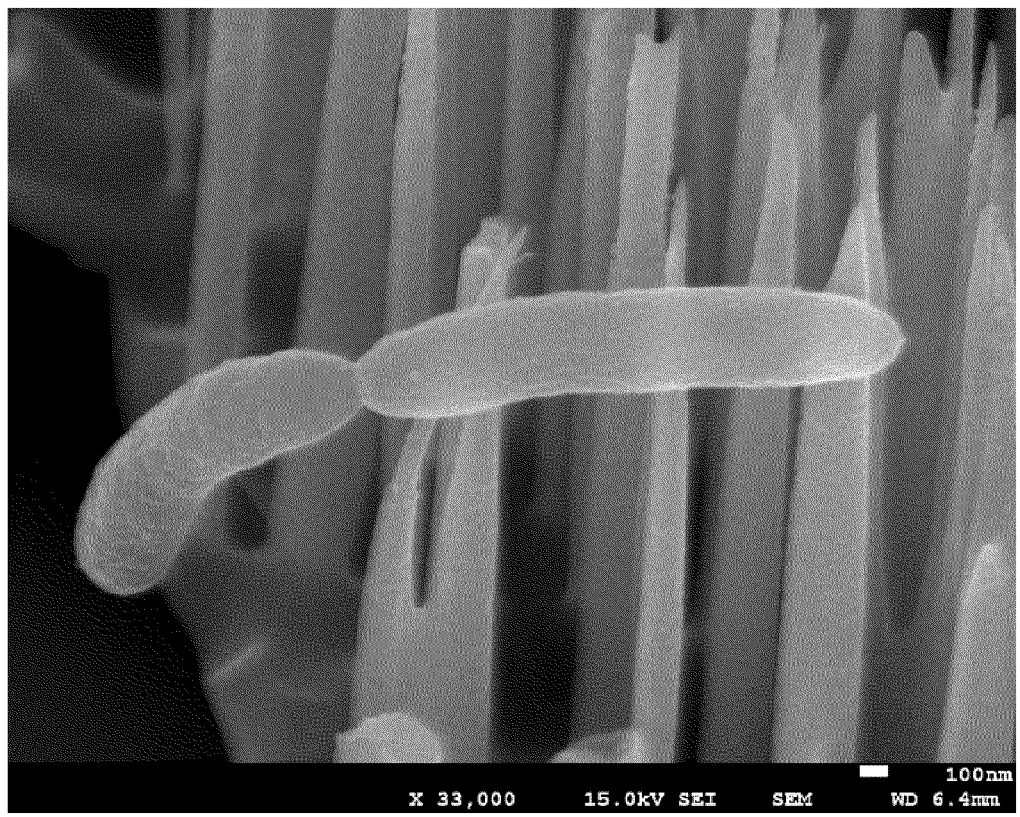

FIG. 15 illustrates an electron micrograph of a black silicon bactericidal material with 3.6 μm height nanopillars, about 3 nanopillars/μm$^2$, average pitch 380 nm (±130). Image magnification 33,000× (scale bar 100 nm).

Figure 16:
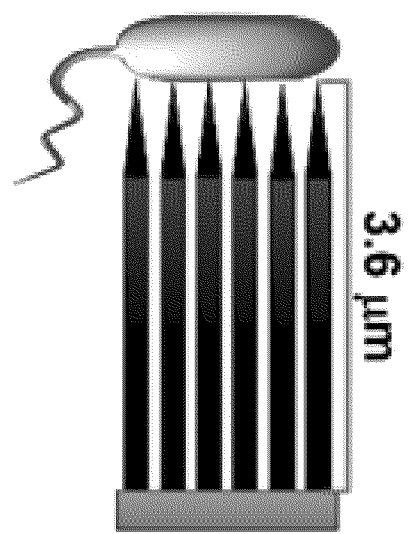

FIG. 16 illustrates the size of a bacterial cell relative to the nanopillar dimensions in FIG. 15.

Figure 17:
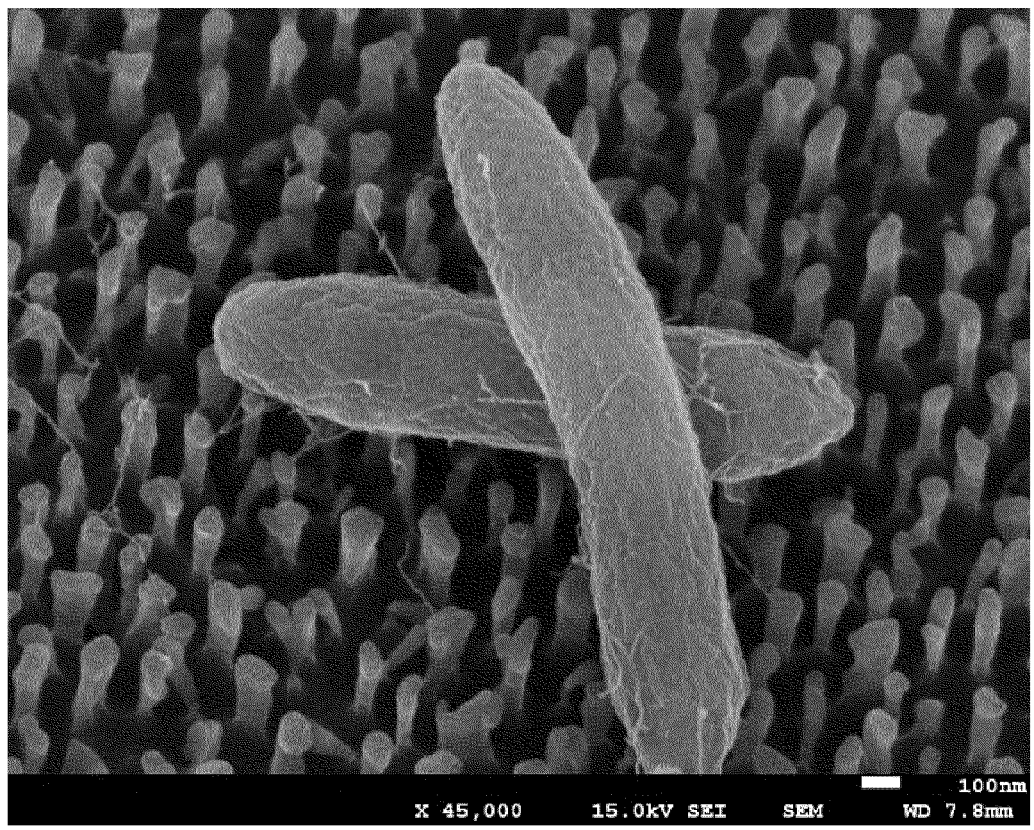

FIG. 17 illustrates an electron micrograph of a black silicon bactericidal material with 0.4 μm height nanopillars, ~27 nanopillars/μm$^2$, average pitch 130 nm (±40). Image magnification 45,000× (scale bar 100 nm).

Figure 18:
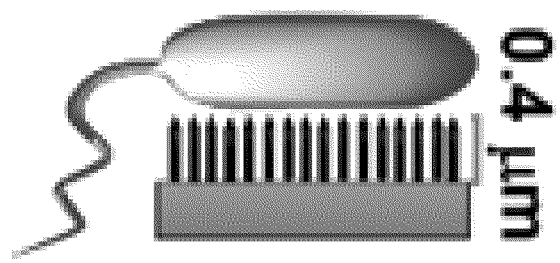

FIG. 18 illustrates the size of a bacterial cell relative to the nanopillar dimensions of FIG. 17.

Figures 19A, 19B:
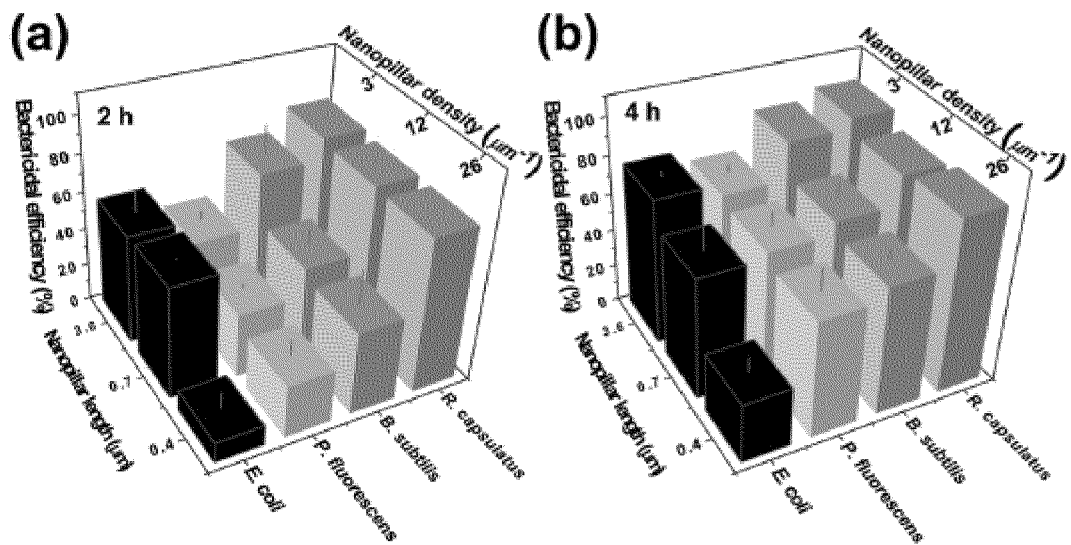
Figures 19C, 19D:
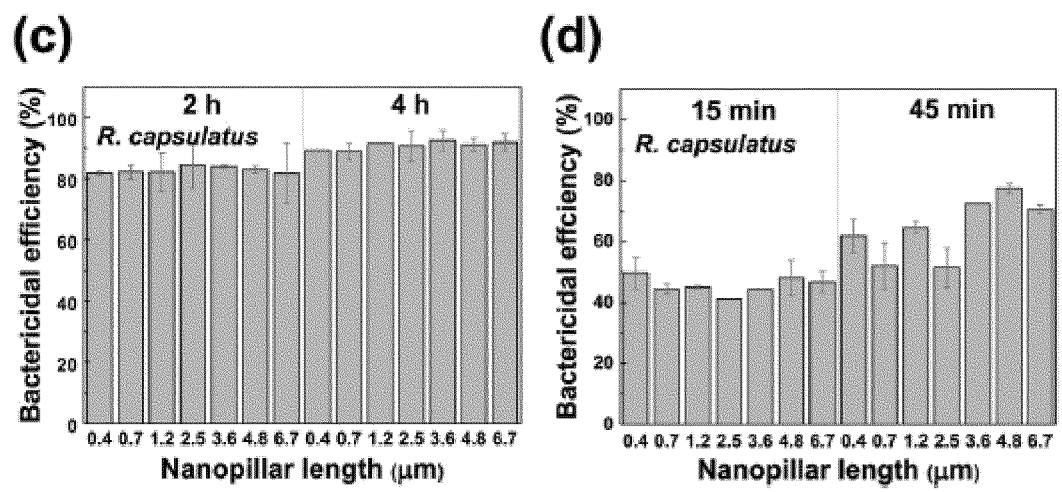

FIGS. 19A-D show bactericidal efficiencies of black silicon of three nanopillar lengths towards four genera with 2 h (FIG. 19A) and 4 h (FIG. 19B) incubations. (FIGS. 19C-D) *R. capsulatus* for an expanded set of bSi surfaces (seven in total). Bacteria were incubated in rich medium at room temperature on black silicon and smooth control surfaces for 2 and 4 h (FIG. 19C) and for 15 and 45 min (FIG. 19D). The values are presented as a % of control and are expressed as a mean±SD (n=3 independent experiments).

Figure 20:
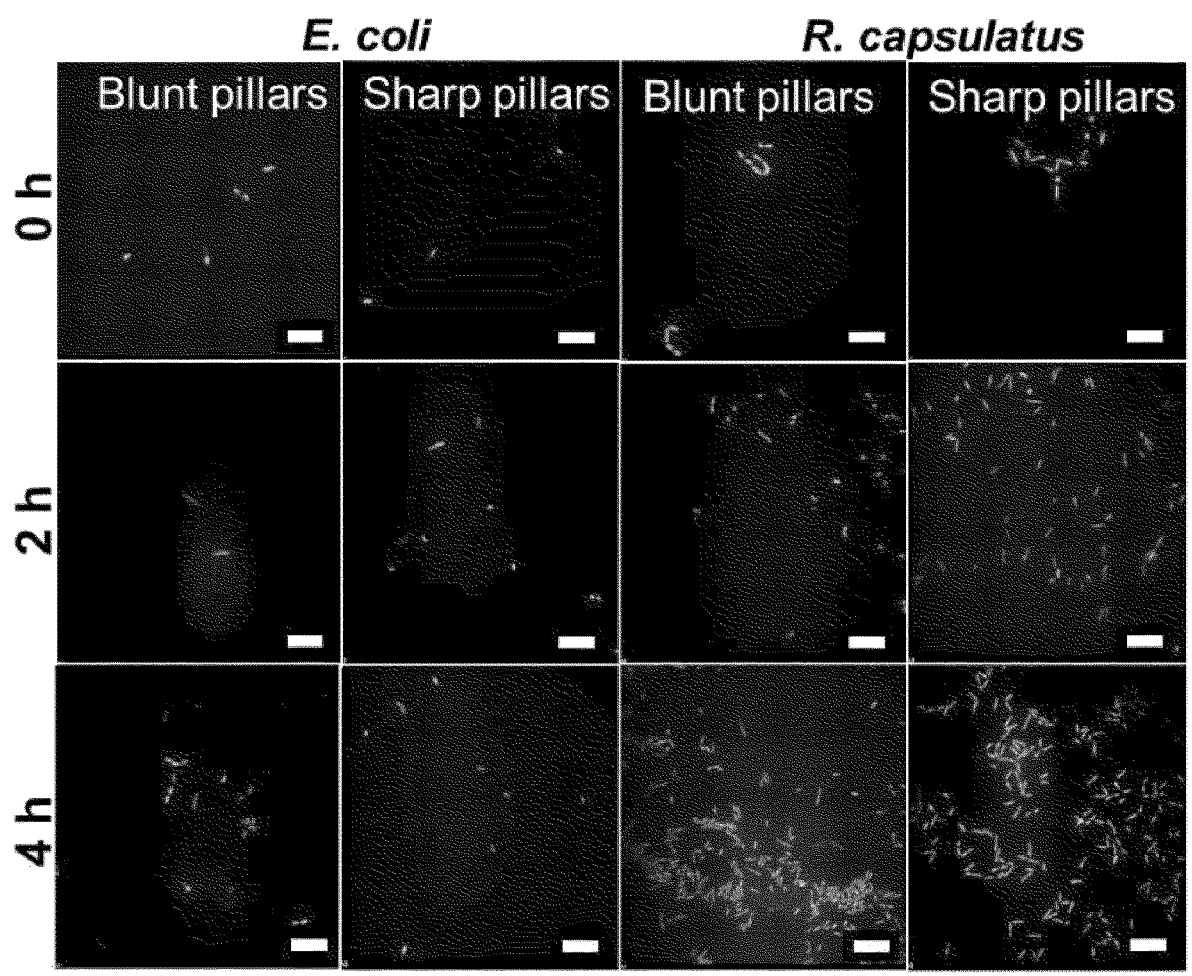

FIG. 20 is a series of confocal microscopy images of *E. coli* and *R. capsulatus* attached to the surface of bSi at 0, 2 and 4 h of incubation. Two surfaces were tested: 0.4 and 3.6 μm that correspond to blunt and sharp nanopillars. Cells were stained with a bacterial viability kit where green (lighter) and red dyes (darker) label live and dead cells, respectively. Scale bar is 10 μm.

Figure 21A:
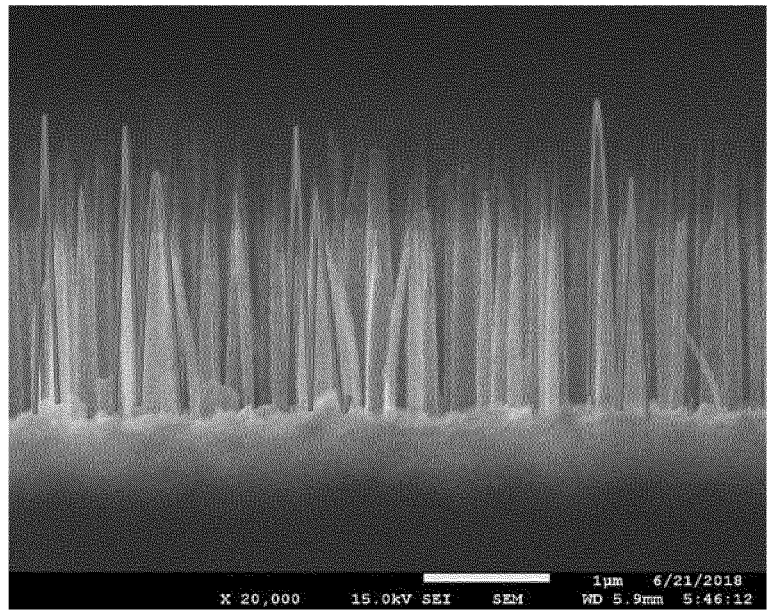
Figure 21B:
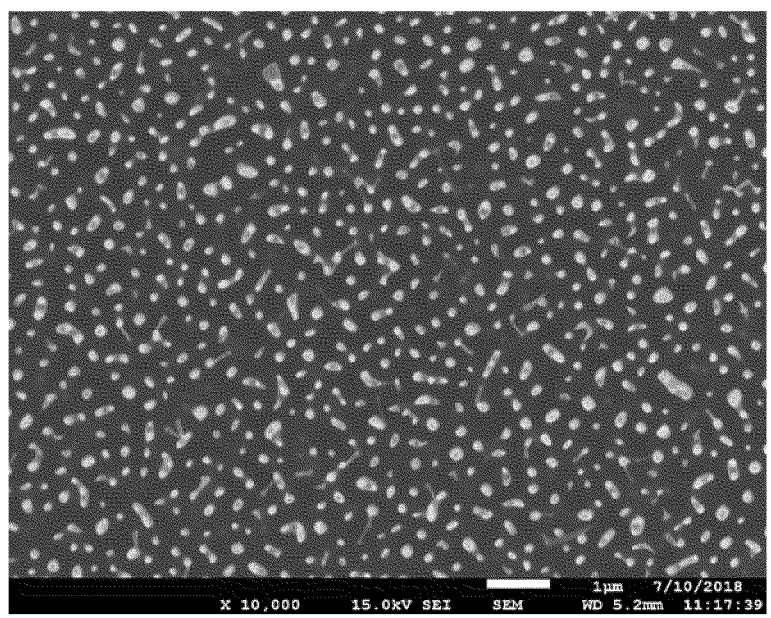

FIGS. 21A-B show etched silicon wafer at elevated temperature (25° C.) showing a heterogeneous rough surface displaying two lengths of nanopillars.

Figure 22:
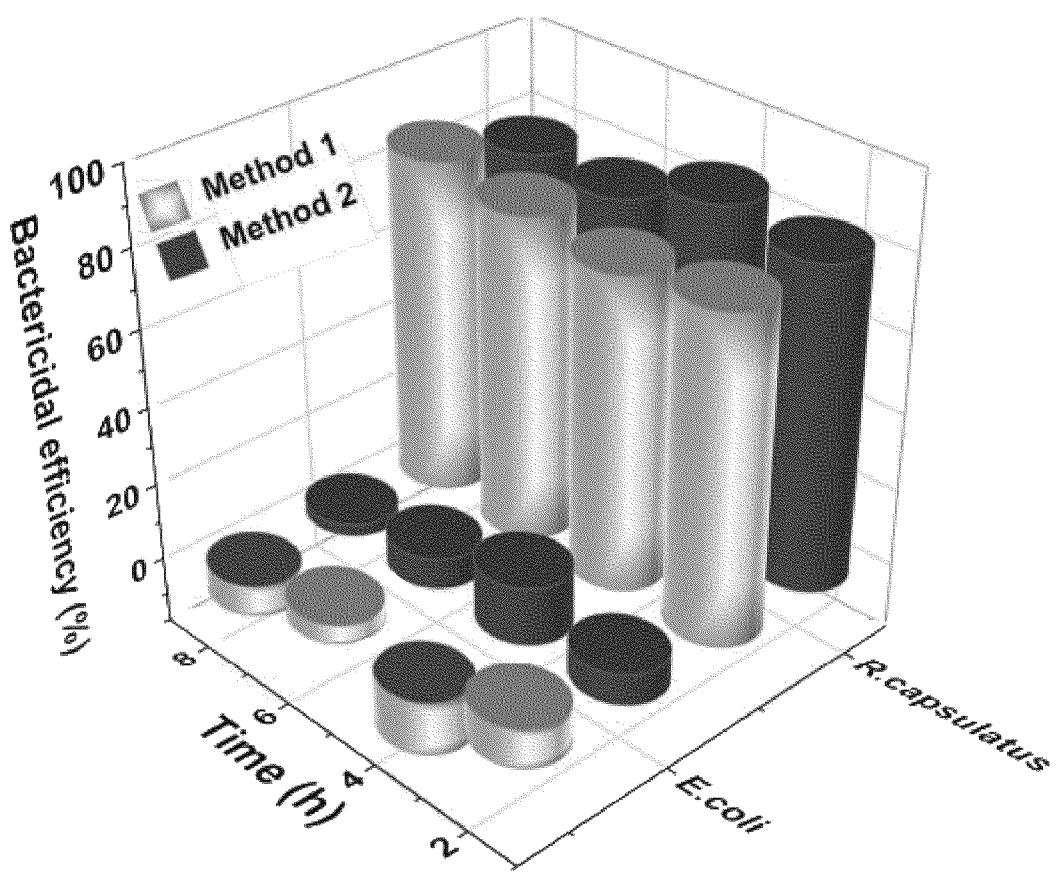

FIG. 22 is a graph comparing bactericidal efficiency as a function of time across the two example bacteria for both the plating method (Method 1) and the cytometry method (Method 2), illustrating proof of selectivity by bactericidal efficiency by two different methods with extended time of incubation.

Figure 23A:
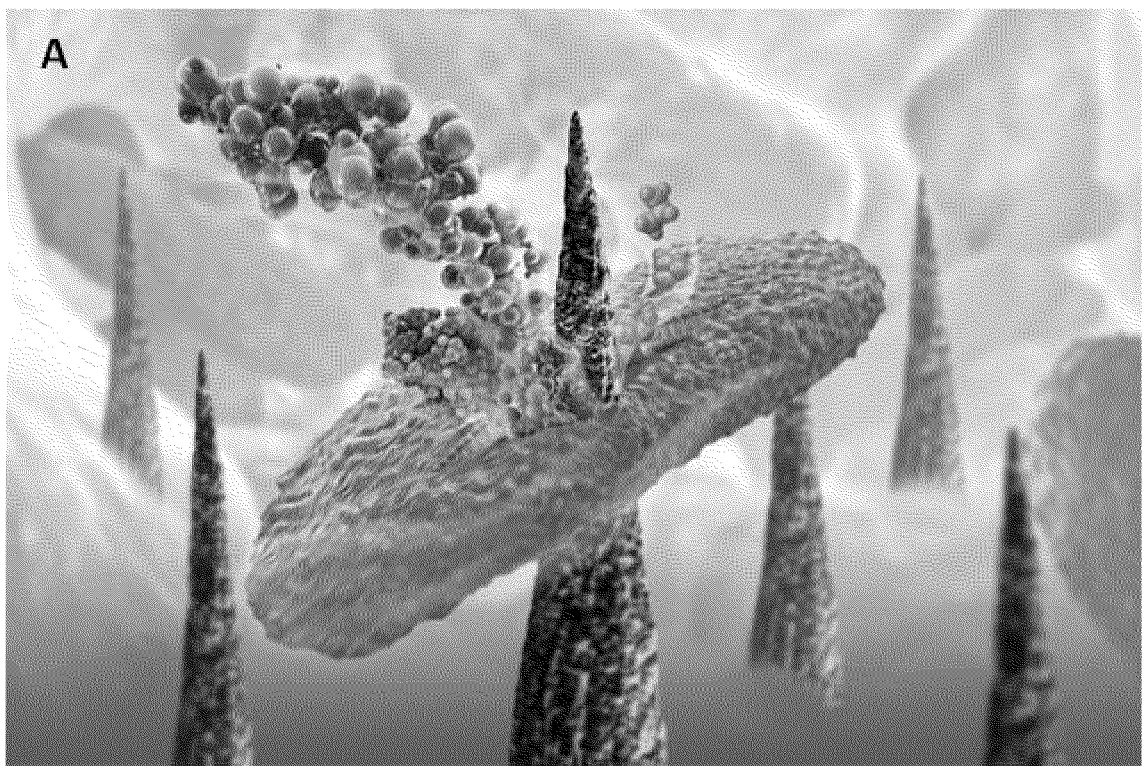
Figure 23B:
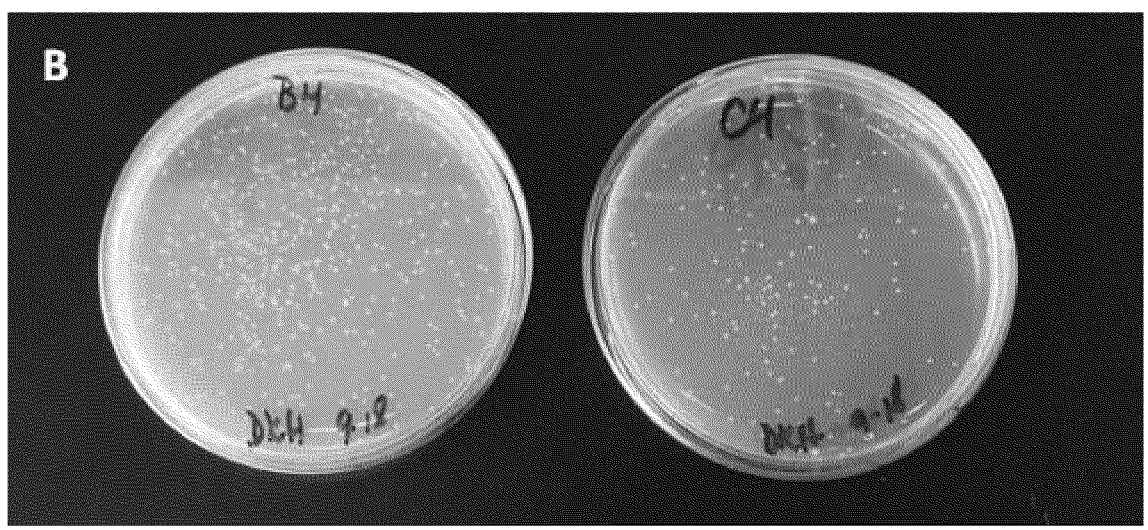

FIG. 23A is a schematic of an interaction of a bacterial cell with a single, sharp, sparse, "superkilling" nanopillar. The release of proteins, DNA, RNA, lipids, metabolites and other cellular components become possible at this stage. FIG. 23B is a photograph showing increased release of plasmid DNA from cells incubated for 4 hours on bSi (B4) relative to cells incubated on smooth control surfaces (C4), as measured through numbers of isolated colonies that resulted from transformation of chemically competent cells with aliquots of recovered cell suspension buffer (with cells removed).

Figure 24A:
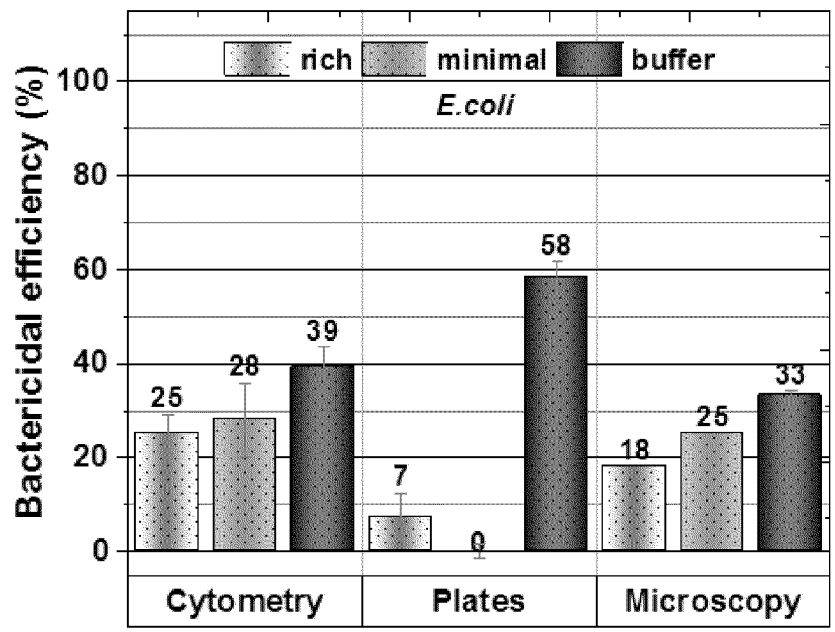
Figure 24B:
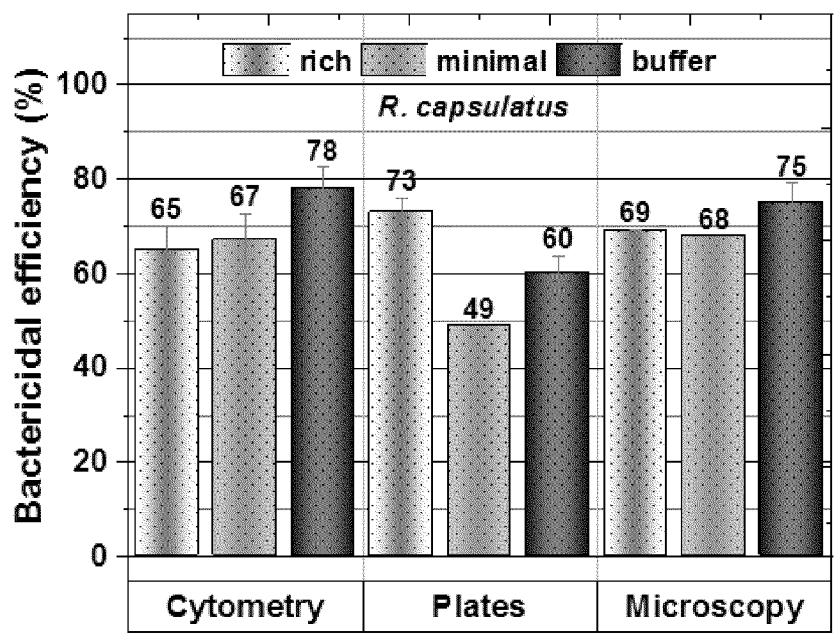
Figures 25A, 25B:
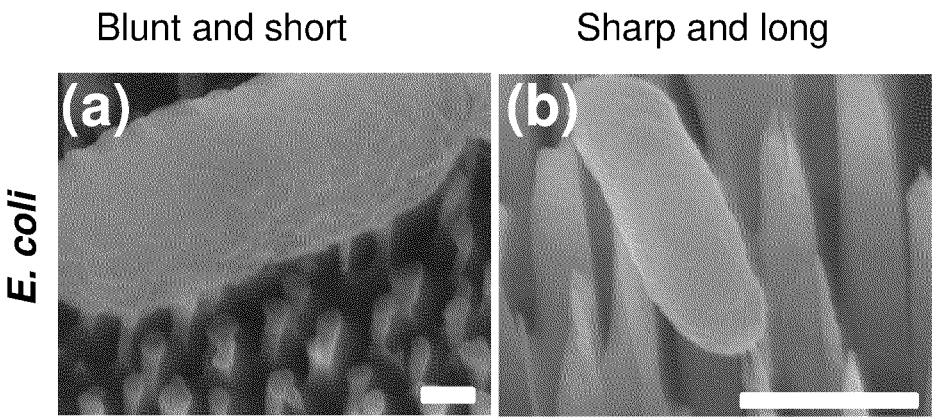
Figures 25C, 25D:
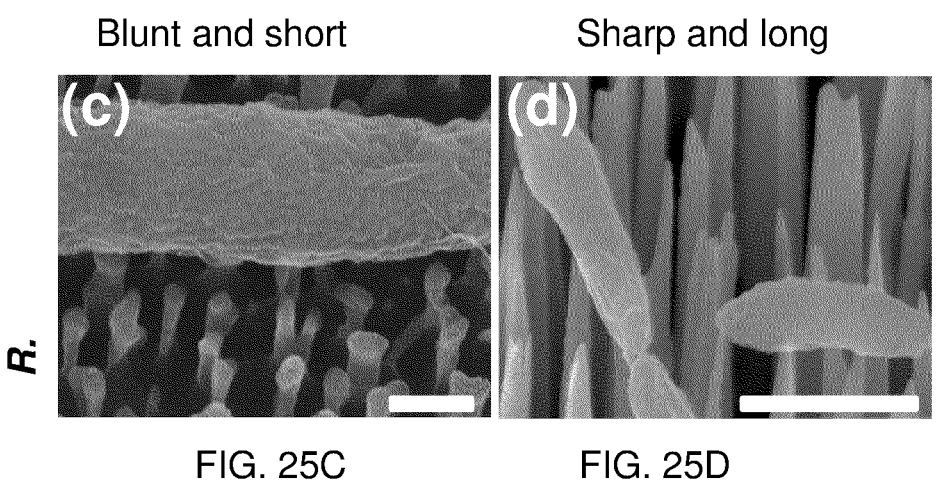

FIGS. 24A-B show bactericidal efficiencies of etched silicon (L=390 nm) towards *E. coli* (FIG. 24A) and *R. capsulatus* (FIG. 24B).

FIGS. 25A-D are SEM micrographs of *E. coli* (top row) and *R. capsulatus* (bottom row) attached to black silicon surfaces: (FIGS. 25A, 25C) blunt and (FIGS. 25B, 25D) sharp nanopillars (samples: 0.4 and 3.6 μm, respectively). The images present two different mechanisms leading to cell death where only the sharp pillars can penetrate the cell body. Scale bars 500 nm. (FIGS. 25A, 25C) tilted 30°, (FIGS. 25B, 25D) tilted 45°.

Figure 26:
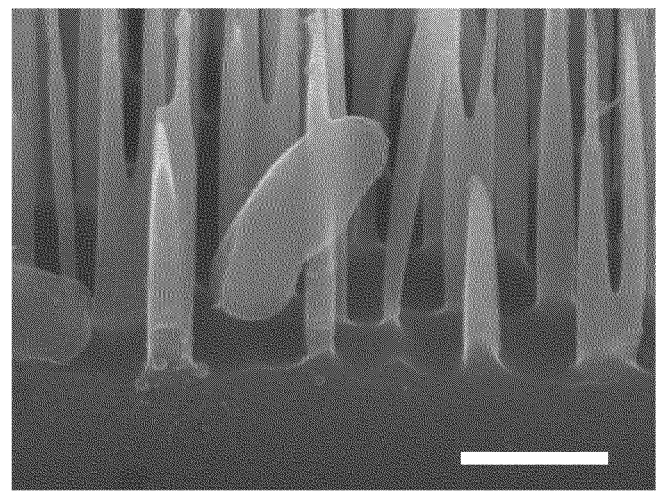

FIG. 26 is an SEM micrograph of *E. coli* with sharp nanopillar passing through. Scale bar 1 μm.

FIGS. 27A-F are SEM micrographs of *E. coli* (top row) and *R. capsulatus* (bottom row) attached onto smooth (FIGS. 27A-B) and black silicon surfaces: blunt (FIGS. 27C-D) and sharp (FIGS. 27E-F) nanopillars (samples: 0.4 and 3.6 μm, respectively). The red arrows indicate bacterial adhesins arranged around nanofeatures. Scale bars 500 nm. (FIGS. 27 A-D) tilted 30°, (FIGS. 27E-F) top views.

Figure 28:
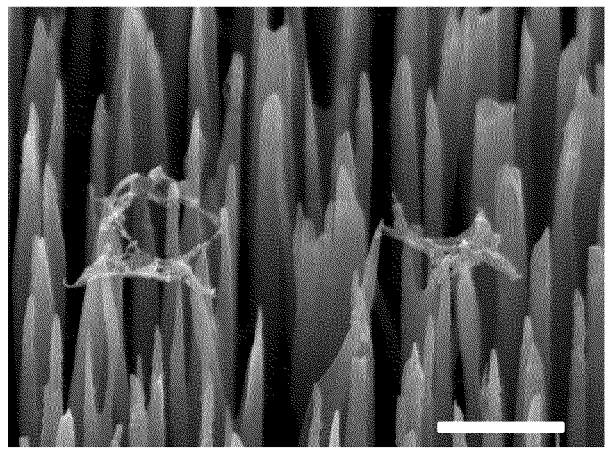

FIG. 28 is a SEM micrograph of cellular debris remained (or vanishing) after nanopillars-driven killing. The image indicates technology sustainability where the same surface is capable of interacting with another cell.

Figures 29A, 29B:
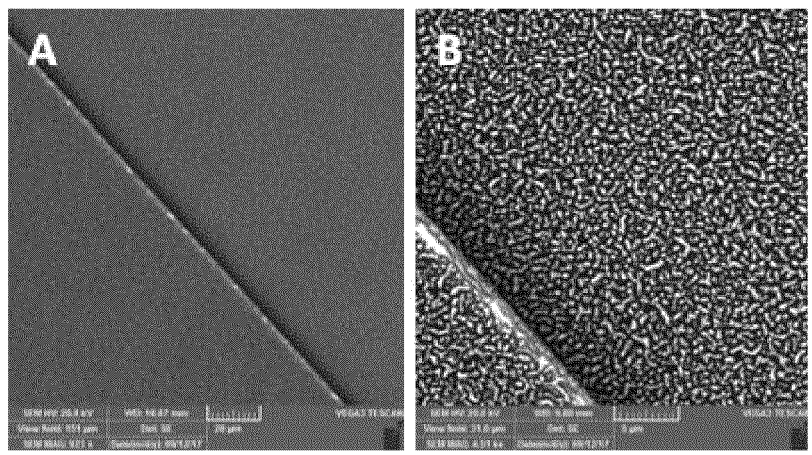
Figures 29C, 29D:
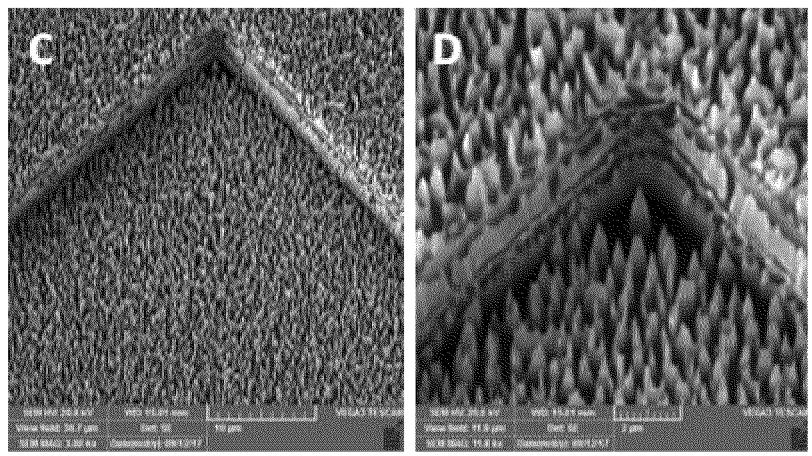
Figure 29E:
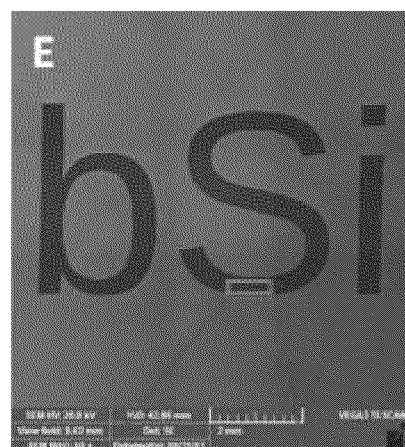
Figure 29F:
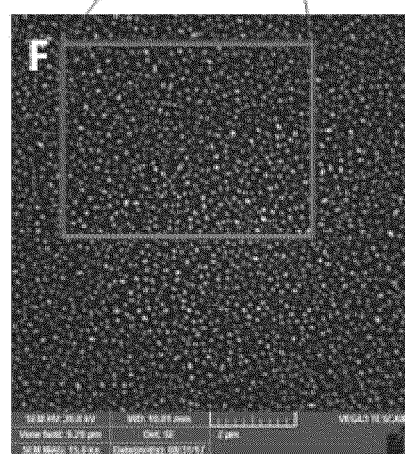
Figure 29G:
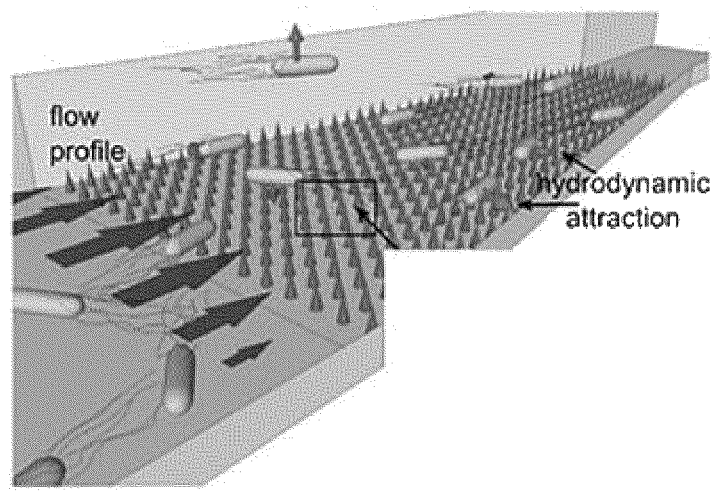

FIGS. 29A-G show an etched silicon wafer demonstrating the ability of a pattern, enabled by a chromium mask and lift-off approach, to protect surfaces. FIGS. 29A-B show two magnifications of the stepped edge where the mask was located and removed-half way through the etching cycle; FIGS. 29C-D two magnifications of a masked corner; FIG. 29E shows a lower magnification of the entire pattern on the silicon wafer; FIG. 29F shows a top view of the sharp needles found in an unmasked region; and FIG. 29G shows one concept for a microfluidic surface covered by black silicon that will be used in microfluidic devices for analytical assays.

Reference is made to the accompanying drawings throughout the following detailed description. In the drawings, similar symbols typically identify similar components, unless context dictates otherwise. The illustrative implementations described in the detailed description, drawings, and claims are not meant to be limiting. Other implementations may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

DETAILED DESCRIPTION OF VARIOUS EMBODIMENTS

Antimicrobial nanopatterning (texturing/roughness) represents a promising approach for protection of abiotic surfaces from microbial infection to colonization. Described herein are new forms of nanotextured (nanopatterned/nanorough) materials/substrates for devices/coatings where the featured properties of the nanopillars (nanospikes/nanoprtrusions/nanopencils/nanograss) can be reproducibly tuned to elicit differences in their bactericidal properties. As used herein, nanotextured materials shall refer to all such forms unless otherwise specified. Nanotextured shall mean the Nanotextured shall mean the material has regularly occurring nanometer-sized features and a Wenzel roughness above 1.3, in one embodiment with a surface roughness amplitude of at least 100 nm and a surface roughness frequency of at least 1 pillar per micrometer.

As used herein, antimicrobial selectivity means the relative kill rate for nanotextured materials with the defined range of properties with regard to one class of microbial organism compared to one or more other classes of microbial organisms, such as bactericidal selectivity where the organism is bacteria or prokaryotic vs. eukaryotic selectivity for such classes. As used herein, antifouling refers to the ability to reduce the growth of microorganisms, plants, algae, or animals on a surface.

Nanotextured materials exhibit "features" on the surface, the features being protrusions or aspects of the surface that provide the roughness. For example, a pillar can be a feature. FIG. 3D illustrates an example of a nanotextured material having a surface 210 with a plurality of pillars 220, which have a body portion 221 capped with a tip 222. The features of the nanotextured materials can be tuned to provide rough surfaces that vary by one or more of length, diameter, tip angle, pitch, shaft (core)/tip ratios, tip morphology, shaft morphology, pillar heterogeneity, pillar strength (mechanical stiffness), pillar porosity, pillar surface chemistry, pillar polarity, pillar doping, pillar connectivity, pillar electrical resistance, pillar base diameter, pillar concavity/convexity, and density. In one embodiment, the nanopillar lengths can be tuned in the range of 0.39-7 µm. In one embodiment, the nanopillar diameter can be tuned in the range of 50-490 nm. In one embodiment, the nanopillar tip angle can be tuned in the range of 45°-10°. In one embodiment, the nanotextured material can be fabricated with a nanopillar density of 26 pillars/µm$^2$ to 2 pillars/µm$^2$. In one embodiment, the nanopillar tips comprise from a maximum of 50% down to ~18% of the total nanopillar length (or range from 70 nm to 3 µm).

The nanotextured material may be formed from a wide range of materials, including. The nanotextured materials me be formed from hard materials such as, but not limited to: silicon, silicon with grown SiO2 layer, titanium, titania, Ti alloy, quartz, fused silica, zirconium, copper, aluminum or soft materials, such as but not limited to: polymers (non- and conductive; synthetic and natural; biodegradable and non) examples: PMMA, PEDOT, PS (polystyrene), chitosan, silk fibroin, alginate, PLA, amylopectine, polyimide, Parylene (poly(p-xylylene) polymers family). It should be appreciated that the nanotextured material may be a composite or hybrid material, including but not limited to, of two or more of the above specific materials. Further, the nanotextured material may be provided in a variety of form factors, including but not limited to, wafers, disks, foils, or the like. The nano textured material may also have nanotexturing on more than one side or face. For example, a wafer may have nanotexture features on both faces of the wafer, such features may be identical or different to provide either the same or different antimicrobial selectivity. For example, in one embodiment, silicon wafers are utilized to form the nanotextured material.

Fabrication and Nanotopography of Black Silicon

One embodiment of a nanotextured material formed from silicon material, utilizes black silicon (bSi). Black silicon fabrication may be carried out as known in the art, including by use of the ICP RIE technique. Using the ICP RIE process, bSI is fabricated as a no-masking process in O$_2$ and SF$_6$ atmosphere whereas a continuous competition between the etching fluorine radicals and the side-wall-passivating oxygen radicals occurs such as described in "Black Silicon: Fabrication Methods, Properties and Solar Energy Applications" (Liu, et al., *Energy Environ. Sci.* 7, 3223-3263 (2014)), incorporated herein by reference. In a further embodiment, the etched surfaces can be migrated over post-synthesis to another surfaces as the substrate to support the bSi material or can use nanoimprinting techniques to transfer the nanopillars to other types of materials that conform to unique surface structures. Further, the nanopillar surfaces can be coated with atomic layers (including partial layers, such as islands) of other metals or metal oxides. They can be readily surface modified for any exposed functionalization using silane chemistry. In addition, during the synthesis, wafers with different amounts of impurities/dopants can be used. For example, in some embodiments described further below, the nanopillar materials include boron. Impurities and thickness impact flexibility. For example, Regime 3 materials can be made hydrophobic by silanization with amino silanes. Regime 1 materials that are hydrophilic can be made super hydrophilic with acid etching.

Figure 1:
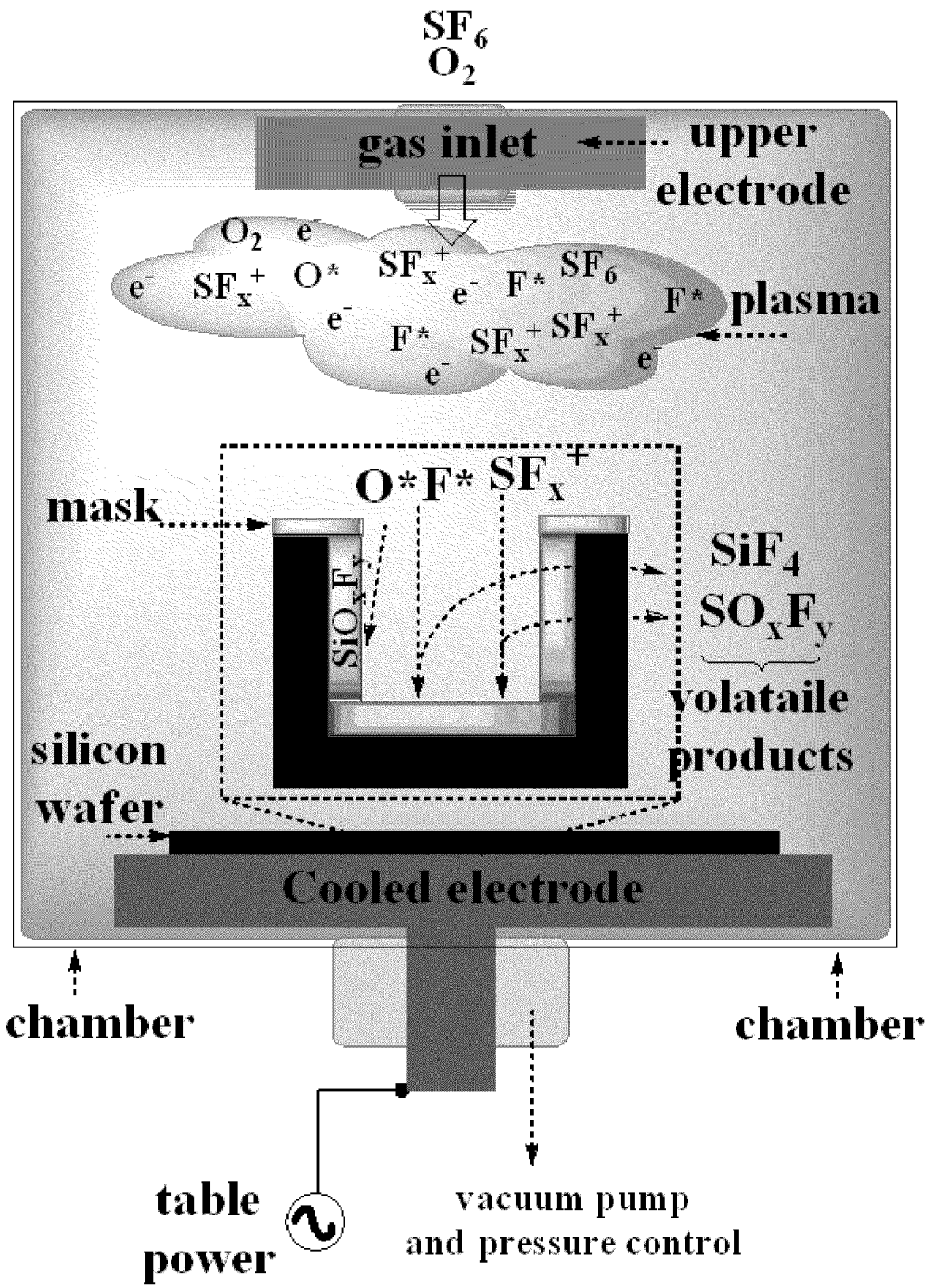
FIG. 1 is an illustration of one embodiment of black silicon fabrication.

In one embodiment of fabrication, shown in FIG. 1, a reaction chamber 110 includes a gas inlet 112 providing controlled delivery of gases to the reaction chamber 110. The reaction chamber 110 further includes an upper electrode 114 and a lower electrode 115. In one embodiment, the gas inlet and the upper chamber are positioned adjacent and at a top of the reaction chamber 110. The lower electrode is then positioned opposite the upper electrode 114 on a bottom of the reaction chamber 110. In one embodiment, the lower electrode 115 is cooled. The lower electrode is configured to receive a silicon wafer 120. The silicon wafer 120 has an exposed surface 121 that is exposed to interior of the reaction chamber 110. Specifically, during operation, gases, such as SF$_6$ and O$_2$ may be provided, such as by separate sources and pathways, to the gas inlet and into the reaction chamber 110. When the electrodes are activated, under current, plasma is generated within the reaction chamber 110 such as from the SF$_6$ and O$_2$. The plasma reacts with the silicon wafer. The exposed silicon wafer surface may have a patterned mask 125. The reaction chamber 110 may further have a controlled temperature and pressure. In some embodiments, temperature is critical (temp of wafer AND temp of the gas stream) and controlled. In a particularly implementation, the temperature of the gas stream is changed from 20 to 25° C. resulting in etching of a surface with heterogeneous pillar distribution (i.e., both "long" and "short" pillars). FIGS. 21A-B show etched silicon wafer at elevated temperature (25° C.) showing a heterogeneous rough surface displaying two lengths of nanopillars. During one embodiment of the etching process for nanopillars, O$_2$ forms a passivation layer SiO$_y$F$_x$ which protects the side walls of the pillars. The formation of a passivation layer is dependent mainly on temperature. The range of temperatures operable for the described nanopillar etching is between −130° C. to 30° C. In other embodiments, one or more of temperature, bias, wafer resistivity, gas pressure, gas ratios, gas flow geometry, gas release nozzle, chamber geometry, and chamber size are selectively controlled. In particular embodiments, the DC Bias is between 200-480V; the pressure is between 10-55 mTorr; gas ratios are between 0.8-1.2; resistivity is between 0.01-50 ohm-cm, each of which is inclusive of the end points of the ranges.

While the general etching technique described previously was utilized, the protocol was modified to provide for tunability of the bSi nanostructures. Balance of the gases is, therefore, important in order to obtain pillar-containing bSi nanostructures. To find the bSi "slot" or "hot spot(s)" in gas-ratio phase space, the SF$_6$ flow as well as other parameters were initially fixed and O$_2$ content was allowed to vary (typically between 0.85 and 1.05 ratio of O$_2$:SF$_6$). Therefore, it has been found that, for one embodiment, the bSi-regime was commonly found at a ratio of between 0.8 and 1.2, for example a ratio of 0.925.

Specific bSi nanostructures can be formulated with a variety of features. The features may include nanopillars, masked areas, semi-masked areas, reactive masked areas, and the like. Further, heterogeneous surfaces are possible through self-masking with multi-cycling etching protocols with varied instrument parameters. More easily achieved are heterogeneously etched surfaces using various masking techniques. Thus, a series of b-Si substrates exhibiting various nanotopologies were obtained by modulating etching processes. As the etching time increases, the pillars have shown to become longer and sharper, with regard to the angle of the tip of the nanopillar. In general, changing gas ratio and/or pressure allows for tuning of pillar shapes and/or densities.

Nanotextured Surface Regimes

The nanotextured surface needs to act on the wide range of chemical and mechanical properties displayed by bacterial cell envelopes in nature to provide useful ability to kill organisms and to selectively kill only certain organisms. The mechanism for killing the organisms is two-fold. In one extreme, referred to herein as "Regime 1," cells initially stick to the nanotextured surface and additional attractive forces further distort the critical peripheral membranes and cell wall structures. In a more aggressive, rapid type of interaction, referred to herein as "Regime 2," there is direct intracytosolic penetration of individual features (pillars/spikes) on the nanotextured surface that is biomechanical and occurs when sufficient stretching of the membrane is reached and tension finally results in nanopillar-mediated piercing of the cell. The latter mechanism contrasts with what is believed to be occurring with natural CWLN where the nanopillars are thick, blunt, and dense and promote bacterial adhesion between multiple spikes. Also, nanotextured surfaces may exhibit antifouling properties, which may require a separate set of characteristics for the features on the nanotextured surface. The Regime 1 and Regime 3 behavior may be by action of diffusion and gravity alone to interact the organism with the pillars. Alternatively, additional forces may be utilized, such as fluid movement, magnetism, or attractive forces.

One embodiment the nanotextured materials exhibit selective bactericidal properties, for example as selectively bactericidal bSi nanostructures. That is, the nanotextured surfaces are selective to a particular bacteria, such as by subspecies, species, genus, etc. Selectivity may be an order of magnitude (or larger) greater bactericidal efficiency for the selected bacteria or group of bacteria. For example, in one embodiment selectivity in a mixture of two or more species, one or more species is killed to at least the 80% levels and one or more species survives at the 80% or higher level for at least the time necessary to reach the 80% mortality level of the first species. The selective nanomaterials are referred to herein as "Regime 1" materials. As described further below, nanotextured materials that fall in Regime 1 exhibit a particular dominate bactericidal mechanism: stretching and tearing. The Regime 1 nanotextured materials interact with bacteria such that the nanopillars snag the bacteria, but do not pierce so deeply and thoroughly as to destroy. Rather, the bacteria is snagged repeatedly by multiple nanopillars, resulting in stretching and tearing of the bacteria. In one embodiment, Regime 1 is achieved, such as for bSi nanotextured materials, where the tips have an angle of above 30°, the pillar density is between 15 and 30 pillars per micrometer squared, and the pillar length is between 150 nm and 1.5 microns.

One embodiment the nanotextured materials exhibit that exhibit "super killer," that is, broad bactericidal properties that result in no or little selectivity, for example as general antimicrobial and/or antifouling materials, such as having bSi nanostructures That is, the nanotextured surfaces are selective to a particular bacteria, such as by subspecies, species, genus, etc. The "superkiller" nanotextured materials are referred to herein as "Regime 3" materials. As described further below, nanotextured materials that fall in Regime 3 exhibit a particular dominate bactericidal mechanism: piercing. The Regime 3 nanomaterials interact with bacteria such that the nanopillars pierce so deeply and thoroughly as to destroy. Thus, a single interaction with a nanopillar may be sufficient to kill bacteria rather than a prolonged interaction with multiple nanopillars in Regime 1. For example, in one embodiment, Regime 3 behavior is enabled where the tip angle is below 20°, the pillar density is between 2 and 20 pillars per micrometer squared, and the pillar length is between 400 m and 10 microns.

The range of feature parameters that fall between that which results in Regime 1 behavior and that which results in Regime 3 behavior is associated with Regime 2. Regime 2 exhibits less selectivity than Regime 1 but also less efficiency in death of organisms than Regime 3.

Applications of Nanotextured Materials

Nanotextured materials provide a versatile, tunable, antibacterial material that can be used in a wide range of applications, including but not limited to:

1. Sensors—specimen preparation for analytical assays.
2. Food and medicine storage/packaging.
3. Prevention of microbial colonization in medical devices or with wound treatment (implants, medical devices, wound management).
4. Control of organism populations in bioreactors or the environment (e.g., for biomanufacturing).
5. Construction and exposed surfaces, such as HVAC systems and human-contact surfaces.
6. Sprays for control of bacterial proliferation on plant or mammalian surfaces to control degradation and/or odors.
7. Water quality—anti-fouling filters;
8. Food preparation (e.g., cutting board coatings);
9. Tile/grout treatment;
10. Field emission;
11. Methods for facile sterilization of liquids, surfaces, and air.

Multi-step sample preparation presents a challenge for the development of low complexity devices and analytical assays. Many current technologies for killing bacterial also require the use of chemicals, which would contaminate any assay, fail to expose cellular contents to the outside environment, or create/require a harsh environment that may alter or destroy cellular contents with lysed.

FIG. 23A is a schematic of an interaction of a bacterial cell with a single, sharp, sparse, "superkilling" nanopillar. The release of proteins, DNA, RNA, lipids, metabolites, and other cellular components become possible at this stage. FIG. 29B is a photograph showing increased release of plasmid DNA from cells incubated for 4 hours on bSi (B4) relative to cells incubated on smooth control surfaces (C4), as measured through numbers of isolated colonies that resulted from transformation of chemically competent cells with aliquots of recovered cell suspension buffer (with cells removed).

In contrast to those current problems, a nanotextured surface can be tuned to exhibit rapid and generic lysing properties enable sample-containing bacterial cells to be readily prepared for the task. When spotted on the surface, bacteria are damaged passively upon contact with sharp pillars in an energy-free process. Disrupted cells provide proteins, RNA, DNA, lipids or metabolite markers that can be screened. As described above and further below, the nanotextured surface can be tuned to be selective for a particular type of bacterial, allowing the nanotextured surface to be deployed in environments where mixtures of bacteria are present. Further, the nanotextured materials can be incorporated into devices or apparatus that include active interaction such as microfluidics. The organisms, such as bacteria, can be actively exposed to the nanotextured surfaces, such as by pressure, centrifuge, vacuum, etc. FIG. 29G shows one concept for a microfluidic surface covered by black silicon that will be used in microfluidic devices for analytical assays.

In a further embodiment, a nanotextured surface may be constructed with discrete regions having selectivity for a particular bacteria. Thus, an apparatus may include the ability to analyze proteins, nucleic acids (including DNA or RNA), metabolites, lipids, enzymes, etc. of a particular organism while allowing other organisms to pass without being ruptured.

This chemical-free, economic cell lysis technology can be used for tests (i) where interference of lysing chemicals with an assay has to be avoided, (ii) to shorten the time needed to perform a diagnostic assay, and (iii) for environmental sensors aiming to screen airborne pathogens, to list a few. Contrary to chemical approaches, the system does not age, resulting in an exceedingly long shelf life, and it is not sensitive to extreme changes in temperature.

Food and Medicine Storage/Packaging

The described nanotextured materials can advance beyond the current state of the competing technologies in food and pharmaceutical storage market by (i) lowering the need for chemical preservatives and (ii) providing safe environments, free of ions (typically present in antimicrobial coatings, capable of interacting with food or therapeutics) and near sterile packaging conditions. The patterns responsible for protection from microbial activity of etched silicon surfaces can be transferred via molds and castings into packaging materials (polymers) to retain important features while expanding geometries amenable to the technology. In one embodiment, the molding is accomplished with a negative mold which is utilized to cast the positive "image" of the nanotexture on the material.

Prevention of Microbial Colonization (Implants, Medical Devices)

Emerging strategies to produce better performing implants use various surface modification and coating approaches. With an increasing number of surgical-site and prosthesis-related infection risks, the nanaotextured materials described herein will bring a new option for preventing such infections. Physio-chemical modification of an implant surface is relatively simple and economical to achieve and to industrialize. Additionally, silicon makes up the majority of the Earth's crust and is known for its high biocompatibility. The pattern can be also transferred into other base materials as a mechanism of action is driven by topography, not chemistry. The nanotexture pattern can be transferred to a flexible material, such as for clothing or coating on a curved surface. The transfer may be, for example, by molding and casting into soft materially and then chemically bonding this to surfaces or by making tiny pieces that are bond together with flexible linkers.

Control of Organism Populations in Bioreactors or the Environment

Selective bactericidal materials have the potential to enable the generation of sterile conditions while allowing one organism to thrive in a bioreactor (in biomanufacturing schema). One embodiment relates to a bioreactor used in biomanufacturing, which may be using a consolidated bioprocessing scheme that utilizes more than one species. It may be desirable to maintain a ratio of the production organisms while maintaining sterility in regards to all other organisms. Using the nanotextured material in Regime 1, the bioreactor is able to kill everything but the production set and also maintain the desired ratio of the production species to maximize productivity.

Thus, embodiments of the nanotextured materials having high selectivity can be utilized in a bioreactor or similar device. This strategy can reduce the time and costs (needed for sterilization of reaction components) of the production processes, thereby increasing the potential of the bioconversion approach when competing economically with fossil-derived processes for the production of fuels and chemicals. For example, for bioreactors with circulating media, the media could be exposed to the nanotextured material during circulation. Further, the nanoreactor itself could have surfaces with the nanotextured materials, to inhibit growth.

Nanotextured materials could also be used in many other facets of manufacturing, especially those switching to renewable-replacements strategies (usually with biological steps), to prolong production cycle times wherever biofouling becomes rate limiting. The agricultural community could benefit from nanotextured materials to protect plant biomass and/or the fruits, vegetables, and seeds they produce.

In another embodiment, the nanotextured material is utilized with constructs such as liposomes. The interaction of the liposome with the nanotextured material results in a rupture in the liposome lipid bilayer, resulting in a release of material contained in the liposome. In another embodiment, the nanotextured material is injected into microfluidic droplits, liposomes, or the like.

In another embodiment, the nanotextured material has antifouling properties. The nanotextured material may selectively prevent or allow biofilms, for example allowing a desired biofilm while preventing others.

Experimental Methods

Described herein are experiments relating to certain embodiments. Such experiments are detailed for illustrative purposes. While the nanotextured materials may comprise various materials as noted previously, the experimental examples utilize black silicon for ease of preparation and comparison between samples.

To address the challenges of providing tunable and improved antimicrobial stuctures, bSi was created with a wide range of nanotopographies using the Reactive Ion Etching ("RIE") technique and the bactericidal effectiveness of these materials towards three Gram-negative genera (*Escherichia* ("*E.*"), *Pseudomonas, Rhodobacter* ("*R.*")) and one Gram-positive genus (*Bacillus* ("*B.*")) was investigated. Controlled modification of etching conditions reproducibly altered the features of these rough surfaces (e.g., nanopillar length, tip shape, and spacing). Controlled tunable bactericidal black silicon are described with experimental evidence showing not only the differences in bSi antimicrobial performance towards Gram-positive and Gram-negative species but also, and possibly more importantly, among the same group.

Fabrication of bSi

Silicon wafers (4", p-type boron-doped, <100>, resistivity 10-20 $\Omega \cdot cm^{-1}$, 525±25 µm, purchased from Silicon Quest International) were etched by RIE technique (Oxford PlasmaLab 100) at temperature of 20° C. The black silicon-regime was found using the protocol developed by Jansen, et al., with certain adaptations. Prior to the beginning of the process, wafers were cleaned with acetone. Resulting black silicon fabrication conditions were: RF 100 W, pressure 35 mTorr, back cooling electrode He 5 Torr, $O_2$ and $SF_6$ flows 36 sccm (standard cubic centimeter per minute) and 40 sccm, respectively. The etching time was varied between 1.5 and 30 min. The sample used most prevalently (as a benchmark) was prepared by etching for 15 min. To facilitate tests with 1 $cm^2$ materials samples, full-size wafers were spin-coated with a photoresist MEGAPOSIT™ SPR™ 220-7.0 positive photoresist (Rohm And Haas Electronic Materials, LLC.), 35 s at 3500 rpm, and baked for 2 min at 115° C. The wafers were diced into 1 $cm^2$ pieces and stored for use in future experiments. The photoresist was removed by 3 times acetone/sonication bath for 2 min.

Characterization of bSi Surface

SEM micrographs were taken using a JEOL 7500 Field Emission Scanning Electron Microscope, operating at 10-15 kV. The ImageJ program was used in order to determine the mean spike densities based on top views through analyzing at least 5 independent fields. The spike lengths and base diameters were determined using edge cross sections by counting at least 100 spikes in a given field of the SEM images. The pitch was determined using a nearest-neighbor-distances ("NND") ImageJ plugin (https://icme.hpc.msstate.edu Author: Yuxiong Mao).

Static water contact angles were determined using a dedicated, contact-angle-measurement device (FM40 Easy-Drop, KRÜSS GmbH, Hamburg, Germany).

Here, 5 µl droplets of deionized water were placed into three different positions on the sample surfaces, and the angles of drops were determined and averaged.

Cell Cultures

Three Gram-negative genera *Escherichia, Pseudomonas, Rhodobacter* were used in this study. *E. coli* strain DH5a harboring broad host range plasmid [pBBR1MCS-2] was cultured on LB medium, aerobically, at 37° C. Aeration of the culture was provided by shaking set at 250 rpm. *P. fluorescens* (SBW 25) was grown on LB medium as *E. coli* but at 28° C. and 225 rpm. *R. sphaeroides* and *R. capsulatus* (Δrshl [pBBRRW] and U43 [pBBR1MCS-2], respectively) were cultured on YCC (YCC medium containing an additional 1 g/L of yeast extract, pH 7.1) and $^S$RCVPY medium, respectively. They were grown under semi-aerobic, chemoheterotrophic conditions in the dark (125 rpm, silicone sponge closures, 33° C.).

Bacterial Cells Viability Test

Figure 2A:
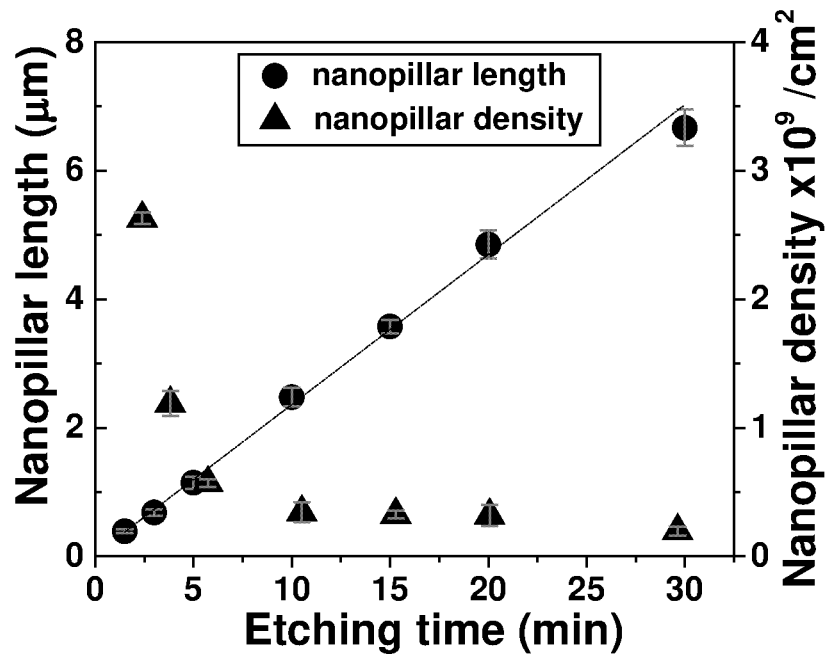
FIG. 2A shows the temporal evolution of nanopillar morphology (length and density) during the black silicon fabrication process, spanning 1.5 to 30 min.
Figure 2B:
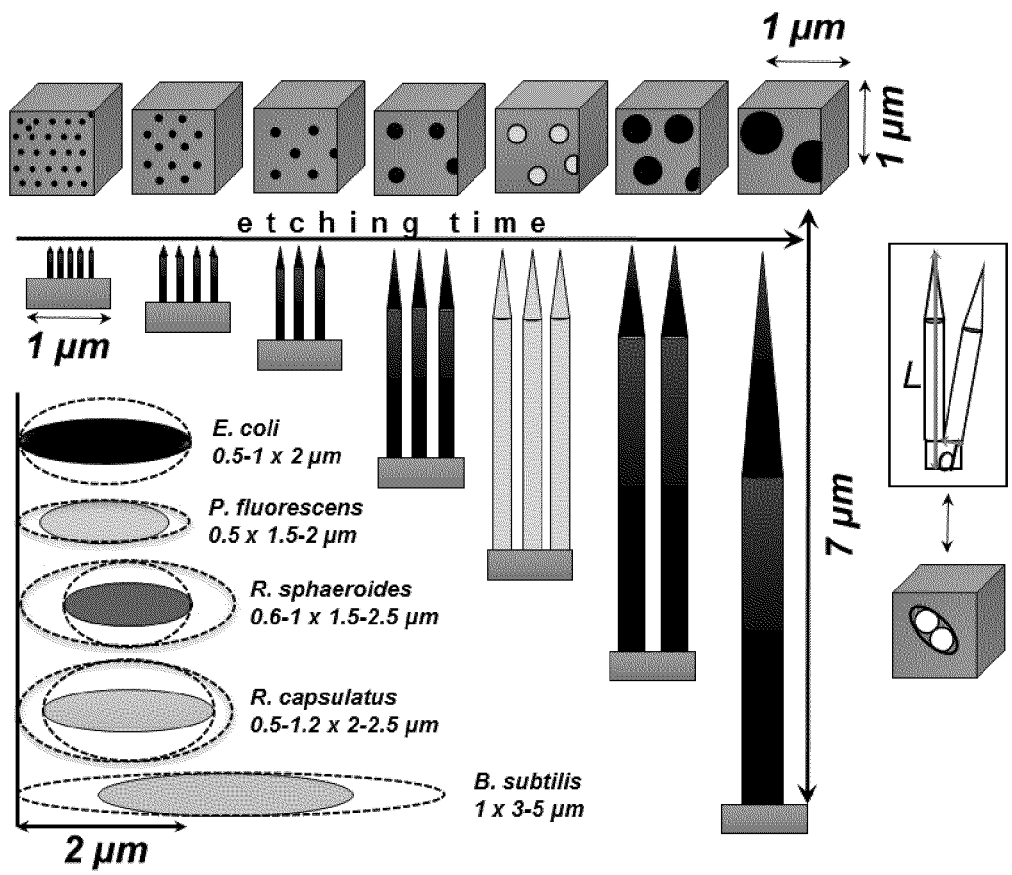
FIG. 2B illustrates a schematic representation of resulting nanostructures.

The bactericidal activity of bSi was quantitatively evaluated using a plate counting method. Bacteria were cultured in rich media until the mid-log phase was reached. The cultures were then diluted into fresh media to the concentration of $1.6 \times 10^7$ cfu/ml. Prior to the experiment, both black silicon and control surfaces were autoclaved. 24-well protein crystallization plate containing a pedestal located centrally in a well (Chryschem, Hampton Research) was used as a humidity-controlled experimental system to prevent evaporation (FIG. 2A). To assure even humidities, 1 ml of sterile water was added per each well, wafer/control was placed on the top of pedestal, 20 µl of cells were added, and the well was sealed with vacuum grease and glass cover slide (22 mm diameter). All experiments were performed at room temperature (RT, 25±0.5° C.) up to 4 h. At given time intervals, cells (20 µl) were retrieved after in situ dilution 1:2 with fresh medium, serially diluted further to obtain 50-300 colony-cell with controls, and ultimately spread on agar plate. Cell suspensions were plated on rich medium containing appropriate antibiotics as necessary. Finally, colony forming units were counted and bactericidal efficiency was demonstrated based on the percentage of bacteria recovered from bSi versus control surfaces.

The controls were chosen experimentally by comparison of growth kinetic of *E. coli* on the various surfaces to their growth in the static microfuge tubes (evaluated by $OD_{600}$ measurements). The experiments were carried out as viability tests (vide supra). The tested surfaces were non-etched silicon wafers and glass cover slides, and their hydroxylated variants generated by air-plasma exposure for 5 min.

Problematically, there is a lack of standard methodology for testing of bactericidal properties that allows for (i) straightforward comparison of the advantages/disadvantages, (ii) optimized understanding of their potency and utility and, ultimately, (iii) accelerated evaluation of the market for the new materials platforms in a vast field of applications. The need for standardization results from comprehensive comparison of methodologies used extensively in the field (e.g., colony counting and confocal/electron microscopy) with the novel application of flow cytometry. The data reveal how the techniques are complementary but not necessarily comparable or correlative. In contrast, evaluation of results taken using different methodologies on different materials can be grossly misleading. For some results described herein, there are significant differences in bactericidal efficiencies depending on methodology employed. In addition, it is demonstrated how cytometry is yet another powerful complementary tool that can aid in mechanistic understanding of antimicrobial activities of rough surfaces. The highest, and rather misleading, bactericidal efficiencies were found when incubations proceeded in nutrient-free buffers, such as the industry standard phosphate-buffered saline. Besides standardization for comparison, evaluation methods need to take into account anticipated applications and whether or not planktonic or surface-attached cells are the primary target.

FIGS. 24A-B show bactericidal efficiencies of etched silicon (L=390 nm) towards *E. coli* and *R. capsulatus*. Bacteria were interacting with the surfaces for 2 h in three media: rich, poor, and nutrient-free buffer. The bactericidal efficiencies were determined based on number of viable cells remained in solution, enumerated by plating method and flow cytometry (using live/dead fluorescent staining), according to the following equation:

$$BE = 100 - \left( \frac{\text{\#viable cells after incubation on } bSi}{\text{\#viable cells after incubation on control}} \times 100 \right)$$

Additionally, BE was calculated based on number of viable and dead cells attached to the surface by means of confocal microscopy and the live/dead staining using the following equation $$BE = \frac{\text{\#dead cells}}{\text{\#total cells}} \times 100.$$

The values are expressed as a mean±SEM (n=3 independent experiments).

Results vary by methods used and each of the method is complementary, contributing to the mechanistic understanding of bactericidal performance of studied materials. For example, data were collected for surfaces of Regime 3. For example, cytometry indicates ~25% lower BE values than plating method when characterizing killing efficiencies of sharp nanopillars interacting with *E. coli*. Likely because it scores injured cells as alive but plating method reveals that those cells are not able to recover.

Live-Dead Staining

The viability of various bacterial species on the bSi substrata was also evaluated by confocal microscopy. The experiments were performed to validate tests base on the plate-counting method. Similar methods were used but with higher concentration of cells for better visualization. Bacteria were grown to mid-log phase and subsequently diluted to $2.8 \times 10^7$ cfu/ml. At given time intervals, the surfaces were washed 3 times with 1×TBS to remove planktonic (non-attached) cells as well as traces of medium, followed by staining with LIVE/DEAD® BacLight™ Bacterial Viability Kit (L7012, Invitrogen) per instructions. The kit contains SYTO 9 (green) and propidium iodide (PI, red) dyes that stain the cells depending on their membrane integrity. Bacterial cells with intact membranes are stained green, whereas cells with a damaged membrane (that are considered to be dead or dying) are stained red. Image acquisition and analysis were performed using a Nikon Eclipse Ti microscope with 100× objective, a 1.45 oil immersion lens and NIS-Elements AR 4.50.00 software. The cells were visualized by using 470 and 555 nm excitations and RGB multi-bandpass emission filter. Two color channels, green and red, were acquired for each image. To remove the fluorescent background noise from the image, brightness levels in every channel were adjusted.

SEM Imaging of Cell/Surface Interactions

Cells were allowed to interact with the bSi surface for 2 h, washed twice with 1×PBS, and subsequently fixed using 2.5% glutaraldehyde (GA) solution in 1×PBS for 30 min (V=50 µl; RT; GA stock 25% in $H_2O$). After fixation, surfaces were washed twice in 1×PBS and subsequently dehydrated in an ethanol series of 25%, 50%, 75%, 95% and 100% (v/v) for 10 min each. Samples were critical point-dried ($CO_2$/EtOH), sputter-coated with Au and imaged using a JEOL 7500 Field Emission SEM.

Tracking Cell/Surface Interactions

A fluorescent strain of *B. subtilis* (DK400)38 was grown in Terrific Broth medium in the presence of IPTG (100 µM; Sigma Aldrich) at 30° C. for approximately 14-16 hours. A ~10 µL droplet of bacterial suspension (OD600~2) was transferred to either a bSi (3.6 µm nanopillars) or a smooth, control surface. To minimize evaporation, the 1 cm2 wafer was enclosed in a sealed, optically clear chamber (of 1.5 cm×1.5 cm×0.2 cm dimensions). To observe bacterial motility and interaction of the cells with the silicon surfaces, an inverted microscope Olympus IX71 (10× objective, NA 0.40) and a monochrome camera Prosilica GT1660 were used. Excitation and emission through monochromators was at 587 and 610 nm, respectively. A frame rate of 15 fps (66 ms exposures) was found to be the optimum data acquisition speed that balances fluorescent sensitivity, accurate tracking of bacterial motion, and reduced photobleaching of GFP-containing bacteria. These conditions allowed for acceptable signal-to-noise ratios during experiments that lasted 20-30 seconds. The visual analyses of bacterial dynamics during the initial bSi interaction period allowed detection of distinct events, e.g., sudden stopping and dislodging of the cell by the external shear flow. The sequence of frames was processed in MATLAB using a custom script. While the position of an individual bacterium was tracked manually, the orientation was detected automatically based on a fast Fourier transformation of the bacterium and its surroundings in the image.

Nanopillar Morphology

The morphology (total nanopillar lengths and densities) of bSi substrates changes dramatically as etching time is increased. In the embodiments studied, etch time was increased varied from 1.5 to 30 min (FIG. 2A; for details, see Table 1 below). A correlation between etching time and nanopillar length is clearly seen and is confirmed by a Pearson correlation coefficient (0.9990; p<0.05). An etching rate of ~3.7 nm $s^{-1}$ (~220 nm·$min^{-1}$) is observed. For the embodiments studied, the nanopillars were from 0.4 to 6.7 µm long and exhibit tight distributions of lengths (FIG. 4). Correspondingly, there is a marked decrease in nanopillar density for the structures. The shortest nanopillars studied had a density of $26 \times 10^8$ $cm^{-2}$ and average pitch, center-to-center distance, of 130 nm, and at 10 min of etching and beyond, the density reaches a plateau of ~$3 \times 10^8$ $cm^{-2}$ with average pitch around 420 nm with distributions that broaden. The frequency of nanopillars on all of the surfaces studied allow for single cells to interact with multiple nanopillars (FIG. 3C), but the possibility for multiple interactions per cell is higher for surfaces etches for shorter times.

FIGS. 15-18 illustrate micrographs and illustrations demonstrating the bSi topography's impact on the number of nanopillars that interact with a cell. FIG. 15 illustrates an electron micrograph of a black silicon bactericide material with 3.6 µm height nanopillars, ~3 nanopillars/$µm^2$, average pitch 380 nm (±130) and with Image magnification 33,000× (scale bar 100 nm). FIG. 16 illustrates the size of a bacterial cell relative to the nanopillar dimensions. The size of bacterium here 2 µm long, 0.5 µm wide. This is a representation of *E. coli* or *R. capsulatus*. On the both FIGS. 16E and 16G are *R. capsulatus* cells interacting with bSi. However, this is roughly the same size of all tested Gram-negative species and all other Gram-negative species explored in any laboratory in any type of experiment to date. FIG. 17 illustrates an electron micrograph of a black silicon bactericide material with 0.4 µm height nanopillars, ~27 nanopillars/$µm^2$, average pitch 130 nm (±40) and with image magnification 45,000× (scale bar 100 nm). FIG. 18 illustrates the size of a bacterial cell relative to the nanopillar dimensions.

TABLE 1

Topographical features of black silicon fabricated for various etching times. The values are presented as a mean ± standard deviation. Total length, tip length, base diameter, and pitch were measured for at least 50 pillars by analyzing at least five fields of view. Nanopillar density was measured by analyzing at least five fields of view

| Etching time t (min) | Total length L (µm) | Tip length $L_{tip}$ (µm) | Tip angle α (°) | Base diameter d (nm) | Nanopillar density ($µm^{-2}$) | Pitch (nm) | Wenzel roughness (n/a) |
|---|---|---|---|---|---|---|---|
| 1.5 | 0.39 ± 0.03 | 0.07 ± 0.02 | 44 | 50 ± 10 | 26.3 ± 0.4 | 130 ± 40 | 1.79 |
| 3 | 0.68 ± 0.05 | 0.12 ± 0.02 | 33 | 70 ± 20 | 11.9 ± 0.9 | 180 ± 60 | 1.90 |

TABLE 1-continued

Topographical features of black silicon fabricated for various etching times. The values
are presented as a mean ± standard deviation. Total length, tip length, base diameter,
and pitch were measured for at least 50 pillars by analyzing at least five fields of
view. Nanopillar density was measured by analyzing at least five fields of view

| Etching time t (min) | Total length L (μm) | Tip length $L_{tip}$ (μm) | Tip angle α (°) | Base diameter d (nm) | Nanopillar density ($\mu m^{-2}$) | Pitch (nm) | Wenzel roughness (n/a) |
|---|---|---|---|---|---|---|---|
| 5  | 1.15 ± 0.09 | 0.25 ± 0.05 | 23 | 100 ± 10 | 5.7 ± 0.3 | 280 ± 90  | 1.97 |
| 10 | 2.48 ± 0.15 | 0.68 ± 0.10 | 14 | 170 ± 50 | 3.4 ± 0.8 | 400 ± 120 | 3.17 |
| 15 | 3.58 ± 0.10 | 0.81 ± 0.29 | 16 | 220 ± 40 | 3.3 ± 0.2 | 380 ± 130 | 4.89 |
| 20 | 4.85 ± 0.22 | 1.06 ± 0.40 | 17 | 320 ± 80 | 3.1 ± 0.8 | 490 ± 130 | 8.32 |
| 30 | 6.67 ± 0.28 | 2.64 ± 0.56 | 10 | 490 ± 90 | 1.9 ± 0.3 | 600 ± 190 | 10.74 |

A photograph of a full-size black silicon wafer (homogenously etched after 15 min of fabrication) reveals the black surface resulting from the layer of nanopillars that present a graded transition of the refractive index from air to the bulk Si layer (FIG. 2A). This refractive-index gradient leads to effective suppression of reflected incident light and enhancement of scattering and absorption. It is noteworthy that only slight variations in the gas ratio affected the homogeneity of the surface structure, with striking impacts upon spike shape and density (narrow slot in gas ratio phase space for bSi; data not shown).

Figure 3A:
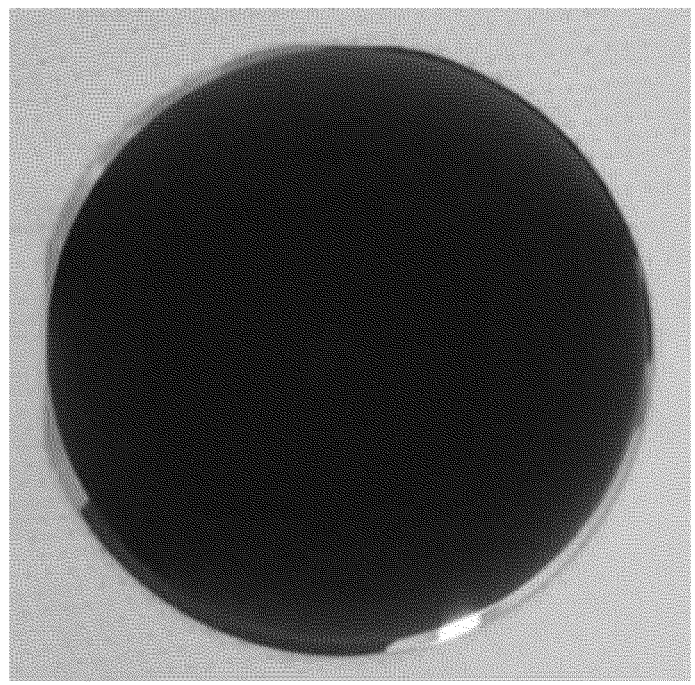
FIGS. 3A-I show topographical features of black silicon.
Figure 3B:
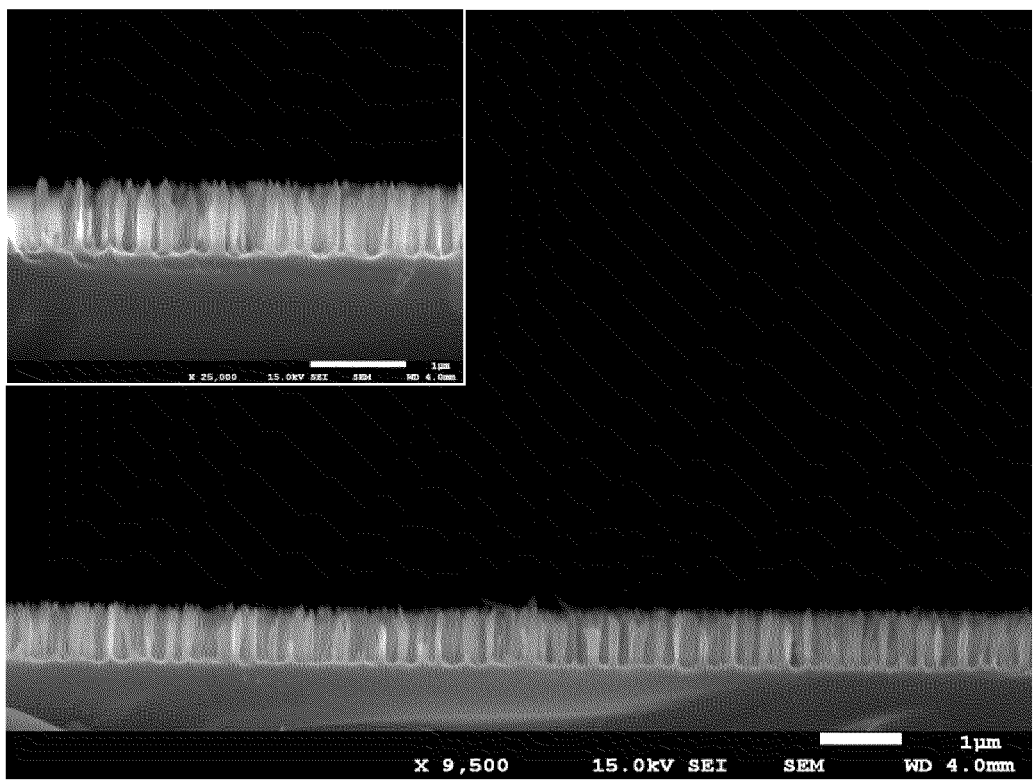
Figure 3C:
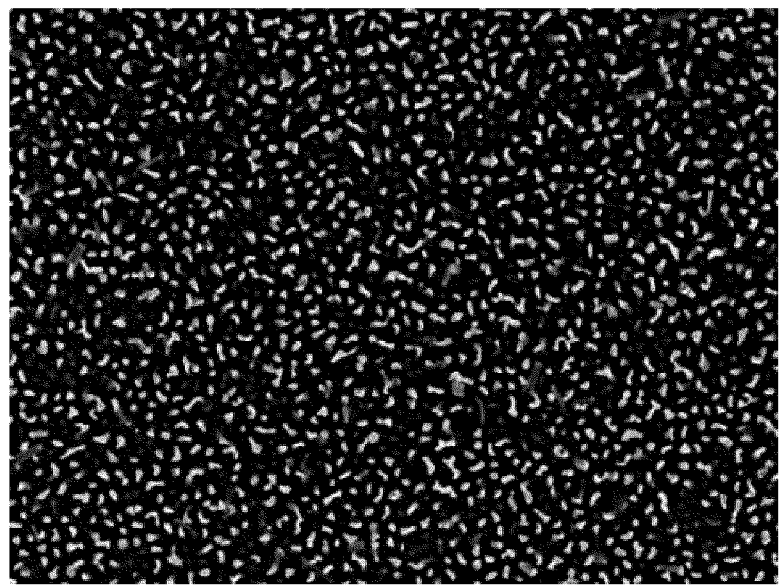
Figure 3D:
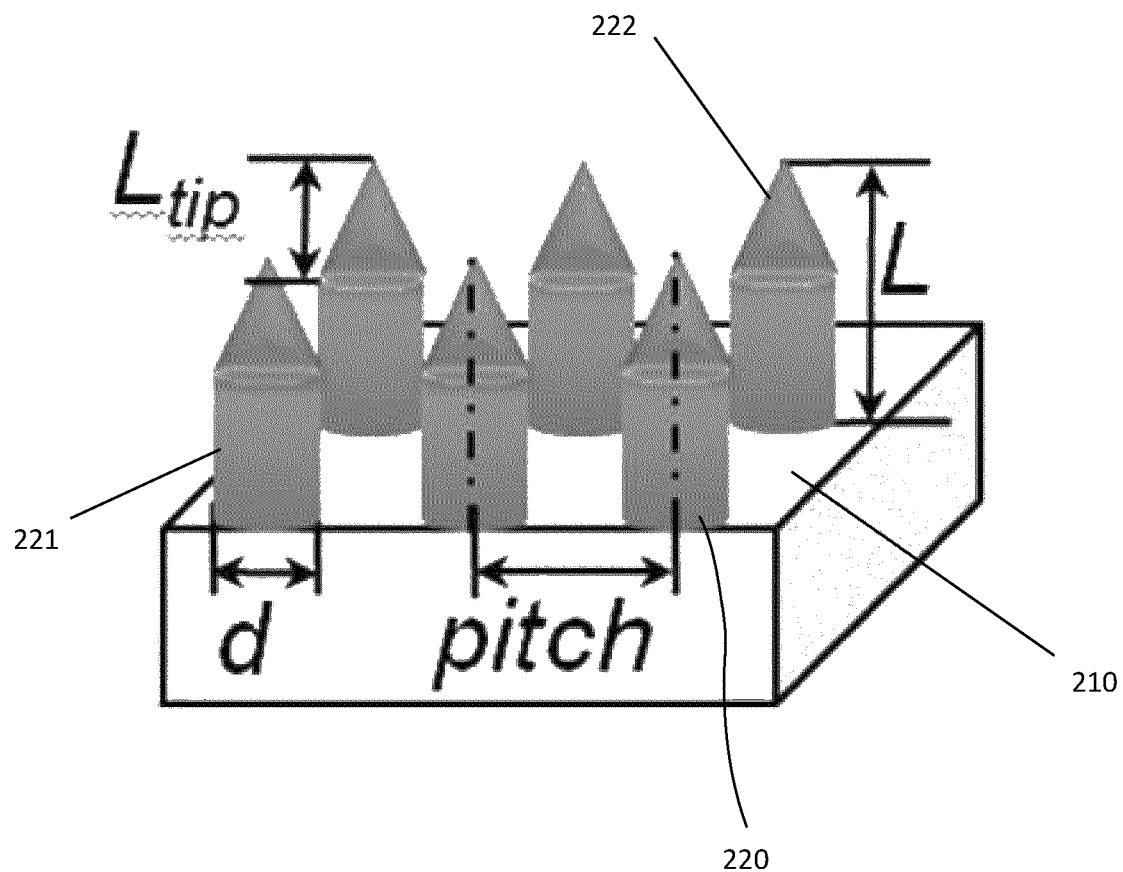
Figure 3E:
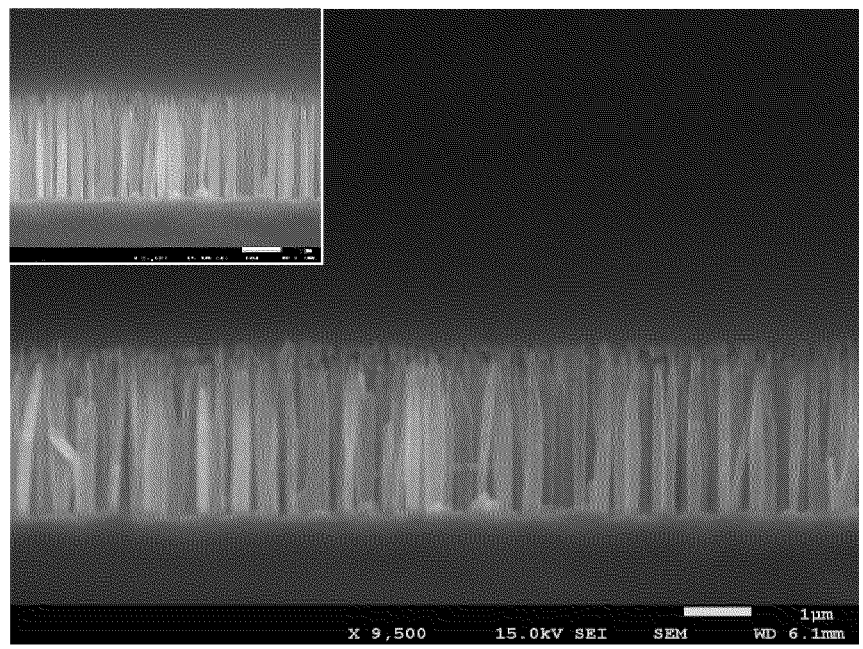
Figure 3F:
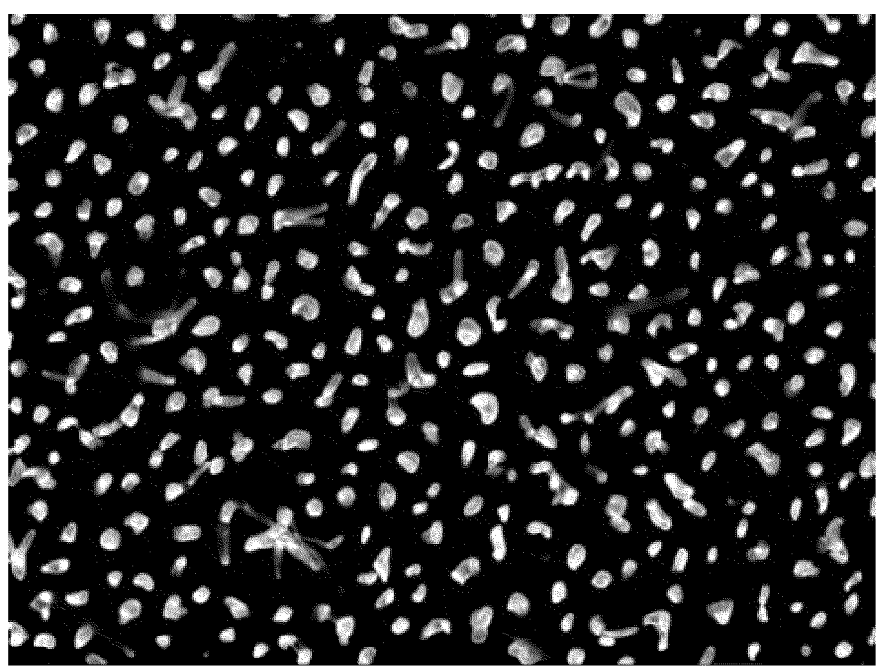
Figure 3G:
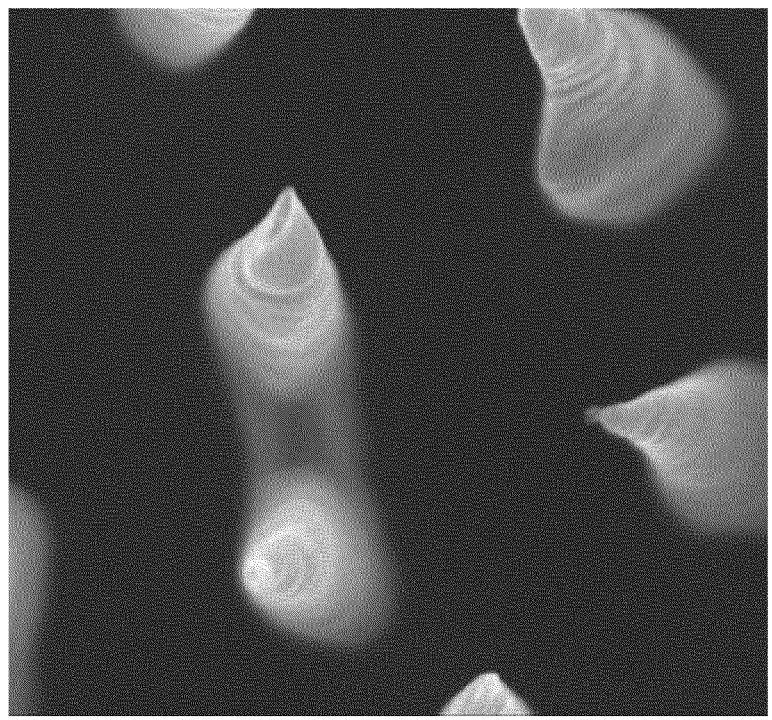
Figure 3H:
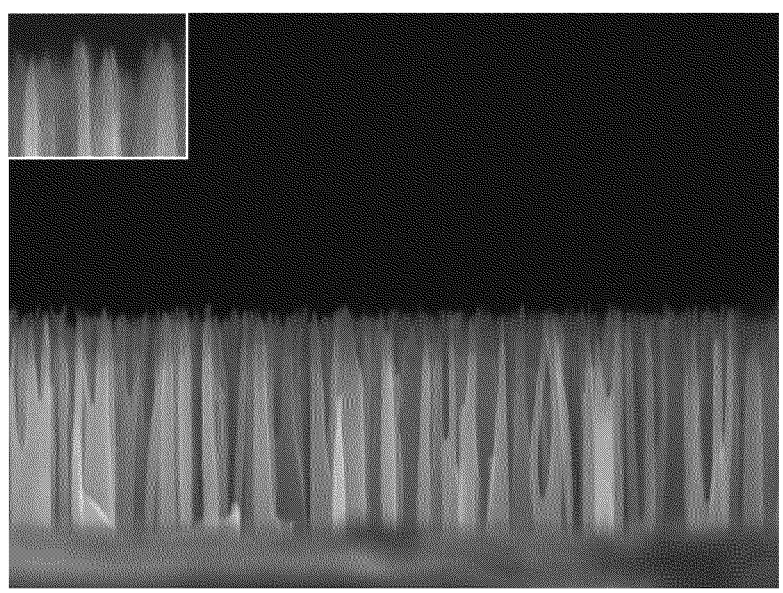
Figure 3I:
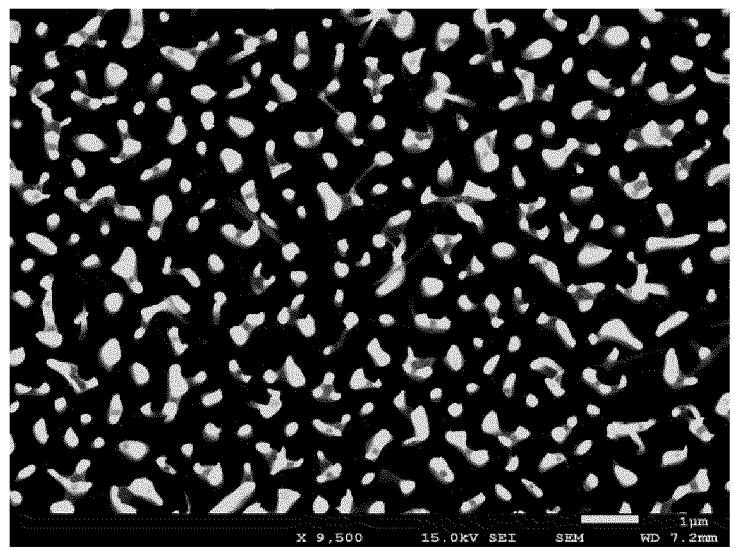
Figure 4:
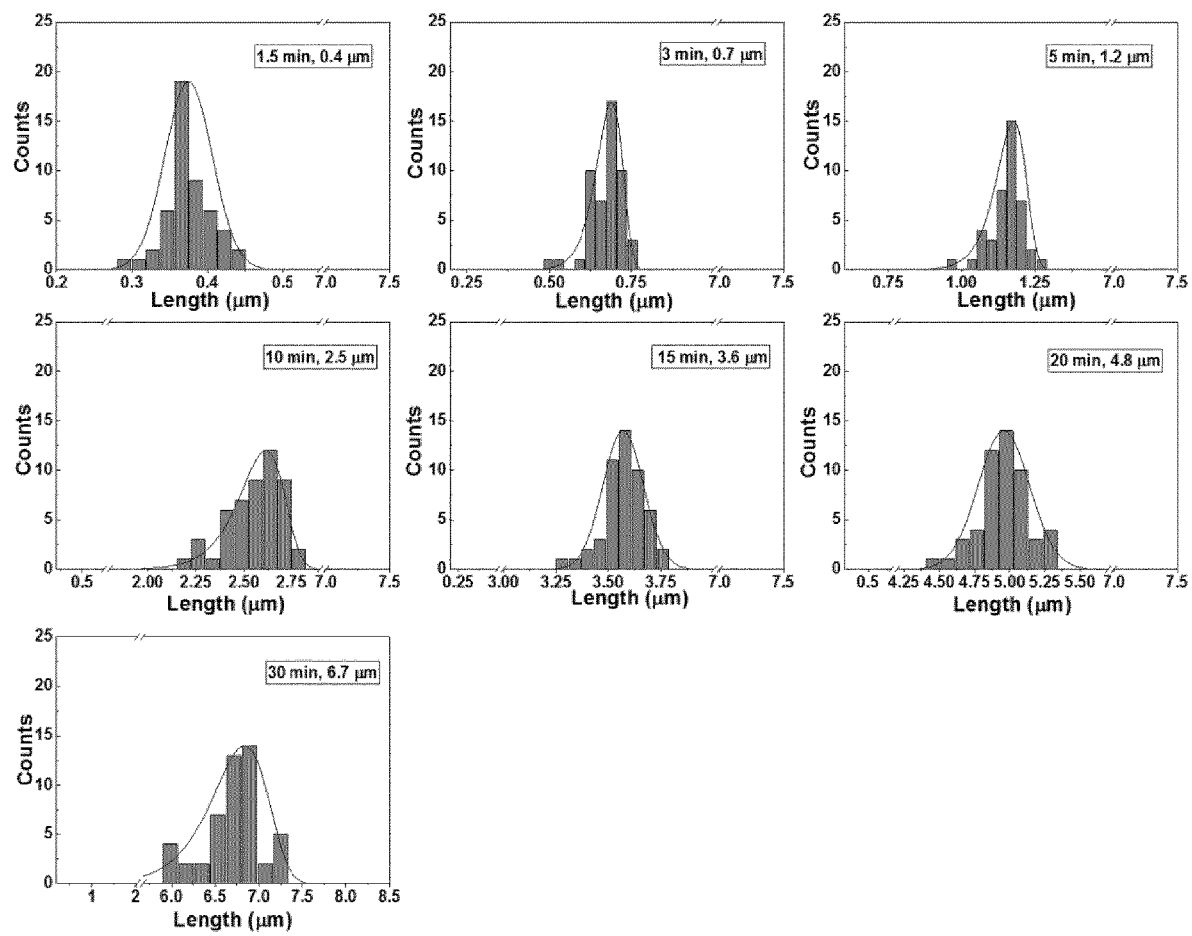
FIG. 4 shows distribution graphs for the nanopillar lengths for bSi etch times of 1.5 min, 3 min, 5 min, 10 min, 15 min, 20 min, and 30 min.

FIGS. 3B-I show the morphological and structural properties of certain bSi materials, illustrated by means of SEM. The figures show SEM micrographs of representative nanopillar architectures of bSi for selective etching times, as well as a schematic representation of the resulting bSi morphologies. Morphological properties of the features include tip length ($L_{tip}$), feature length (L), feature diameter (d), feature pitch angle (relative to the plane of the silicon substrate), as well as tip angle and density of features. Specifically FIGS. 3B-C show a 3 minute etch, FIGS. 3E-F show a 10 min etch, and FIGS. 3G-I show a 15 min. FIGS. 3B, 3E, and 3H show cross sections with insets presenting a magnified view of the tips, and the corresponding images in FIGS. 3C, 3F, 3G, and 3I show top views of etched surfaces. FIG. 3D shows a schematic representation of the pillars where L is total length, $L_{tip}$ is a length of sharpened tip, d is base diameter, and pitch (center-to-center) is a distance between centers of two pillars (spacing+diameter). Scale bars are conserved at 1 μm in all images, except 2.5 cm, and (FIG. 3G) 100 nm, and insets of (FIGS. 3B, 3E, and 3H) 400 nm. The images clearly reveal that longer etching time not only results in an increase in nanopillar length but also in a decline in nanopillar density (see top views, from 11 to 3 pillars per 1 μm² for 3 and 15 min of the etching time, respectively). As can be seen in from the data in the table, angle of the tip (sharpness) also changes. In one embodiment, longer etching provides a larger angle (i.e., sharper tip).

While not bound by theory, it is believed that as the etching proceeds, some pillars are eliminated, resulting in a reduced density. In an alternative embodiment, masking could be used to selectively control whether pillars are eliminated. Masking can likewise be used to create a nanotextured material with discrete regions of nanopillars, such as a more dense region or a region with greater tip angles (sharper) on the nanopillars. In a further embodiment, impurity levels can be utilized to control this pillar elimination. Impurities dictate the resistivity of the silicon wafers and influence the choice of bias voltage applied during the etching process. Thus, impurities have the ability to modify how attractive the surfaces are to charged gases and hence dictate the rates of etching and consistency in which the gases attach the silica surface. The process of self-masking can be modulated by the types and mounts of impurities that are doped into the wafers during manufacture.

Figure 5:
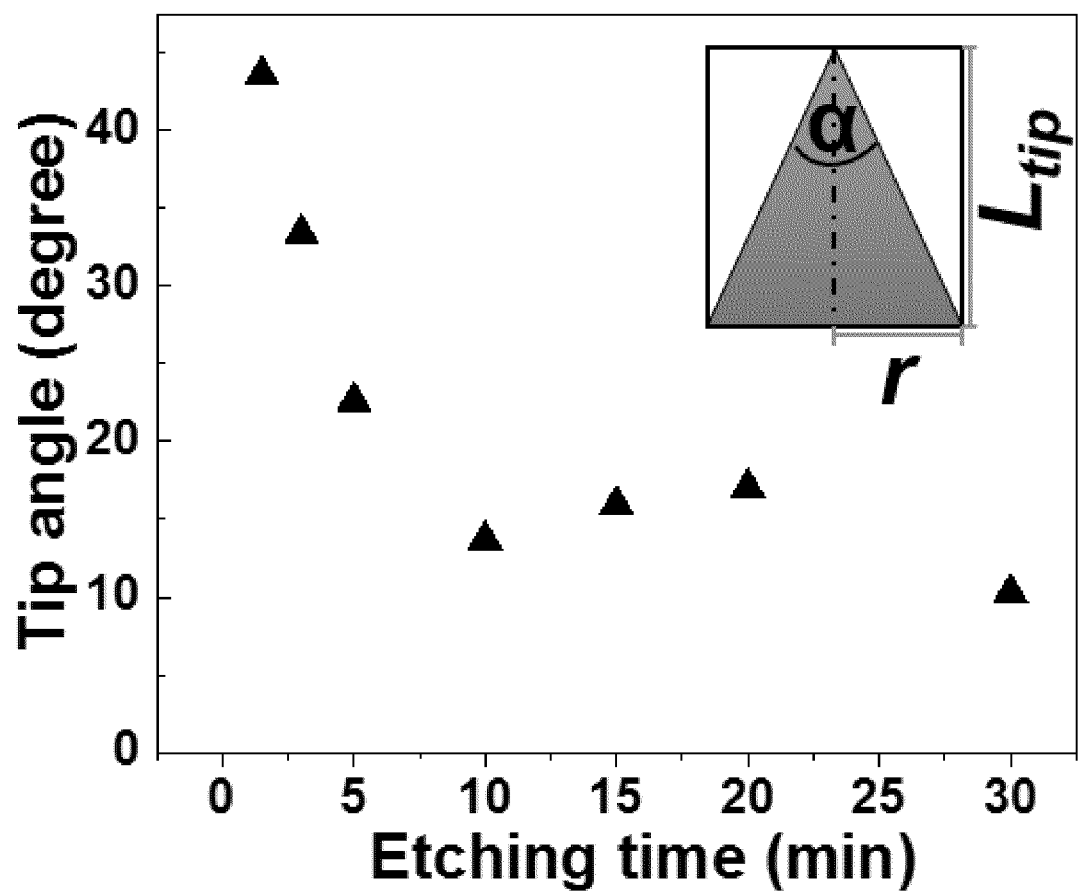
FIG. 5 shows the temporal evolution of the sharpness of the bSi nanopillars—as parameterized by the tip angle (a)—during the fabrication process, spanning 1.5 to 30 min. The inset schematically represents how the tip angle was calculated with the equation.

At the beginning of the process, many nucleated pillars are present. During the course of etching, smaller and thinner needles become shadowed by larger spikes and are constantly eliminated leading to the observed decrease in their density as well as a shift in the average pitch towards bigger distances (see FIGS. 5 and 6). These nanotopological features are in general agreement with studies performed by Pezoldt, et al. Additionally, as the etching time increases, the base diameter also widens and the frequency of the occurrence of multiple (double or triple) pillars growing from a common base increases. Interestingly, for the pillars resulting from etchings of 10 min and beyond, the aspect ratio remains constant (15±1), indicating a proportional increase of the nanofeatures of lengths, widths, and tips. Pezoldt, et al., and Gervinskas, et al., (Ann. Phys. (Berlin) 525, No. 12 (2013)). describe the dynamic range of the process, but they do not explore materials with nanopillars longer than 800 nm. However, that work did not review beyond 3.5 μm and utilized a relatively slow etching rate of ~100 nm/s. In contrast, for one embodiment the methods and fabrication described herein utilizes an etching rate of at least 200 nm/s.

FIG. 7 shows SEM images of bSi etched for 1.5 min. The average nanopillar length is 390 nm (Table 1). FIG. 7A utilizes scale bars of 100 nm (top). FIG. 7B utilizes scale bars of 1 μm (bottom). These images emphasize the blunt nature of the tips of these nanopillars with tip angle (i.e., sharpness) averaging 44°, with many displaying onion-like features.

Further, pitch of the nanopillars (i.e., the distance from the center of one pillar to another) can be controlled by tuning the etching, such as by altering the gas ratio and or the pressure. It should be appreciated that too high of pitch would allow bacteria to remain undamaged and/or unstuck to the surface by physically locating between nanopillars. The gas ratios, chamber pressure affect density; for example, lower oxygen usually results in lower density; DC bias, time, temperature, etc. are also controllable parameters. Temperature modification allowed for control of the pillar length.

In embodiments described herein, nanopillars are homogenously distributed and do not exhibit any of the ordered spatial arrangements that are observed in natural systems (e.g., hexagonal patterning). It should be appreciated that nanopillar initial nucleation can be controlled or masking done to achieved non-homogenous distribution. As an example, one could mask large sections/patterns (or smaller regions) and set up an initial etch. The mask could then be removed and etching could be allowed to continue with the same or varied parameters (further carving away portions of the wafer exposed at all times and having an altered result on regions that were initially masked). Importantly, as a result of these changes, tip geometry also changes. Although pillars possess relatively sharp tips after 3 min of plasma exposure, some tips according to prior art techniques exhibit onion-like structure with shorter tip and a "bulb" (see an inset, FIG. 5). Similar bulbous morphologies of bSi tips has been reported by Pham, et al., for the pillars of analogous length of ~620 nm. After 10 and 15 min of the etching time, the pillar tips become more uniform and very sharp (FIG. 2G and insets 2E, 2H).

In one embodiment, the surface has variable bactericidal rates for different organisms. For example, the surface having the nanopillars may have multiple features that could generically or specifically attract/kill different (sub)populations. For example, if specificity for two (or more) organisms was required for an application, then engineered regions of the surface could be setup for the bactericidal targeting of separate species. Yet additional regions on same surface could protect all of the rest of the organisms that were planned to be spared. This might be an ideal scenario for the surfaces of a bioreactor where the production host is protected and living contaminants are readily targeted.

In a further embodiment, the surface may utilize an arrangement wherein the organism is attracted and held, but not killed. Thus, the nanopillar structure attracts and retains the organism without causing sufficient damage to kill the organism. For example, such holding surfaces may be surfaces with nanopillars that serve as holding stations for particular species involved in an assay or in a multimode screening strategy where just bacteria with certain attributes proceed to the next steps. Here, the desired bacteria could be held in place with reversible attractive forces (without piercing or disrupture) and others would either be killed or repelled. In this way, live fraction of bacteria (potentially from complex communities or environments) could be subject to further study or used in enrichment proceedings that would be used for competitive advantage or used in studied to direct evolution.

Surface Wettability

The antimicrobial activity of surfaces of varied wettability have been intensively studied. Wettability and surface topography are known to have a relationship. For example, lotus leaves exhibit ultrahydrophobicity due to surface roughness. Although there is no obvious dependence found between surface wettability and its antibacterial properties, various studies relate differences in bacterial adhesion with this factor. Further, the ability to fabricate a hydrophilic nanopillar surface allows for a range of surface chemistry modification techniques not available to hydrophobic surfaces. For example, a chemoattractant may be placed between the nanopillars (interpillar materials) to encourage proximity by organisms. Generally, short needles (like Regime 1) are not superhydrophilic but are hydrophilic while Regime 3 materials are superhydrophilic.

As such, surface wettabilities is a consideration in one embodiment. While prior art nanotextured materials, in particularly bSi nanopillars, have been characterized by poor wettability, in one embodiment, the nanotextrured material, such as a bSi material, exhibits improved wettability. The wettability of a surface has been characterized with static water contact angle ("CA") measurements. Starting materials were moderately hydrophilic with CAs averaging ~40°, but all etched substrata became superhydrophilic (rough surfaces of materials, on which water spreads completely CA)~0°, except the surface of the shortest nanopillars of 390 nm where CA was ~20°. Notably, these surface characteristics as well as morphologies were not altered once exposed to heat and high pressure.

Based on Wenzel ($\cos \theta_{rough} = r \cos \theta$) and C-B ($\cos \theta_{(C-B)} = \varphi\_S \cos \theta - (1-\varphi_S)$) models (FIGS. 8A-B) describing CA on rough surfaces, the measured CA can be explained as a combination of the CA of the starting material and roughness factor (defined by Wenzel as a ratio of the areas of the etched to the smooth surface). Since smooth area equals 1, therefore roughness equals etched area.

etched area = (total area − area occupied by pillars) + area of pillars etched area = (1 − area occupied by pillar) + area of pillars Where:

$$\text{area of pillars} = \frac{\text{pillar density}}{\text{cm}^2} \times \left(\pi r \times \left(r + \sqrt{l^2 + r^2}\right)\right)$$

$$\text{area occupied by pillars} = \frac{\text{pillar density}}{\text{cm}^2} \times (\pi r^2)$$

To promote complete liquid spreading on the surface of given intrinsic CA, a minimum roughness value is required. For this set of surfaces, it appears that a roughness value of ~1.9 is the point that renders a surface to be super-hydrophilic and such was not quite fulfilled in the case of the sample plasma-etched for 1.5 min, possessing roughness of 1.8 (Table 1).

It is believed that the wettability is an effect of surface chemistry and roughness together. In one embodiment, wettability can be controlled by changes to density, diameter, spacing between pillars, by affecting roughness (defined by Wenzel model as ratio of apparent to projected area). The surface having nanopillars can be generated within full wettability range—that means from 0° to >150°. Changes in roughness would generate surfaces from moderately hydrophilic to superhydrophilic. It should be appreciated that hydrophobic and superhydrophobic surfaces would require changes in substrate chemistry. Short molecules could be attached to the hydroxylated surfaces via silanization, for instance. These modified surfaces with various functional groups exhibited would elicit differences in wettability from the parent materials. There is a minimum roughness value required to achieve superhydrophilicty, for instance, in one embodiment, 1.8. Once achieved, further increase in roughness value won't change superhydrophilicity (surface cannot be made more superhydrophilic). However, in certain embodiments, the chemistry of the substrate or the nanopillars can be modified. Such modification of the chemistry, it will change hydrophilicity drastically and such that one could surface modify a superhydrophilic surface and make it less hydrophilic or even superhydrophobic.

Species-Dependent Bactericidal Activity

For the most general application of such coated surfaces, such as in medical applications, it is desirable that the bSi materials should exhibit antimicrobial activities that are generic—exceedingly effective towards virtually any bacterial species. To that end, the interaction of these materials with a range of Gram-negative genera has been investigated using cell viability tests and confocal microscopy. In one embodiment, materials exhibiting nanopillars of 3 μm height showed these desired universal bactericidal properties. In another embodiment, nanopillars having a height of greater than μm. These larger spikes were able to kill certain species with exceptional speed and efficiency (with rates up to an order of magnitude faster than observed for *E. coli* strains).

However, surprisingly, the killing efficiency of shorter nanopillars 2 μm) was found to vary among the bacterial types studied. The differences in efficacy are attributed to a change in the mode of action of bSI, short spikes can stretch and tear the cellular envelopes, as proposed for natural nanospikes, whereas spikes of larger length and width can attract and pierce cells directly with their exceptionally sharp tips. Increased control over silicon fabrication allow materials exhibiting these surfaces to function as selective antimicrobial agents and extend applications far beyond those envisioned for medicine.

Figure 9C:
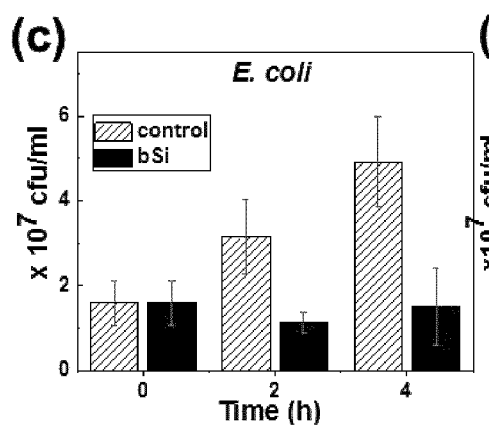
Figure 9D:
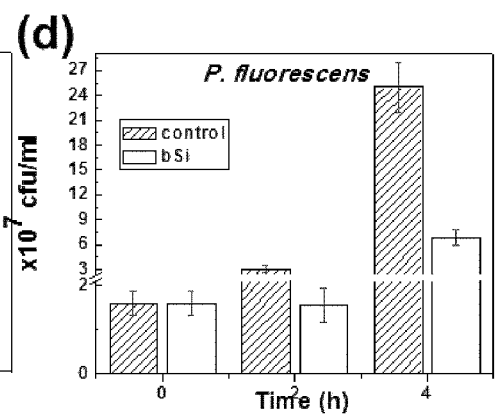

Bactericidal properties of the fabricated surfaces were studied by depositing droplets of cell suspensions in rich medium on top of bSi (FIG. 26B) and on a smooth, non-etched control surface], incubating, plating retrieved cells, and comparing the number of colonies that appeared. These bactericidal experiments were performed in humidity-controlled microchambers (FIG. 9A). For convenience, the various bSi topographies are referred to by nanopillar lengths. The bactericidal efficiencies ("BE") determined based on the percentage of bacteria recovered from bSi versus control surfaces (see eqn. below) of the various surfaces were surveyed initially using *E. coli* as a model Gram-negative species. While bacteria continued to grow on the control surfaces over time, a significantly reduced number of cells was found with the bSi surfaces (FIGS. 9B-C and FIG. 19B).

$$\text{bacterial efficiency} = 100 - \left(\frac{\text{\#colonies after incubation on } bSi}{\text{\#colonies after incubation on } Si} \times 100\right)$$

Here, three characteristic regimes (FIGS. 3C, 4H) of topographies were identified that exhibit similar bactericidal behavior: blunt and short pillars (Regime 1), pillars of intermediate features (Regime 2), and sharp and long pillars (Regime 3). The antibacterial activity was lowest for surfaces with the shortest nanopillars (Regime 1) that most closely mimic the dimensions of the waxy protrusions found in nature (with the possible exception that these surfaces exhibit a wider distribution in pillar shapes and densities (FIG. 7A-B). A previously published report suggested that bactericidal activity of the nanotextured surfaces increases when number of pillars interacting with bacteria also increases.32 Departing from this observation, we found that the bSi surface with the highest nanopillar density showed the lowest BE values for *E. coli*.

Indeed, in the Regime 2, BEs were found to be pillar density-dependent. Within this short-to-mid nanopillar range (L=0.7 μm-2.5 μm), where the nanopillar density decreases dramatically from ca. 12 pillars to ca. 3 pillars per μm$^2$, bactericidal performance at early time (2 h) were 59%, 42%, and 42%, respectively. This density dependence continues to hold at longer surface-interaction times (4 h).

The dependence on density is lost for surfaces with nanopillars longer than 3 μm when BEs are the highest observed (range between 69-81% after 4 h of incubation). The longest needles outperformed the shortest ones by over a factor of two. Although these different BE values may have many origins, it is apparent that sharpness of the nanopillars dramatically improves with the etching time and, thus, with nanopillar length.

The impact of representative surfaces from the three bactericidal Regimes (1-0.4, 2-0.7, and 3-3.6 μm) on the bactericidal efficiency of various bacterial species was investigated (FIGS. 19A-B). Strains from an additional three genera—*Pseudomonas, Rhodobacter*, and *Bacillus*—were chosen as they (along with *E. coli*) represent model laboratory species from biomedical, soil and aquatic environments. After 2 h incubation (FIG. 19A), interestingly, *R. capsulatus* showed an extreme sensitivity to bSi independent of the topography (average killing across all surfaces of 83%). In contrast, *E. coli, P. fluorescens*, and *B. subtilis* were killed less efficiently than *R. capsulatus*. The dependence on bSi topography was shown to be the strongest for *E. coli*, intermediate for *P. fluorescens* and *B. subtilis*, and the weakest for *R. capsulatus*. This pattern holds for longer incubation times (FIG. 19B).

In this study, we focused on responses of various Gram-negative species and compared them to results obtained for a Gram-positive representative *Bacillus*. Surprisingly, *B. subtilis* cells, which have a much thicker peptidoglycan layer than Gram-negative cells, was killed with higher efficiencies than *E. coli* and *P. fluorescens*, suggesting that peptidoglycan layer thickness is likely not the only factor in observed differences between species (FIG. 19).

The differences between the Gram-negative species may be attributed to dissimilarities in their cell-wall stiffness. This rigidity is a combination of glycan chains that are cross-linked with peptides and proteins that connect peptidoglycan with an outer membrane. Glycan chains are generally considered the least flexible of the components. Although it is assumed that peptidoglycan organization is similar in most of the Gram-negative bacteria, in each species the cell wall contains a set of unique proteins that reflect the adaptation to a specific ecological niche. Additionally, it has been suggested that the character of bonding between the peptidoglycan and the outer membrane (covalent vs. electrostatic) contributes to overall cell rigidity.

To gain insight into the apparent lack of effect of bSi surface-topography on *R. capsulatus* killing (FIGS. 19C-D), a wider range of seven bSi surfaces with nanopillar lengths extending up to 6.7 μm was used. The BE values were constant for all bSi surfaces studied when experiments were conducted for 2 or 4 h. A weak but significant surface-dependent killing could be observed only after 45 min incubation, consistent with a higher BE for longer and sharper nanopillars (FIG. 19D).

Approximately half of *R. capsulatus* cells were dead after only a 15 min exposure to bSi surfaces, indicating that the killing kinetics for this species were nearly an order of magnitude faster than for *E. coli*. The killing process continued over time, yielding nearly quantitative killing of *Rhodobacter* after 45 min of interaction with surfaces containing pillars greater than 3 μm. These BE values were comparable with those found after 2 h of incubation.

Attributes of the strains of bacteria tested were compared to the geometries of the bSi nanopillars (FIG. 2C). For all species examined, bactericidal activities of longer nanopillars at lower densities appear to be enhanced by the distinctly greater sharpness and tip length of nanopillars. The lengths of these nanopillars were approximately 10-20 times greater than the lengths of bactericidal protrusions found in nature (typically ~150-440 nm) or bSi reported previously (~620 nm). BE values markedly increased to range from ~71 to 98% (for details, see FIG. 9C-F). These observations are supported by theoretical studies that indicate that antimicrobial properties of nanopatterned surfaces are enhanced when pillars are sharper and the distance between the adjacent pillars increases.

The contribution to killing of clustered pillars (commonly two or three) emerging from a common base (e.g., FIG. 2C)—the frequency of which increases concomitantly (broad pitch distributions at long times; FIG. 6)—is not currently understood. These clusters provide numerous "islands" of heterogeneity where spike pitch/density is locally increased, rendering it possible for a single bacterial cell to be impaled by multiple, exceedingly sharp nanopillars. These clusters likely entrap and rupture cells rapidly and irrecoverably.

Microscopic Validation

The colony-counting method revealed distinct differences in the interactions of E. coli and R. capsulatus with 0.4 and 3.6 μm nanopillars (designated as short/blunt and long/sharp, respectively, hereafter). Confocal microscopy was used to examine the nature of the event(s) that led to the reduction in the number of viable cells to determine whether its origins were enhanced adhesion or actual killing events. Live/dead staining allows characterization of cells present or remaining on the surface and can distinguish viable from dead cells, whereas the colony-counting technique only indicates the viability of planktonic cells (that may or may not have interacted with the surface) and those which were able to detach from the surface during washing steps and recover. The methods are complementary and are required in order to fully characterize antimicrobial properties of surfaces.

The images presented in FIG. 20 reveal that the majority of both E. coli and R. capsulatus cells attached on the bSi surface were dead after 4 h in case of sharp nanopillars (see FIG. 12 for P. fluorescens and B. subtilis). On the blunt surface, dead E. coli cells were scarce, but the frequency of dead R. capsulatus cells was as high as on the sharp nanopillars.

The results confirm plate-based counts. We also noticed that Rhodobacter showed much larger numbers of surface-attached cells relative to the other bacteria. These results are corroborated by higher adhesion of R. sphaeroides (a related species) to hydrophilic mica surfaces relative to E. coli. Also, adhesion of dividing cells to nanostructures might interfere with cell elongation, mid-cell division, and/or separation of the daughter cells. One or both cells may be disrupted or become detached from the surface. The rapid growth rates of E. coli and P. fluorescens may allow one sister cell to escape from the material surface as the other sister is being killed.

Bactericidal properties of fabricated surfaces were studied by depositing droplets of cell suspension on top of bSi and of smooth, non-etched surface (designated control surfaces hereafter), and comparing the number of viable cells able to form colonies on an nutrient agar plate after incubation of a bacterial suspension as a droplet. Attributes of the strains of bacteria tested (Table 2, below) were compared to the geometries of the bSi nanopillars (FIG. 1C). The morphology of the four Gram-negative, rod-shape, motile species are fairly similar. Strains from three genera, Escherichia, Pseudomonas, and Rhodobacter were chosen as they represent model laboratory strains from health, soil and aquatic environments, respectively.

TABLE 2

Morphological and physical features of strains used examples

| Characteristic | E. coli | P. fluorescens | R. sphaeroides | R. capsulatus | B. subtilis |
|---|---|---|---|---|---|
| Strain | DH5α | SBW25 | Δrshl | U43 | NCIB 3610 |
| Cell shape | Rod | rod | rod | rod | rod |
| Cell size: | | | | | |
| diameter (μm) | 0.5-1 | 0.5-0.6 | 0.6-1 | 0.5-1.2 | 1 |
| length (μm) | 1.7-2.5 | 1.5-2 | 1.5-2.5 | 2-2.5 | 3-5 |
| Motility | peritrichously flagellated | multiple polar flagella | single lateral flagellum; | Single polar flagellum | peritrichously flagellated |
| Cell rigidity: | | | | | |
| Viscoelastic parameters $k_1$ and $k_2$ (Nm$^{-1}$) | 0.056 and 0.54 | 0.044 and 0.81* | N/A | N/A | N/A |
| Longitudinal Young's modulus (MPa) | 50-150 | 100-200* | N/A | N/A | 100-200 |
| Biofilm formation | + | + | + | + | + |

*data for Pseudomonas aeruginosa

The bactericidal performance of bSi of length 3.6 μm towards various bacterial species was initially investigated as a benchmark material. This material was of interest as its nanopillar length was approximately 10-20 times higher than the lengths of bactericidal protrusions found in nature (typically ~150-440 nm) or bSi reported previously (~620 nm). Also, the sharpness and uniformity of such pillars appear greatly increased in comparison. Thus, it was hypothesized that these properties may improve the BE of these surfaces. Moreover, the longer pillars may prevent bacterial adhesion to the underlying bulk Si layer. Nanopillars >2 μm have been observed to favor rapid killing (less adhesion potentially) using a direct piercing method.

These experiments were performed in humidity-controlled microchambers of protein crystallization well plates (FIG. 9A). A control surface was chosen by testing non-etched silicon wafer and glass cover slides and their air-plasma treated variants in order to generate hydroxyl groups and alter surface wettability (for details, see FIG. 10). Glass cover slides were chosen as routine controls as they matched more accurately, regardless of surface wettability, the growth of bacteria in culture tubes that were able to be evaluated by measurement of optical densities ($OD_{600}$).

Four bacterial species grown in rich medium were tested at discrete time intervals, under static conditions (no agitation). In all species a reduction in the number of viable cells was observed after 2 h (FIGS. 9B-F). Interestingly, there are significant differences among the killing rates in the four species studies (FIG. 4). After 2 h of the incubation, the lowest BE was observed in the case of *P. fluorescens*, followed by *E. coli*, whereas both *R. capsulatus* and *R. sphaeroides* species were notably more susceptible to bSi-induced killing (BEs of 45, 57, 89 and 88%, respectively). BEs increased with longer incubation times (4 h) to range from ~71 to 100%. It is believed that properties of the organism may impact killing rates for a particular embodiment of nanopillars. For example, flagella length, flagella localization, exopolysaccharide ("EPS") production, quorem sensing and biofilm formation propensity, etc. may impact killing rates.

FIG. 14 illustrates the viability of *R. sphaeroides* on the benchmark, black-silicon surface. Colony forming units were measured by plating on $^G$YCC agar medium after exposure to etched (bSi) and smooth (control) surfaces in $^G$YCC for 2 or 4 h at room temperature. Cells clearly multiplied on the smooth surfaces whereas cells were killed or their growth inhibited on the nanostructured surfaces. The values are expressed as means±SD (n=3 independent experiments).

The viability of the cells adhered to bSi surfaces was monitored by confocal scanning microscopy. LIVE/DEAD® stain was used to discriminate live from dead cells based on the integrity of the cell wall and the relative abilities of the dyes to intercalate into cells. For all species, the majority of cells attached on the bSi surface were dead after 4 h (FIG. 12), confirming plate-based counts. Both species of *Rhodobacter* showed a much higher attachment to the surface relative to the other bacteria. These results are corroborated by higher surface adhesion observed with *R. sphaeroides* interacting with poly-L-lysine-coated mica when studied alongside *E. coli*, suggesting that these differences in species-surface interactions have been observed before and may be rather surface chemistry-independent. Also, if a nanostructure-adhered cell is in the process of dividing, there may be species differences that differentially interfere with processes of cell elongation, mid-cell division, and separation of the daughter cells. One of both of the cells may be disrupted in some cases, and one or both of the cells may become detached in other cases. The rapid growth rate of *E. coli* and *P. fluorescens* may allow for the escape of daughter cells from the materials surface as the parent is in the process of being killed.

In one embodiment, escape of daughter cells is controlled by the use of chemical attractants and/or control of flow or orientation of the mother cell when "stuck" to the nanopillar. It has been observed that if the cell is positioned vertically rather than horizontally, the daughter cell is more likely to escape and not itself be killed. Therefore, in one embodiment, the nanopillars are structured to orient captured or stuck cells horizontally.

In some embodiments, additional materials, such as attractants, cushions, glue, cellular adhesives, polysaccharides, other common mucosal ingredients of biofilms, minerals, cell remnants, or other carbon or energy sources are included. In further embodiments, attractants are also added to the tips and/or to the bulk Si base and/or in the interpillar space. Chemotaxis attractants include, but are not limited to, nutrients, light, oxygen, oxidants and reductants for growth, signals, quorem sensing molecules, metals, amino acids, phosphate, enzyme cofactors, etc.

In some embodiments, flow in and around the nanopillars is controlled. For example, in one embodiment one or both of the nanopillar and/or substrate are magnetic or magnetizable such that a magnetic field can be applied and is present. The magnetic field can be manipulated to control repulsion and/or attraction of organisms or materials of interest.

Insights into the bSi Bactericidal Mechanism

Since bSi acts by mechanical rupturing of bacterial cells, bacteria rigidity has been assumed to play a key role in a species-susceptibility to bSi (and other CWLN). The cell wall in bacteria acts as a physical barrier and is mainly composed of a peptidoglycan—built of repeating disaccharides cross-linked by peptides. Depending on building blocks types and their assemblies, a huge diversity in the chemical and mechanical properties of peptidoglycan is found. Moreover, there are two main arrangements of bacterial walls, the Gram-positive wall with multiple layers of peptidoglycan containing teichoic acids and the Gram-negative wall with a thin layer of peptidoglycan covered by an outer membrane.

Prior materials have been investigated for selectivity with regard to Gram-positive species and Gram-negative ones. For instance, titanium nanostructured materials were demonstrated to selectively kill Gram-negative *E. coli* while *Staphylococcus* ("*S.*") *aureus* growth was not affected. However, as described further below, by contrast to bSi, lower bactericidal efficiencies have been reported for black titanium, regardless of cell wall structure and cell motility. Further, described herein are embodiments having a bactericidal efficiency that is tunable to be species-dependent. For example, *Bacillus* ("*B.*") *subtilis* and *S. aureus*, although killed with relatively high efficiencies, were more resistant than *P. aeruginosa* once exposed to the bSi surface.

In examples of certain embodiments, the responses of Gram-negative species to bSi surfaces were studied. The killing rate of these seemingly comparable species was found to vary with the susceptibility to the surfaces being much lower in *Escherichia* and *Pseudomonas* species. The differences between these Gram-negative species may be attributed to dissimilarities in their cell-wall stiffness. This rigidity is a combination of glycan chains that are cross-linked with peptides and proteins that connect peptidoglycan with an outer membrane. Glycan chains are generally considered the least flexible of the components. Although it is assumed that peptidoglycan organization is similar in most of the Gram-negative bacteria, in each species the cell wall contains a set of unique proteins that reflect the adaptation of that particular bacterial species to a specific ecological niche and associated adaptations for survival in those environments. Additionally, it has been suggested that the character of bonding between the peptidoglycan and the outer membrane (covalent vs. electrostatic) contributes to the overall cell rigidity. Surprising, embodiments described herein provide a mechanism for killing bacteria and other organisms that appears independent of cell wall properties.

Differences may exist in the concentrations of bacterial cells within the droplets. For instance, *Pseudomonas* species being obligate aerobes will prefer to occupy the top of the droplet near the air/water interface where oxygen levels are highest. Other species will likely be more equally distributed throughout the droplet. All of these factors, and their interplay, could be possible explanations of the species dependences that were observed.

Therefore, certain embodiments relate to bSi having topological properties that are tuned to a specific type of cells, such as a species of bacterial. Described herein are representative organisms such as *Escherichia coli*, K-12, *Pseudomonas fluorescens*, *Bacillus subtilis*, *Rhodobacter capsulatus*, and *Rhodobacter sphaeroides*; however, it should be appreciated that certain embodiments described herein may also be used for killing or holding organisms commonly used in medicinal applications (e.g., *Klebsiella pneumoniae*, Salmonella enterica subsp. *enterica serovar Typhimurium*, *Escherichia/Shigella coli*, *Serratia marcescens*, *Dickeya dadantii*, *Yersinia pestis*, *Yersinia enterocolitica*, *Vibrio cholerae*, *Pseudomonas aeruginosa*, *Streptococcus pneumoniae*, *Streptococcus pyogenes*, *Streptococcus dysgalactiae* subsp. *equisimilis*, *Lactococcus lactis*, *Enterococcus faecalis*, *Listeria monocytogenes*, *Staphylococcus epidermidis*; *Staphylococcus aureus*, *Bacillus anthracis*) and also organisms used in biomanufacturing applications (e.g., *Citrobacter freundii*, *Pseudomonas denitrificans*, *Clostridium carboxidivorans*, *Clostridium beijerinckii*, *Lactobacillus delbrueckii* subsp. *bulgaricus*, *Bacillus megaterium*, *Zymomonas mobilis*).

Bacterial Cells Vs. Various Topographies

With embodiments of bSi demonstrated to have generic bactericidal activity, the impact of different bSi topographies, such as those discussed above, on the viabilities of selected representative organisms, *E. coli*, *P. fluorescens*, *R. capsulatus*, was investigated. FIGS. 19C-D present the results obtained after incubation of bacteria for 2 and 4 hours on seven different bSi surfaces with nanopillar lengths ranging from 0.4 to 6.7 μm. As can be seen, *R. capsulatus* showed extremely strong sensitivity regardless of bSi topography (averages across all surfaces of 83% and 92% after 2 and 4 h, respectively). In contrast, for *E. coli* and *P. fluorescens* killing was less efficient than with *Rhodobacter* but exhibited a stronger dependency on bSi topography.

For the latter cases, the responses of the two species were similar, and *E. coli* data will be shown for simplicity. Here, the bactericidal activity was lowest for surfaces with the shortest nanopillars. These short nanopillars somewhat mimic short structures such as waxy protrusions found in nature, with the notable exception that these surfaces exhibit a wider distribution in pillar shapes and densities (FIG. 4). The longest nanopillars outperformed the shortest ones by over a factor of two. While additional factors and correlations between BE and bSi features are described herein, in one embodiment the different BE values is most closely associated with sharpness of the nanopillars, which dramatically improves with the etching time (and, thus, nanopillar length).

Notably, while previously published reports suggest that the bactericidal activity of the CWLN surfaces increases when number of pillars interacting with bacteria also increases, embodiments described herein were observed to have the opposite relationship. Rather, the bSi surface with the densest nanopillars shows the lowest BE values for *E. coli* and *P. fluorescens*. Indeed, for short nanopillars such as described in prior studies, density-dependent BEs is observed for the pillars between 0.7 μm length and 2.5 μm at early time (2 h; 59%, 42%, and 42%, respectively; FIG. 19A). This density dependence continues to hold at longer surface-interaction times (4 h). Within this short-to-mid nanopillar range, the pillar density decreases dramatically from ca. 12 pillars to ca. 3 per 1 μm². The dependence on density is lost again for surfaces with nanopillars longer than 3 μm when BE are the highest observed for these species (range between 69-81% after 2 h and 4 h of incubation time). Therefore, it has surprisingly been found that for larger (3 μm and above) nanopillars, the trend previously observed is reversed, with superior bactericidal properties associated with decreased density.

For *Rhodobacter*, the relatively quicker cell death required examination of much shorter incubation times (15 and 45 mins) (FIG. 19C). Here, after only 15 min, approximately half of the *Rhodobacter* cells was found dead. The killing process continued during the additional 30 min of the incubation with bactericidal rates related to the topographical features of the nanopillars. Nearly quantitative killing of *Rhodobacter* was observed after 45 min of interacting with the surfaces containing pillars greater than 3 μm. These BE values were nearly the same as those found after 2 h of the incubation. In general, however, the shorter pillars showed a smaller BE value increase (just 7-12%) between the 15 and 45 min observations.

For bactericidal activities of all species examined, lower spike densities of the longer nanopillars appear to be more than compensated by distinctly enhanced nanopillar sharpness and tip length. Complicating this mechanistic understanding is the contribution of clustered pillars (commonly two or three) growing from a common base (e.g., FIG. 1C), the frequency of which increases concomitantly (broad pitch distributions at long times; FIG. 6). These clusters provide numerous "islands" of heterogeneity where spike pitch/density is locally increased, rendering it possible for a single bacterial cell to be impaled by multiple, exceedingly sharp nanopillars. These clusters likely entrap and irrecoverably rupture cells rapidly. These observations are supported by theoretical studies that indicate that antimicrobial properties of the CWLN are enhanced when pillars are sharper and the distance between the adjacent pillars increases.

New Mechanistic Insights

The most commonly reported mechanism describing bSi-mediated cell death is associated with adsorption of bacteria on these patterned surfaces (tips) followed by tip-mediated penetration of bacterial cell walls. In contrast, it has been suggested that nanopillars displaying spherical, more blunt, caps (not sharp; like those found in nature), most likely act through their density by breaking membranes that are suspended between adjacent pillars; this action results from stretching forces rather than direct impalement of a cell body. Nonetheless, it has been demonstrated that performance of these engineered structures is strongly dependent on cell mechanical properties and cell-substrate interaction parameters—not solely the nanotopographical features of the etched surfaces.

Figures 27A, 27B, 27C:
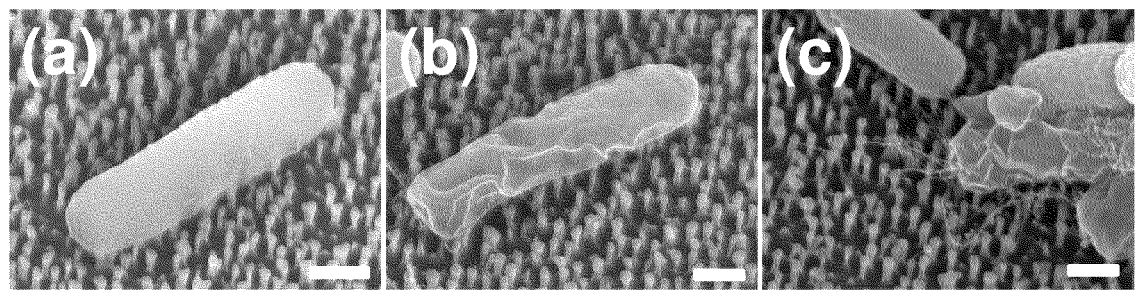
Figures 27D, 27E, 27F:
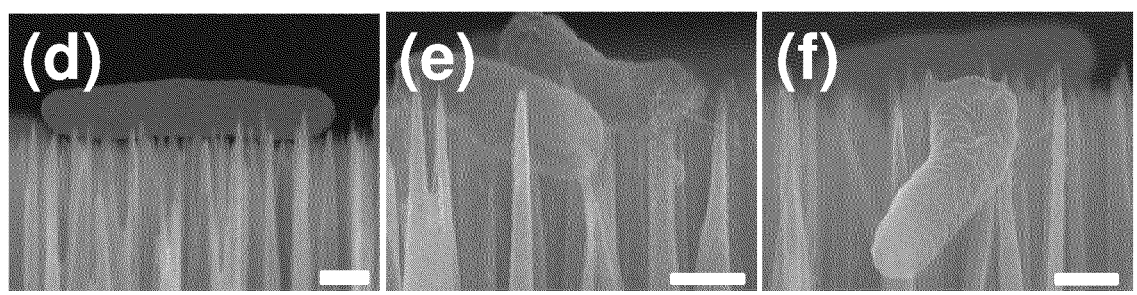

In order to gain more mechanistic insights into the bactericidal activity of bSi, SEM imaging was used to examine cell-pillar interactions (FIG. 25A-27F). Indeed, sharp pillars clearly pierce the cells (FIGS. 25b and 25d) whereas blunt pillars do not (FIGS. 6a and c). Except for the dissimilarity in killing efficiencies for short pillars found by colony-counting and live/dead staining methods, no obvious distinctions in cell-pillar interactions were found between species. As shown for *E. coli* (FIG. 27A-F), the mechanism of death is a process of adhesion to nanopillars (a, d), followed by stretching of the membrane (blunt, FIG. 27B) or piercing (sharp, FIG. 27E), provoking cytoplasm leakage and complete cell rupture (FIGS. 27C,F). Eventually, the cell body either rests atop blunt nanopillars (FIG. 27C), never reaching the bulk Si, or hangs from the sharp tips that pierced them (FIG. 27F). In some cases, sharp pillars can be seen to pass through both sides of the cell. The tips of blunt pillars were never observed to stick up through the cellular debris/deflated cells as for the sharp pillars, further indicating that the mechanism of killing for these nanopillars is not direct piercing. Both mechanisms could be working in the case of pillars of intermediate length.

In one embodiment, the cell wall or cellular membrane of organisms is disrupted by an additive. For example, enzymes may be utilized to break down the cell wall, divalent cations may be used to increase porosity of cellular walls and cellular membranes. Physical engagement may also be used, such as sonication, ultrasound, or temperature to alter the cellular walls and/or cellular membranes.

Although bSi topography is a major factor in the bactericidal mechanism, our findings also demonstrate that killing strongly depends on cellular features that enhance interactions with the bSi surface. The attractive strength (bacterial adhesion) towards the surface is known to play a role and it leads to membrane stretching. Especially in the case of the mechanism for short, blunt nanopillars, this step seems to be particularly important. In general, adhesion is driven by multiple factors including surface chemistry, environment, and properties of the bacterial cell wall that include structural features such as the presence and cellular distribution of flagella and fimbriae, and the chemical composition of lipopolysaccharides.

FIG. 8 shows the arrangement of these appendages around nanofeatures (red arrows), indicating their role when interacting with such surfaces. These outward-facing and dynamic cellular features affect the ability of cells to interact with surfaces through a variety of means (e.g., electrostatic interactions, van der Waals forces, hydrophobic interactions, and hydrogen bonding). However, no study thus far has demonstrated the impact of various surface chemistries on the bactericidal performance of the material. The controlled synthesis of bSi of varied nanotopographies may be used in the future to distinguish between the impacts of some of these biotic/abiotic interactions and may result in the design of experiments to better determine mechanisms of cell death induced by natural as well as synthetic nanotextured materials.

It is noteworthy that although long and sharp pillars always exhibit the best antimicrobial performance, there are some differences in bactericidal rate between species (FIG. 4). Rapid death of Rhodobacter species suggests that cell penetration by sharp pillars occurs nearly immediately after these cells associate with bSi tips. However, similar BE in the case of E. coli was found to require at least 2 h. Thus, differences in cellular rigidity between bacterial species may come into play. The results may also indicate that E. coli requires a longer time of interaction on the tips to generate the tension and stretching that is sufficient for disruption of this cell type. After all, they are ultimately pierced (FIGS. 25-27). Tension imparted by a single nanopillar or cluster of nanopillars is a direct result of tip geometry and their compatibility with the cell-wall and cytoskeletal-like structures of these bacterial species. Inspiration for how these cellular parameters lead to differences in the species-dependent BE observed may be derived from mechanisms that have recently been used with success to describe nanowire penetration of eukaryotic cells of various stiffness.

Additional mechanistic insights may be revealed using fluorescently labelled strains that allow visualization of the interactions of cells with these surfaces in real time, a technique that has been absent from this field thus far. Cells dynamically interacting with etched and smooth surfaces are captured in ESI, Motility tracking was used to distinguish between reversible and permanent attachments Based on cellular velocities and angles between the cells and their direction of motion, B. subtilis cells are killed within just a few seconds of interacting with sharp nanopillars. Time-lapse confocal imaging will be an important tool for these studies moving forward as they lead to a mechanistic understanding of bactericidal activity of nanotextured surfaces. Here, 2D or 3D bacterial tracking will be used (i) to differentiate between a set of proposed mechanisms and (ii) to identify key cellular properties that allow for selectivity of bactericidal effects, FIGS. 24A-B show bactericidal efficiencies of etched silicon (L=390 nm) towards E. coli (FIG. 24A) and R. capsulatus (FIG. 24B).

FIGS. 25A-D show SEM micrographs of E. coli (top row) and R. capsulatus (bottom row) attached to black silicon surfaces: (FIGS. 25A, 25C) blunt and (FIGS. 25B, 25D) sharp nanopillars (samples: 0.4 and 3.6 µm, respectively). The images present two different mechanisms leading to cell death where only the sharp pillars can penetrate the cell body. Scale bars 500 nm. (FIGS. 25A, 25C) tilted 30°, (FIGS. 25B, 25D) tilted 45°.

FIG. 26 is an SEM micrograph of E. coli with sharp nanopillar passing through. Scale bar 1 µm.

FIGS. 27 A-F are SEM micrographs of E. coli (top row) and R. capsulatus (bottom row) attached onto smooth (FIGS. 27A-B) and black silicon surfaces: (FIGS. 27C-D) blunt and (FIGS. 27E-F) sharp nanopillars (samples: 0.4 and 3.6 µm, respectively). The red arrows indicate bacterial adhesions arranged around nanofeatures. Scale bars 500 nm. (FIGS. 27 A-D) tilted 30°, (FIGS. 27E-F) top views.

FIG. 28 is an SEM micrograph of cellular debris remained (or vanishing) after nanopillars-driven killing. The image indicates technology sustainability where the same surface is capable of interacting with another cell.

Chemical deposition such as ALD, CVD, as well as spattering, silane chemistry, "click" chemistry, and other surface chemistry techniques may be used to modify the pillars. Such modification techniques can selectively enhance the rigidity of the nanopillars or select portions of the nanopillars, such as cores, bases, stalks, to give them additional strength/shells. Further, such surface modifications may also control the propensity of organisms to "stick" to the nanopillars, such as by making the nanopillar more pliable.

Conclusions from Experiments

Protection from bacterial infection and colonization is afforded in biology by nanotexturing on the surfaces of plants, insect wings, lizards, and sharks. Many synthetic analogs have emerged with similar antimicrobial activities. We present, for the first time, advances in materials fabrication that have generated performance-enhanced mimetics with antimicrobial activities that are shown to be superior to those of natural surfaces (either exceptional killing percentages and rates or selectivity in species that were targeted). The characterization of these surfaces and bactericidal activities was approached systematically and allowed us to identify key material parameters that affect the way in which bacteria interact with these surfaces and eventually lead to cell death. The characterization of the activity of these surfaces was accentuated by time-lapse confocal microscopy that captured events that are indicative of cellular immobilization and rupture, Two different mechanisms are obvious in the interaction of microbial cells with these textured surfaces. The longer, exceedingly sharp pillars are capable of piercing all types of microbial cells directly and are found to be nonselective regarding species. The shorter, blunt pillars require multifaceted cellular interactions that eventually stretch and tear the membrane envelopes. These interactions appear to be species specific and result in differential rates of interaction and disruption.

The properties of the nanotexturing appear to dictate the mechanism by which the surface interacts with and disrupts the cell. We find that the rate of killing by a selected surface is dictated by the properties of the bacterial cell (e.g., nature of the cell wall, peptidoglycan layer, and outer membrane; abundance and localization of flagella; extent and composition of secreted polysaccharides, etc.). Additional studies of more diverse members of the bacterial kingdom will likely reveal correlations that can be used for designer materials that specifically target or avoid select classes or species of microbes. Once properly tuned for an application, these advanced surfaces can be deployed as antimicrobial agents in ways that are just beginning to be envisioned: from display on biomedical, food preparation, and water purification surfaces to incorporation into cosmetics or use as enhancements in agrochemical pesticides.

Nanotextured Material Based Assay Experiment

For *R. capsulatus* cells incubated passively for 4 hours atop Regime-3 bSi surfaces, the release of 22% of total plasmid DNA was observed (assuming a plasmid copy number of 5 per cell [Khan et al, 2008] and purchased competent cells of known transformation efficiency of ~2.5× $10^8$/µg for a broad host range plasmid of 5146 bp). In addition, this same exposure has been shown to release ~18% of total cytosolic protein (as measured by Pierce 660 nm protein assay reagent kit for cells subjected to bSi versus those completely lysed chemically by a commercial reagent, Pierce Fast Break™). This was confirmed by breaking the cells mechanically with a microfluidizer. These similar numbers likely reflect the total percentages of cells that were ruptured where bSi interaction caused disintegration or whereby holes remained such that cellular contents could spill out. Similar percentage release values would be expected for metabolites, RNA, lipids, and other soluble cellular components. These released molecule sets are available for study by all available cellular analytical techniques. Release of a minor amount of cellular contents (<5% in all cases) was observed for controls where cells were exposed to smooth surfaces, reflecting a proportion of dead cells in the bacterial culture (correlating well with the amount of naturally dead cells found in cytometric analysis).

As described, the universality and killing efficiency can be greatly improved by fabrication of bSi with longer nanopillars and with tips of increased sharpness. Such b-Si surfaces can be as antimicrobial coatings to prevent biofouling. Production is scalable and relatively cost effective using ICP RIE approaches. Further, the prior ICP RIE approach can be modified to use different DC Bias (etching rate) to vary tip shapes. Additionally tip can be sharpened by using short time (few-tens seconds) baths in HF or changed to blunt (along with height) by Ar plasma. In general, plasma etching is suitable for wafer scale large area fabrication.

In one embodiment, the bSi material described herein is associated with a substrate. The substrate may be rigid or flexible. In one embodiment, bSi serves as a mold and nanoimprinting technique could be used to achieve topographies in flexible materials.

In one embodiment, the bSi material can by fabricated, for example, by 3D printing via two-photon lithography, or via dynamic self-assembly (for example, see "Self-assembled tunable networks of sticky colloidal particles," Demortiere, et al., Nature communications 5, 3117 (2014)), incorporated herein by reference.

As used herein, the singular forms "a," "an," and "the" include plural referents unless the context clearly dictates otherwise. Thus, for example, the term "a member" is intended to mean a single member or a combination of members, "a material" is intended to mean one or more materials, or a combination thereof.

As used herein, the terms "about" and "approximately" generally mean plus or minus 10% of the stated value. For example, about 0.5 would include 0.45 and 0.55, about 10 would include 9 to 11, about 1000 would include 900 to 1100.

It should be noted that the term "exemplary" as used herein to describe various embodiments is intended to indicate that such embodiments are possible examples, representations, and/or illustrations of possible embodiments (and such term is not intended to connote that such embodiments are necessarily extraordinary or superlative examples).

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Other substitutions, modifications, changes and omissions may also be made in the design, operating conditions and arrangement of the various exemplary embodiments without departing from the scope of the present invention.

While this specification contains many specific implementation details, these should not be construed as limitations on the scope of any inventions or of what may be claimed, but rather as descriptions of features specific to particular implementations of particular inventions. Certain features described in this specification in the context of separate implementations can also be implemented in combination in a single implementation. Conversely, various features described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

We claim:

1. A nanotextured material comprising:
    a substrate having a plurality of nanopillars extending there from and having a density of between 2 and 20 pillars per micrometer squared, at least a portion of the plurality of nanopillars being functionalized with silane chemistry;
    each of the plurality of nanopillars having a narrowed tip opposite the substrate, each nanopillar tip having a tip angle of 20° to 10° and a length of between 400 nm and 10 µm, with an aspect ratio of 14-16, each nanopillar tip comprising from 18% to 50% of the length for each respective one of the plurality of nanopillars; and
    the plurality of nanopillars forming clusters, each cluster comprising at least two nanopillars.

2. The nanotextured material of claim 1, wherein each of the plurality of nanopillars has a nanopillar diameter of 50 nm to 490 nm.

3. The nanotextured material of claim 1, wherein the substrate and nanopillars comprise silicon.

4. The nanotextured material of claim 1 wherein the substrate is a wafer.

5. The nanotextured material of claim 1, wherein the plurality of nanopillars comprise a first set with a first pillar height and a second set with a second pillar height different from the first pillar height.

* * * * *